(12) United States Patent
Austad et al.

(10) Patent No.: US 11,078,190 B2
(45) Date of Patent: *Aug. 3, 2021

(54) POLYMORPHS OF SELINEXOR

(71) Applicant: Karyopharm Therapeutics inc., Newton, MA (US)

(72) Inventors: Brian C. Austad, Tewksbury, MA (US); David G. Roe, Rockwood (CA)

(73) Assignee: Karyopharm Therapeutics Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,630

(22) Filed: Nov. 11, 2019

(65) Prior Publication Data

US 2020/0283419 A1 Sep. 10, 2020

Related U.S. Application Data

(63) Continuation of application No. 15/503,319, filed as application No. PCT/US2015/045395 on Aug. 14, 2015, now Pat. No. 10,519,139.

(60) Provisional application No. 62/038,069, filed on Aug. 15, 2014.

(51) Int. Cl.
*C07D 403/12* (2006.01)
*A61K 31/497* (2006.01)
*A61P 35/00* (2006.01)

(52) U.S. Cl.
CPC .......... *C07D 403/12* (2013.01); *A61K 31/497* (2013.01); *A61P 35/00* (2018.01); *C07B 2200/13* (2013.01)

(58) Field of Classification Search
CPC .................................................. C07D 403/12
See application file for complete search history.

(56) References Cited

U.S. PATENT DOCUMENTS

| | | | |
|---|---|---|---|
| 5,153,201 A | 10/1992 | Aono et al. | |
| 5,817,677 A | 10/1998 | Linz et al. | |
| 6,462,049 B1 | 10/2002 | Ogura et al. | |
| 7,342,115 B2 | 3/2008 | Hutchison et al. | |
| 7,667,041 B2 | 2/2010 | Kimura et al. | |
| 7,795,457 B2 | 9/2010 | Fu et al. | |
| 7,858,621 B2 | 12/2010 | Kim et al. | |
| 7,902,367 B2 | 3/2011 | Nomura et al. | |
| 8,273,738 B2 | 9/2012 | Osakada et al. | |
| 8,299,102 B2 | 10/2012 | Strobel et al. | |
| 8,304,438 B2 | 11/2012 | Strobel et al. | |
| 8,513,230 B2 | 8/2013 | Shacham et al. | |
| 8,598,168 B2 | 12/2013 | Moradei et al. | |
| 8,999,996 B2 | 4/2015 | Sandanayaka et al. | |
| 9,079,865 B2 | 7/2015 | Sandanayaka et al. | |
| 9,096,543 B2 | 8/2015 | Sandanayaka et al. | |
| 9,206,158 B2 | 12/2015 | Sandanayaka et al. | |
| 9,266,843 B2 | 2/2016 | Sandanayaka et al. | |
| 9,303,000 B2 | 4/2016 | Sandanayaka et al. | |
| 9,428,490 B2 | 8/2016 | Sandanayaka et al. | |
| 9,550,757 B2 | 1/2017 | Shacham et al. | |
| 9,585,874 B2 | 3/2017 | Sandanayaka et al. | |
| 9,714,226 B2 | 7/2017 | Sandanayaka et al. | |
| 9,738,624 B2 | 8/2017 | Baloglu et al. | |
| 9,828,373 B2 | 11/2017 | Liu et al. | |
| 9,861,614 B2 | 1/2018 | Sandanayaka et al. | |
| 10,058,535 B2 | 8/2018 | Sandanayaka et al. | |
| 10,173,987 B2 | 1/2019 | Sandanayaka et al. | |
| 10,202,366 B2 | 2/2019 | Rashal et al. | |
| 10,335,393 B2 | 7/2019 | Sandanayaka et al. | |
| 10,407,405 B2 | 9/2019 | Baloglu et al. | |
| 10,519,139 B2 * | 12/2019 | Austad ................. | A61K 31/497 |
| 10,526,295 B2 | 1/2020 | Baloglu | |
| 10,544,108 B2 | 1/2020 | Sandanayaka et al. | |
| 10,709,706 B2 | 7/2020 | Baloglu | |
| 2003/0018025 A1 | 1/2003 | Thurkauf et al. | |
| 2004/0092598 A1 | 5/2004 | Watkins et al. | |
| 2006/0004069 A1 | 1/2006 | Momose et al. | |
| 2009/0221586 A1 | 9/2009 | Okada et al. | |
| 2009/0298896 A1 | 12/2009 | Sakuma et al. | |
| 2010/0016272 A1 | 1/2010 | Strobel et al. | |
| 2010/0056569 A1 | 3/2010 | Nan et al. | |

(Continued)

FOREIGN PATENT DOCUMENTS

| | | |
|---|---|---|
| CN | 101309912 A | 11/2008 |
| CN | 101466687 A | 6/2009 |

(Continued)

OTHER PUBLICATIONS

Notice of Allowance for U.S. Appl. No. 15/651,856, "Nuclear Transport Modulators and Uses Thereof" dated Apr. 24, 2019.
Notice of Allowance for U.S. Appl. No. 15/629,307, Hydrazide Containing Nuclear Transport Modulators and Uses Thereof dated Aug. 29, 2008.
Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Brekhov, Y. et al., "Cyanomethyltetrazoles II reactions of the methylene Fragment", Zhurnal organicheskoi Khimii, 28(9): 1921-1925 (1992).
Brittain, "Drugs in Pharmaceutical Sciences, v. 192. Polymorphism in Pharmaceutical Solids," CRC Press (2009).

(Continued)

*Primary Examiner* — Paul V Ward
(74) *Attorney, Agent, or Firm* — Foley Hoag LLP

(57) ABSTRACT

The present invention relates to crystalline forms of the compound represented by Structural Formula I, and compositions comprising crystalline forms of the compound represented by Structural Formula I described herein. The crystalline forms of the compound of Structural Formula I and compositions comprising the crystalline forms of the compound of Structural Formula I provided herein, in particular, single crystalline Form A, can be incorporated into pharmaceutical compositions, which can be used to treat various disorders associated with CRM1 activity, including cancer. Also described herein are methods for preparing the compound of Structural Formula I and its single crystalline forms.

20 Claims, 25 Drawing Sheets

(56) References Cited

U.S. PATENT DOCUMENTS

| | | |
|---|---|---|
| 2011/0009374 A1 | 1/2011 | Keller |
| 2011/0275607 A1 | 11/2011 | Shacham et al. |
| 2012/0258986 A1 | 10/2012 | Sandanayaka et al. |
| 2013/0317031 A1 | 11/2013 | Sandanayaka et al. |
| 2014/0155370 A1 | 6/2014 | Shacham et al. |
| 2014/0235653 A1 | 8/2014 | Sandanayaka et al. |
| 2014/0364408 A1 | 12/2014 | Sandanayaka et al. |
| 2015/0018332 A1 | 1/2015 | Sandanayaka et al. |
| 2015/0111893 A1 | 4/2015 | Sandanayaka et al. |
| 2015/0274698 A1 | 10/2015 | Sandanayaka et al. |
| 2016/0145246 A1 | 5/2016 | Sandanayaka et al. |
| 2016/0152596 A1 | 6/2016 | Baloglu et al. |
| 2016/0258931 A1 | 9/2016 | Silva et al. |
| 2016/0304500 A1 | 10/2016 | Rashal et al. |
| 2017/0137430 A1 | 5/2017 | Sandanayaka et al. |
| 2017/0319551 A1 | 11/2017 | Sandanayaka et al. |
| 2018/0155317 A1 | 6/2018 | Baloglu et al. |
| 2019/0016690 A1 | 1/2019 | Baloglu |
| 2019/0023693 A1 | 1/2019 | Chennuru et al. |
| 2019/0160063 A1 | 5/2019 | Baloglu |
| 2020/0087313 A1 | 3/2020 | Sandanayaka et al. |
| 2020/0199099 A1 | 6/2020 | Baloglu et al. |
| 2020/0283419 A1 | 9/2020 | Austad et al. |
| 2020/0339521 A1 | 10/2020 | Sandanayaka et al. |

FOREIGN PATENT DOCUMENTS

| | | |
|---|---|---|
| CN | 103002742 A | 3/2013 |
| CN | 103874690 B | 7/2016 |
| EP | 0069513 A2 | 1/1983 |
| EP | 1 939 180 A1 | 7/2008 |
| EP | 1992618 A1 | 11/2008 |
| EP | 2003118 A1 | 12/2008 |
| EP | 2 090 570 A1 | 8/2009 |
| JP | S5841875 A | 3/1983 |
| JP | S62103065 A | 5/1987 |
| JP | H04211089 A | 8/1992 |
| JP | H07118237 A | 5/1995 |
| JP | H11263764 A | 9/1999 |
| JP | 2003/342262 A | 12/2003 |
| JP | 2004509941 A | 4/2004 |
| JP | 2004168768 A | 6/2004 |
| JP | 2005-508905 A | 4/2005 |
| JP | 2005-255683 A | 9/2005 |
| JP | 2006-504761 A | 2/2006 |
| JP | 2007-210929 A | 8/2007 |
| JP | 2009-203238 A | 9/2009 |
| JP | 2009-536615 A | 10/2009 |
| JP | 2009-544696 A | 12/2009 |
| JP | 2010-513341 A | 4/2010 |
| JP | 2010-519337 A | 6/2010 |
| JP | 2015-516434 A | 6/2015 |
| KR | 20050062645 A | 6/2005 |
| WO | WO-96/16040 A1 | 5/1996 |
| WO | WO-97/15567 A1 | 5/1997 |
| WO | WO-97/37996 A1 | 10/1997 |
| WO | WO-97/48696 A1 | 12/1997 |
| WO | WO-98/25893 A1 | 6/1998 |
| WO | WO-99/50264 A1 | 10/1999 |
| WO | WO-01/62756 A1 | 8/2001 |
| WO | WO-02/26696 A1 | 4/2002 |
| WO | WO-2003/024448 A2 | 3/2003 |
| WO | WO-2004/039365 A1 | 5/2004 |
| WO | WO-2004/039764 A1 | 5/2004 |
| WO | WO-2004/043925 A2 | 5/2004 |
| WO | WO-2004/043951 A1 | 5/2004 |
| WO | WO-2004/076418 A1 | 9/2004 |
| WO | WO-2005/115990 A1 | 12/2005 |
| WO | WO-2006/016637 A1 | 2/2006 |
| WO | WO-2006/019020 A1 | 2/2006 |
| WO | WO-2006/088246 A1 | 8/2006 |
| WO | WO-2007/102580 A1 | 9/2007 |
| WO | WO-2007/147336 A1 | 12/2007 |
| WO | WO-2008/029825 A1 | 3/2008 |
| WO | WO-2008/074413 A2 | 6/2008 |
| WO | WO-2008/152097 A1 | 12/2008 |
| WO | WO-2010/017545 A2 | 2/2010 |
| WO | WO-2011/069039 A1 | 6/2011 |
| WO | WO-2011/109799 A1 | 9/2011 |
| WO | WO-2012/099807 A1 | 7/2012 |
| WO | WO-2013/019548 A1 | 2/2013 |
| WO | WO-2013/019561 A1 | 2/2013 |
| WO | WO-2013/020024 A2 | 2/2013 |
| WO | WO-2013/170068 A2 | 11/2013 |
| WO | WO-2014/144772 A1 | 9/2014 |
| WO | WO-2014/152263 A1 | 9/2014 |
| WO | WO-2014/205389 A1 | 12/2014 |
| WO | WO-2014/205393 A1 | 12/2014 |
| WO | WO-2016/025904 A1 | 2/2016 |
| WO | WO-2017/117529 A1 | 7/2017 |
| WO | WO-2017/117535 A1 | 7/2017 |
| WO | WO-2018/098472 A1 | 5/2018 |
| WO | WO-2018/129227 A1 | 7/2018 |

OTHER PUBLICATIONS

Bryn, "Pharmaceutical Solids: A Strategic Approach to Regulatory Considerations," Pharma Res 12(7):945-954 (1995).

Buckler, R.T. et al., "Synthesis and Antiinflammatory Activity of Some 1,2,3- and 1,2,4-Triazolepropionic Acids", Journal of Medicinal Chemistry, 21(12): 1254-1260 (1978).

Burdeska et al., "Anil-Synthese. 23. Mitteilung. Ueber die Herstellung von Styryl- and Stilbenyl-Derivaten des Pyrimidins // Anil synthesis. Part 23. Preparation of styryl and stilbenyl derivatives of pyrimidines," Helv Chim Acta, 64(1): 113-152 (1981).

Cai, X., et al., "Inhibition of Thr-55 phosphorylation restores p53 nuclear localization and sensitizes cancer cells to DNA damage", Proc Nat Acad Sci, 105(44):16958-16963 (2008).

Cancer [online], [retrieved on Jul. 6, 2007] Retrieved from the Internet, URL: http://www.nlm.nih.gov/medlineplus/cancer.html (Year: 2007).

Cantu et al., "Using the Selective Inhibitor of Nuclear Export (SINE) Compound KPT-350 to Reduce Cortical Circuit Hyperexcitability and Interneuron Cell Loss in the Controlled Cortical Impact (CCI) Model of Traumatic Brain Injury (TBI) (I11.001)," Neurology, 86(16 Supplement):IT1.001 (2016).

CHEMCATS RN# 1035122-02-1; Publicly available on Jul. 12, 2009.

CHEMCATS RN# 1134927-58-4; Publicly available on Apr. 15, 2009.

CHEMCATS RN# 930886-49-0; Publicly available on Apr. 29, 2007.

Cheng et al., "XPO1 (CRM1) Inhibition Represses STAT3 Activation to Drive a Surviving-Dependent Oncogenic Switch in Triple-Negative Breast Cancer," Mol Cancer Ther 13(3):675-686 (2014).

Cooper et al., "Synthesis of Some 1,2,4-Triazoles and 1,2,4-Triazolines by Reaction of Oxamidrazone Condensation Products with Acetic Anhydride," Journal of Chemical Society Perkin Transactions 1, 15: 1433-1437 (1975).

Cronshaw, J.M. et al., "The nuclear pore complex: disease associations and functional correlations", Trends Endocrin Metab. 15:34-39 (2004).

Daelemans, D. et al., "A synthetic HIV-1 Rev inhibitor interfering with the CRM1-mediated nuclear export", PNAS, 99(22):14440-14445 (2002).

Database PubChem Compound, Database Accession No. 33777540 (May 29, 2009), 3 pages.

Database PubChem Compound, Database Accession No. 33777561 (May 29, 2009), 3 pages.

Database PubChem Compound, Database Accession No. 33777585 (May 29, 2009), 3 pages.

Database PubChem Compound, Database Accession No. 66525271 (Oct. 24, 2012), 3 pages.

Database PubChem Compound, Database Accession No. 66525276 (Oct. 24. 2012), 3 pages.

Database PubChem Compound, Database Accession No. 72062355 (2007), 11 pages.

Database PubChem Compound, Database Accession No. 940775133 (Jul. 7, 2017), 1 page.

(56) References Cited

OTHER PUBLICATIONS

Davis, J.R. et al., "Controlling protein compartmentalization to overcome disease" Pharmaceut Res., 24:17-27 (2007).
Dorwald, "Side Reactions in Organic Synthesis: A Guide to Successful Synthesis Design," Wiley-VCH Verlag GmbH & Co. KGaA, Weinheim (2005).
Etchin et al., "KPT-330 inhibitor of CRM1 (XPO1)-mediated nuclear export has selective anti-leukaemic activity in preclinical models of T-cell acute lymphoblastic leukaemia and acute myeloid leukaemia," British Journal of Haematology, 161:117-127 (2013).
Extended European Search Report for EP Application No. 17189480.1 dated May 16, 2018.
Extended European Search Report for EP Application No. EP 18202641 dated Feb. 15, 2019.
Extended European Search Report issued by the European Patent Office in corresponding European Application No. 18164757.0 dated Aug. 8, 2018.
Extended Search Report for EP Application No. 11751491.9, "Nuclear Transport Modulators and Uses Thereof", Date of Completion of the Search: Dec. 17, 2013.
Extended Search Report for EP Application No. 12736172.3, "Olefin Containing Nuclear Transport Modulators and Uses Thereof", Date of Completion of the Search: May 8, 2014.
Falini, B. et al., "Both carboxy-terminus NES motif and mutated tryptophan(s) are crucial for aberrant nuclear export of nucleophosmin leukemic mutants in NPMc+ AML", Blood Journal, 107(11):4514-4523 (2013).
Freundt, E.C. et al., "Molecular Determinants for Subcellular Localization of the Severe Acute Respiratory Syndrome Coronavirus Open Reading Frame 3b Protein", Journal of Virology, 83(13):6631-6640 (Jul. 2009).
Ghildyal, R. et al., "The Respiratory Syncytial Virus Matrix Protein Possesses a Crm1-Mediated Nuclear Export Mechanism", Journal of Virology, 83(11):5353-5362 (2009).
Ghosh, C.C. et al., "Analysis of nucleocytoplasmic shuttling of NF kappa B proteins in human leukocytes", Methods Mol. Biol. 457:279-92 (2008).
Golub, T.R. et al., "Molecular Classification of Cancer: Class Discovery and Class Prediction by Gene Expression Monitoring", Science, 286: 531-537 (1999).
Gravina et al., "XPO1/CRM1-Selective inhibitors of nuclear export (SINE) reduce tumor spreading and improve overall survival in preclinical models of prostate cancer (PCa)," Journal of Hematology & Oncology, 7(46):1-17 (2014).
Gupta, N. et. al., "Retinal tau pathology in human glaucomas" Can J Ophthalmol. 43(1):53-60 (2008).
Haines et al., "Selective Inhibitors of Nuclear Export Avert Progression in Preclinical Models of Inflammatory Demyelination," Nature Neuroscience, 18(4): 511-520 (2015).
Hilliard et al., "The anti-inflammatory prostaglandin 15-Deoxy-$\Delta$12,14 PGJ2 inhibits CRM1-dependent nuclear protein export," Journal of Biological Chemistry, 1-12 (2010).
Hoffman et al., "Synthesis of Vinyl-Functionalized Oxazoles by Olefin Cross-Metathesis", J. Org. Chem. 73: 2400-2403 (2008).
Hoshino, I. et al., "Combined effects of p53 gene therapy and leptomycin B in human esophageal squamous cell carcinoma", Oncology, 75:113-119 (2008).
Huff, J., "HIV Protease: A Novel Chemotherapeutic Target for AIDS", Journal of Medicinal Chemistry, 34(8): 2305-2314 (1991).
International Preliminary Report on Patentability for International Application No. PCT/US2011/027328, "Nuclear Transport Modulators and Uses Thereof" dated Sep. 11, 2012.
International Preliminary Report on Patentability for International Application No. PCT/US2012/021406, "Olefin Containing Nuclear Transport Modulators and Uses Thereof" dated Jul. 17, 2013.
International Preliminary Report on Patentability for International Application No. PCT/US2014/029322 dated Sep. 15, 2015.
International Preliminary Report on Patentability for International Application No. PCT/US2014/043479, dated Dec. 22, 2015.
International Preliminary Report on Patentability for International Application No. PCT/US2014/043484, dated Dec. 22, 2015.
International Preliminary Report on Patentability for International Application No. PCT/US2015/045395 dated Feb. 21, 2017.
International Preliminary Report on Patentability for International Application No. PCT/US2016/069492 dated Jul. 3, 2018.
International Preliminary Report on Patentability for International Application No. PCT/US2016/069508 dated Jul. 3, 2018.
International Preliminary Report on Patentability for International Application No. PCT/US2017/063439 dated May 28, 2019.
International Preliminary Report on Patentability for International Application No. PCT/US2012/048319, "Hydrazide Containing Nuclear Transport Modulators and Uses Thereof"; Date of Issuance of the Report: Feb. 4, 2014.
International Preliminary Report on Patentability for International Application No. PCT/US2012/048368, "Nuclear Transport Modulators and Uses Thereof"; Date of Issuance of the Report: Feb. 4, 2014.
International Preliminary Report on Patentability for International Application No. PCT/US2013/040404, "Nuclear Transport Modulators and Uses Thereof"; Date of Issuance of the Report: Nov. 11, 2014.
International Search Report and the Written Opinion of the International Searching Authority for International Application No. PCT/US2012/021406, "Olefin-Containing Nuclear Transport Modulators and Uses Thereof" dated Apr. 30, 2012.
International Search Report and the Written Opinion of the International Searching Authority for International Application No. PCT/US2012/049470, "Maleimide Compounds and Methods of Treatment," dated Feb. 13, 2013.
International Search Report and the Written Opinion of the International Searching Authority for International Application No. PCT/US2013/040404, "Nuclear Transport Modulators and Uses Thereof"; dated Nov. 18, 2013.
International Search Report and the Written Opinion of the International Searching Authority, or the Declaration for International Application No. PCT/US2014/027136 "Exo Olefin-Containing Nuclear Transport Modulators and Uses Thereof"; dated Jul. 11, 2014.
International Search Report and the Written Opinion of the International Searching Authority, or the Declaration for International Application No. PCT/US2014/029322 "Methods of Promoting Wound Healing Using CRM1 Inhibitors"; dated May 28.
International Search Report and the Written Opinion of the International Searching Authority, or the Declaration for International Application No. PCT/US2014/043479 "Nuclear Transport Modulators and Uses Thereof"; dated Sep. 17, 2014.
International Search Report and the Written Opinion of the International Searching Authority, or the Declaration for International Application No. PCT/US2014/043484 "Nuclear Transport Modulators and Uses Thereof"; dated Sep. 2, 2014.
International Search Report and Written Opinion for International Application No. PCT/US2015/045395 dated Jan. 12, 2016.
International Search Report and Written Opinion for International Application No. PCT/US2016/069492 dated Feb. 16, 2017.
International Search Report and Written Opinion for International Application No. PCT/US2016/069508 dated May 23, 2017.
International Search Report and Written Opinion for International Application No. PCT/US2017/063439 dated Feb. 2, 2018.
International Search Report for International Application No. PCT/US2011/027328, "Nuclear Transport Modulators and Uses Thereof" dated Apr. 29, 2011.
International Search Report for International Application No. PCT/US2012/048319, "Hydrazide Containing Nuclear Transport Modulators and Uses Thereof" dated Nov. 9, 2012.
International Search Report for International Application No. PCT/US2012/048368, "Nuclear Transport Modulators and Uses Thereof" dated Sep. 21, 2012.
Jiang et al., "Palladium-Catalyzed Alkenylation of 1,2,3-Trizoles with Terminal Conjugated Alkenes by Direct C-H Bond Functionalization," Eur J Org Chem, 7:1227-30 (2010).
Karyagin, A. Yu., Reagents for addressed modification of biopolymers, Russian Chemical Bulletin, 2000, 49(3):540-5.

(56) References Cited

OTHER PUBLICATIONS

Karyopharm Therapeutics, "Karyopharm Presents Data Demonstrating the Potential of Nuclear Export Protein Exportin 1 (XPO1) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].
Kau, T.R. et al., "A chemical genetic screen identifies inhibitors of regulated nuclear export of a Forkhead transcription factor in Pten-deficient tumor cells", Cancer Cell, pp. 463-476 (2003).
Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).
Lain, S. et al., "Accumulating active p53 in the nucleus by inhibition of nuclear export: a novel strategy to promote the p53 tumor suppressor function", Exp Cell Res. 253: 315-324 (1999).
Lain, S. et al., "An inhibitor of nuclear export activates the p53 response and induces the localization of HDM2 and p53 to U1A-positive nuclear bodies associated with the PODs", Exp Cell Res. 248:457-472 (1999).
Lala, P.K. et al., "Role of nitric oxide in tumor progression: Lessons from experimental tumors", Cancer and Metastasis Reviews, 17: 91-106 (1998).
Lapalombella, R. et al., "Selective Inhibitors of nuclear exports show that CRM1/XPO1 is a target in chronic lymphocytic leukemia", Blood, 120(23): 4621-4634 (Nov. 29, 2012).
Li, a. et al., "Upregulation of CRM1 Relates to Neuronal Apoptosis after Traumatic Brain Injury in Adult Rats", J Mol Neurosci, 51(1):208-218 (2013).
Maekawa et al., "Efficient Formation of a Triazole Ring Via Novel Ring-Opening Reaction of (z)-2-Methyl-4-arylmethylene-5(4H)-Oxazolones with Hydrazides," Heterocycles, 75(12): 2959-2971 (2008).
Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-8 (2008).
Marelli et al., "Tumor targeting via integrin ligands," Frontiers in Oncology, 3(222):1-12 (2013).
Miskolci et al., "TNFα release from peripheral blood leukocytes depends on a CRM1-mediated nuclear export," Biochemical and Biophysical Research Communications, 351:354-360 (2006).
Modzelewska-Banachiewicz, B. et al., "Synthesis and biological activity of (Z) and (E) isomers of 3-(3,4-diaryl-1,2,4-triazole-5-yl)prop-2-enoic acid" Monatsh Chem. 140:439-444 (2009).
Modzelewska-Banachiewicz, B. et al., "Synthesis and biological activity of new derivatives of 3-(3,4-diaryl-1,2,4-triazole-5-yl)propenoic acid" European Journal of Medicinal Chemistry, 39:873-877 (2004).
Monecke, T. et al., "Crystal Structure of the Nuclear Export Receptor CRM1 in Complex with Snurportin1 and RanGTP", Science, 324:1087-1091 (2009).
Morales et al., "Mechanical Particle-Size Reduction Techniques, Formulating Poorly Water Soluble Dugs," AAPS Advances in Pharmaceutical Sciences Series, 133-170 (2012).
Morissette et al., "High-throughput crystallization: polymorphs, salts, co-crystals and solvates of pharmaceutical solids," Adv Drug Deliv Rev, 56(3):275-300 (2004).
Muller, P.A.J. et al., "Nuclear-Cytosolic Transport of COMMD1 Regulates NF-κB and HIF-1 Activity", Traffic, 10:514-527 (2009).
Mutka et al., "Identification of Nuclear Export Inhibitors with Potent Anticancer Activity in Vivo," Cancer Research, 69(2): 510-517 (2009).
Mutka, S. et al., "Nuclear export inhibitors (NEIs) as novel cancer therapeutics", 98th AACr Ann. Mtg., 2 pgs (Apr. 14-18, 2007) (Poster).
Nagase, The Practice of Medicinal Chemistry, Chapter 13. Conversion of Molecules Based on Equivalent Substitution, vol. 1, Technomics Inc., 1998, 253.
Nair, V., "Thermally induced skeletal rearrangement in a triazepine," J Heterocyclic Chem, 12(1):183-4 (1975).
Nakahara, J. et al., "Abnormal expression of TIP30 and arrested nucleocytoplasmic transport within oligodendrocyte precursor cells in multiple sclerosis", Journal of Clinical Investigation, 119(1):169-181 (2009).
Nautiyal et al., "Distinct functions for RIP140 in development, inflammation, and metabolism," Trends in Endocrinology and Metabolism, 24(9):451-459 (2013).
Noske, A., et al., "Expression of the Nuclear Export Protein Chromosomal Region Maintenance/Exportin 1/Xpo1 is a Prognostic Factor in Human Ovarian Cancer", Cancer, 112(8):1733-1743 (2008).
Orsted et al., "Basic principles of wound healing," Wound Care Canada, 9(2): 4-12 (2011).
Patani, G.A., et al., "Bioisosterism: A Rational Approach in Drug Design", Chem Rev, 96:3147-3176 (1996).
Procopiou et al., "Inhibitors of Cholesterol Biosynthesis. 2. 3,5-Dihydroxy-7-(N-pyrrolyl)-6-heptenoates, a Novel Series of HMG-CoA Reductase Inhibitors," J Med Chem, 36(23): 3658-3662 (1993).
Quan, M.L. et al., "Design and Synthesis of Isoxazoline Derivatives as Factor Xa Inhibitors", J. Med. Chem. 42: 2760-2773 (1999).
Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (2009).
Registry(STN)[online], Jan. 23, 2008, CAS registered No. 1000508-38-2, 1 page.
Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).
Sanchez, V. et al., "Nuclear Export of the Human Cytomegalovirus Tegument Protein pp65 Requires Cyclin-Dependent Kinase Activity and the Crm1 Exporter", Journal of Virology, 81(21):11730-11736 (2007).
Shaoyong, Ke. et al., "Research Advance of Acylhydrazine Derivatives with Biological Activities", Chinese Journal of Organic Chemistry 30(12):1820-1830 (2010).
Shasheva, "Reactions of Hydroxyphenyl-Substituted 1,2,4-Triazoles with Electrophilic Reagents", Russian Journal of General Chemistry, 79(10): 2234-2243 (2009).
Sorokin, A.V. et al., "Nucleocytoplasmic Transport of Proteins", Biochemistry Moscow, 72(13):1439-1457 (2007).
Storey et al., "Solid State Characterization of Pharmaceuticals," Blackwell Publishing, (2011).
Sun Q., et al., "Nuclear export inhibition through covalent conjugation and hydrolysis of Leptomycin B by CRM1", Proc Nat Acad Sci, 110(4): 1303-1308 (2013).
Tai et al., "CRM1 inhibition induces tumor cell cytotoxicity and impairs osteoclastogenesis in multiple myeloma: molecular mechanisms and therapeutic implications," Leukemia, 28:155-165 (2014).
Tamir et al., "KPT-350, a Selective Inhibitor of Nuclear Export (SINE) Compound, Shows Efficacy in the Mouse Pilocapine Model of Temporal Lobe Epilepsy," Journal of Neurological Sciences, 381: 87-88 (2017).
Terry, L.J. et al., "Crossing the Nuclear Envelope: Hierarchical Regulation of Nucleocytoplasmic Transport", Science, 318:1412-1416 (2007).
Van der Watt, P.J. et al., "The Karyopherin proteins, Crm1 and Karyopherin β1, are overexpressed in cervical cancer and are critical for cancer cell survival and proliferation", Int. J. Cancer, 124:1829-1840 (2009).
Van Neck et al., "Inhibition of the CRM1-mediated nucleocytoplasmic transport by N-azolylacrylates: Structure-activity relationship and mechanism of action", Bioorganic & Medicinal Chemistry 16:9487-9497 (2008).
Walsh, Jr., M.D., et al., Exportin 1 Inhibition Attenuates Nuclear Factor-κB-Dependent Gene Expression, Shock, 29(2):160-166 (2008).
Wang et al., "Mathematical modeling in cancer drug discovery," Drug Discovery Today, 19(2):145-150 (2014).

(56) References Cited

OTHER PUBLICATIONS

Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (2008).

Written Opinion of the International Searching Authority for International Application No. PCT/US2011/027328, "Nuclear Transport Modulators and Uses Thereof" (4823.1003-002) dated Apr. 29, 2011, 8 pages.

Written Opinion of the International Searching Authority for International Application No. PCT/US2012/048319, "Hydrazide Containing Nuclear Transport Modulators and Uses Thereof" (4823.1002-006) dated Nov. 9, 2012, 9 pages.

Written Opinion of the International Searching Authority for International Application No. PCT/US2012/048368, "Nuclear Transport Modulators and Uses Thereof" (4823.1001-002) dated Sep. 21, 2012, 11 pages.

Yao, Y., et al., "The expression of CRM1 is associated with prognosis in human osteosarcoma", Oncology Reports, 21:229-235 (2009).

Yonemochi, "Physicochemical Properties for Amorphous Pharmaceuticals and their Stability," Cryobiol and Cryotechnol 51(1):25-30 (2005).

Zheng et al., "KPT-330 inhibitor of XPO1-mediated nuclear export has anti-proliferative activity in hepatocellular carcinoma," Cancer Chemother Pharmacol, 74:487-495 (2014).

Zimmerman, T.L. et al., "Nuclear Export of Retinoid X Receptor a in Response to Interleukin-1β-mediated Cell Signaling Roles for JNK and Ser260", The Journal of Biological Chemistry, 281(22):15434-15440 (2006).

Notice of Allowance for Application No. 16/203,181 dated Oct. 3, 2019.

Notice of Allowance for U.S. Appl. No. 13/891,044 "Nuclear Transport Modulators and Uses Thereof", dated Apr. 7, 2015.

Notice of Allowance for U.S. Appl. No. 13/931,372 "Nuclear Transport Modulators and Uses Thereof", dated Sep. 7, 2016.

Notice of Allowance for U.S. Appl. No. 14/235,342 "Nuclear Transport Modulators and Uses Thereof", dated Apr. 25, 2016.

Notice of Allowance for U.S. Appl. No. 14/735,853 "Nuclear Transport Modulators and Uses Thereof", dated Aug. 4, 2015.

Notice of Allowance for U.S. Appl. No. 14/747,394 "Nuclear Transport Modulators and Uses Thereof", dated Aug. 30, 2017.

Notice of Allowance for U.S. Appl. No. 14/900,469 "Nuclear Transport Modulators and Uses Thereof", dated Apr. 18, 2017.

Notice of Allowance for U.S. Appl. No. 14/940,310 "Hydrazide Containing Nuclear Transport Modulators and Uses Thereof", dated Mar. 14, 2017.

Notice of Allowance for U.S. Appl. No. 14/989,377 "Nuclear Transport Modulators and Uses Thereof", dated Oct. 28, 2016.

Notice of Allowance for U.S. Appl. No. 15/413,889 "Nuclear Transport Modulators and Uses Thereof", dated Apr. 10, 2018.

Requirement for Restriction/Election for U.S. Appl. No. 13/041,377 "Nuclear Transport Modulators and Uses Thereof", dated Jul. 5, 2012.

Requirement for Restriction/Election for U.S. Appl. No. 13/350,864 "Olefin Containing Nuclear Transport Modulators and Uses Thereof", dated Dec. 19, 2013.

Requirement for Restriction/Election for U.S. Appl. No. 13/931,372 "Nuclear Transport Modulators and Uses Thereof", dated May 22, 2014.

Requirement for Restriction/Election for U.S. Appl. No. 14/235,342 "Nuclear Transport Modulators and Uses Thereof", dated Jun. 9, 2015.

Requirement for Restriction/Election for U.S. Appl. No. 14/777,302 "Methods of Promoting Wound Healing Using CRM1 Inhibitors", dated Sep. 22, 2016.

Requirement for Restriction/Election for U.S. Appl. No. 15/217,514 "Nuclear Transport Modulators and Uses Thereof", dated Aug. 8, 2017.

Chemical Abstract Registry Nos. 1181485-58-4; 1100108-00-6 (2009).

\* cited by examiner

| Size (μm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (μm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.724 | 0.00 |
| 0.832 | 0.00 |
| 0.955 | 0.00 |

| Size (μm) | Vol Under% |
|---|---|
| 1.096 | 0.00 |
| 1.259 | 0.00 |
| 1.445 | 0.00 |
| 1.660 | 0.02 |
| 1.905 | 0.20 |
| 2.188 | 0.60 |
| 2.512 | 1.25 |
| 2.884 | 2.21 |
| 3.311 | 3.54 |
| 3.802 | 5.31 |
| 4.365 | 7.61 |
| 5.012 | 10.49 |
| 5.754 | 14.00 |
| 6.607 | 18.15 |
| 7.586 | 22.94 |
| 8.710 | 28.29 |
| 10.000 | 34.10 |

| Size (μm) | Vol Under% |
|---|---|
| 11.482 | 40.21 |
| 13.183 | 46.45 |
| 15.136 | 52.61 |
| 17.378 | 58.48 |
| 19.953 | 63.89 |
| 22.909 | 68.72 |
| 26.303 | 72.88 |
| 30.200 | 76.39 |
| 34.674 | 79.30 |
| 39.811 | 81.72 |
| 45.709 | 83.78 |
| 52.481 | 85.62 |
| 60.256 | 87.35 |
| 69.183 | 89.02 |
| 79.433 | 90.66 |
| 91.201 | 92.21 |
| 104.713 | 93.60 |

| Size (μm) | Vol Under% |
|---|---|
| 120.226 | 94.74 |
| 138.038 | 95.61 |
| 158.489 | 96.21 |
| 181.970 | 96.60 |
| 208.930 | 96.90 |
| 239.883 | 97.21 |
| 275.423 | 97.58 |
| 316.228 | 98.04 |
| 363.078 | 98.57 |
| 416.869 | 99.12 |
| 478.630 | 99.59 |
| 549.541 | 99.92 |
| 630.957 | 100.00 |
| 724.436 | 100.00 |
| 831.764 | 100.00 |
| 954.993 | 100.00 |
| 1096.478 | 100.00 |

| Size (μm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | 100.00 |
| | |

FIG. 5B

| Size (μm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (μm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.734 | 0.00 |
| 0.832 | 0.00 |
| 0.955 | 0.00 |

| Size (μm) | Vol Under% |
|---|---|
| 1.096 | 0.00 |
| 1.259 | 0.00 |
| 1.445 | 0.05 |
| 1.660 | 0.81 |
| 1.905 | 2.19 |
| 2.188 | 4.30 |
| 2.512 | 7.15 |
| 2.884 | 10.66 |
| 3.311 | 14.70 |
| 3.802 | 19.12 |
| 4.365 | 23.78 |
| 5.012 | 29.52 |
| 5.754 | 33.20 |
| 6.607 | 37.69 |
| 7.586 | 41.88 |
| 8.710 | 45.68 |
| 10.000 | 49.07 |

| Size (μm) | Vol Under% |
|---|---|
| 11.482 | 52.03 |
| 13.183 | 54.59 |
| 15.136 | 56.81 |
| 17.378 | 58.77 |
| 19.953 | 60.57 |
| 22.909 | 62.32 |
| 26.303 | 64.13 |
| 30.200 | 66.13 |
| 34.674 | 68.38 |
| 39.811 | 70.95 |
| 45.709 | 73.84 |
| 52.481 | 77.02 |
| 60.256 | 80.40 |
| 69.183 | 83.85 |
| 79.433 | 87.22 |
| 91.201 | 90.34 |
| 104.713 | 93.07 |

| Size (μm) | Vol Under% |
|---|---|
| 120.226 | 95.30 |
| 138.038 | 97.00 |
| 158.489 | 98.17 |
| 181.970 | 98.88 |
| 208.930 | 99.25 |
| 239.883 | 99.41 |
| 275.423 | 99.47 |
| 316.228 | 99.52 |
| 363.078 | 99.62 |
| 416.869 | 99.77 |
| 478.630 | 99.94 |
| 549.541 | 100.00 |
| 630.957 | 100.00 |
| 724.436 | 100.00 |
| 831.764 | 100.00 |
| 954.993 | 100.00 |
| 1096.478 | 100.00 |

| Size (μm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | |

| Size (μm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (μm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.734 | 0.00 |
| 0.832 | 0.00 |
| 0.955 | 0.00 |

| Size (μm) | Vol Under% |
|---|---|
| 1.096 | 0.00 |
| 1.259 | 0.00 |
| 1.445 | 0.00 |
| 1.660 | 0.00 |
| 1.905 | 0.00 |
| 2.188 | 0.08 |
| 2.512 | 0.26 |
| 2.884 | 0.61 |
| 3.311 | 1.18 |
| 3.802 | 2.09 |
| 4.365 | 3.43 |
| 5.012 | 5.30 |
| 5.754 | 7.78 |
| 6.607 | 10.93 |
| 7.586 | 14.77 |
| 8.710 | 19.30 |
| 10.000 | 24.42 |

| Size (μm) | Vol Under% |
|---|---|
| 11.482 | 30.01 |
| 13.183 | 35.90 |
| 15.136 | 41.89 |
| 17.378 | 47.76 |
| 19.953 | 53.35 |
| 22.909 | 58.52 |
| 26.303 | 63.18 |
| 30.200 | 67.32 |
| 34.674 | 70.99 |
| 39.811 | 74.29 |
| 45.709 | 77.33 |
| 52.481 | 80.21 |
| 60.256 | 83.00 |
| 69.183 | 85.72 |
| 79.433 | 88.36 |
| 91.201 | 90.84 |
| 104.713 | 93.05 |

| Size (μm) | Vol Under% |
|---|---|
| 120.226 | 94.91 |
| 138.038 | 96.34 |
| 158.489 | 97.35 |
| 181.970 | 98.01 |
| 208.930 | 98.43 |
| 239.883 | 98.70 |
| 275.423 | 98.91 |
| 316.228 | 99.13 |
| 363.078 | 99.36 |
| 416.869 | 99.59 |
| 478.630 | 99.81 |
| 549.541 | 99.95 |
| 630.957 | 100.00 |
| 724.436 | 100.00 |
| 831.764 | 100.00 |
| 954.993 | 100.00 |
| 1096.478 | 100.00 |

| Size (μm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.884 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | 100.00 |

FIG. 5H

| Size (μm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (μm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.734 | 0.00 |
| 0.832 | 0.00 |
| 0.955 | 0.00 |

| Size (μm) | Vol Under% |
|---|---|
| 1.096 | 0.00 |
| 1.259 | 0.00 |
| 1.445 | 0.00 |
| 1.660 | 0.00 |
| 1.905 | 0.00 |
| 2.188 | 0.19 |
| 2.512 | 0.62 |
| 2.884 | 1.39 |
| 3.311 | 2.61 |
| 3.802 | 4.41 |
| 4.365 | 6.90 |
| 5.012 | 10.18 |
| 5.754 | 14.34 |
| 6.607 | 19.43 |
| 7.586 | 25.42 |
| 8.710 | 32.23 |
| 10.000 | 39.70 |

| Size (μm) | Vol Under% |
|---|---|
| 11.482 | 47.59 |
| 13.183 | 55.60 |
| 15.136 | 63.44 |
| 17.378 | 70.81 |
| 19.953 | 77.45 |
| 22.909 | 83.17 |
| 26.303 | 87.89 |
| 30.200 | 91.59 |
| 34.674 | 94.34 |
| 39.811 | 96.26 |
| 45.709 | 97.53 |
| 52.481 | 98.31 |
| 60.256 | 98.75 |
| 69.183 | 98.98 |
| 79.433 | 99.09 |
| 91.201 | 99.15 |
| 104.713 | 99.20 |

| Size (μm) | Vol Under% |
|---|---|
| 120.226 | 99.24 |
| 138.038 | 99.29 |
| 158.489 | 99.35 |
| 181.970 | 99.42 |
| 208.930 | 99.49 |
| 239.883 | 99.57 |
| 275.423 | 99.66 |
| 316.228 | 99.75 |
| 363.078 | 99.84 |
| 416.869 | 99.92 |
| 478.630 | 99.99 |
| 549.541 | 100.00 |
| 630.957 | 100.00 |
| 724.436 | 100.00 |
| 831.764 | 100.00 |
| 954.993 | 100.00 |
| 1096.478 | 100.00 |

| Size (μm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | 100.00 |

FIG. 5J

| Size (μm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.724 | 0.00 |
| 0.832 | 0.00 |
| 0.955 | 0.00 |
| 1.096 | 0.00 |
| 1.259 | 0.00 |
| 1.445 | 0.00 |
| 1.660 | 0.00 |
| 1.905 | 0.00 |
| 2.188 | 0.08 |
| 2.512 | 0.28 |
| 2.884 | 0.66 |
| 3.311 | 1.28 |
| 3.802 | 2.26 |
| 4.365 | 3.72 |
| 5.012 | 5.79 |
| 5.754 | 8.60 |
| 6.607 | 12.30 |
| 7.586 | 16.96 |
| 8.710 | 22.62 |
| 10.000 | 29.20 |
| 11.482 | 36.57 |
| 13.183 | 44.50 |
| 15.136 | 52.68 |
| 17.378 | 60.79 |
| 19.953 | 68.49 |
| 22.909 | 75.48 |
| 26.303 | 81.56 |
| 30.200 | 86.59 |
| 34.674 | 90.56 |
| 39.811 | 93.49 |
| 45.709 | 95.55 |
| 52.481 | 96.89 |
| 60.256 | 97.71 |
| 69.183 | 98.15 |
| 79.433 | 98.38 |
| 91.201 | 98.49 |
| 104.713 | 98.55 |
| 120.226 | 98.61 |
| 138.038 | 98.69 |
| 158.489 | 98.79 |
| 181.970 | 98.92 |
| 208.930 | 99.06 |
| 239.883 | 99.23 |
| 275.423 | 99.40 |
| 316.228 | 99.56 |
| 363.078 | 99.72 |
| 416.869 | 99.87 |
| 478.630 | 99.97 |
| 549.541 | 100.00 |
| 630.957 | 100.00 |
| 724.436 | 100.00 |
| 831.764 | 100.00 |
| 954.993 | 100.00 |
| 1096.478 | 100.00 |
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | |

FIG. 5L

| Size (μm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (μm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.724 | 0.00 |
| 0.832 | 0.00 |
| 0.955 | 0.00 |

| Size (μm) | Vol Under% |
|---|---|
| 1.096 | 0.00 |
| 1.259 | 0.00 |
| 1.445 | 0.00 |
| 1.660 | 0.00 |
| 1.905 | 0.00 |
| 2.188 | 0.10 |
| 2.512 | 0.24 |
| 2.884 | 0.44 |
| 3.311 | 0.72 |
| 3.802 | 1.15 |
| 4.365 | 1.82 |
| 5.012 | 2.87 |
| 5.754 | 4.43 |
| 6.607 | 6.68 |
| 7.586 | 9.75 |
| 8.710 | 13.76 |
| 10.000 | 18.74 |

| Size (μm) | Vol Under% |
|---|---|
| 11.482 | 24.70 |
| 13.183 | 31.53 |
| 15.136 | 39.04 |
| 17.378 | 47.00 |
| 19.953 | 55.10 |
| 22.909 | 63.03 |
| 26.303 | 70.49 |
| 30.200 | 77.24 |
| 34.674 | 83.10 |
| 39.811 | 87.97 |
| 45.709 | 91.84 |
| 52.481 | 94.76 |
| 60.256 | 96.85 |
| 69.183 | 98.24 |
| 79.433 | 99.11 |
| 91.201 | 99.60 |
| 104.713 | 99.85 |

| Size (μm) | Vol Under% |
|---|---|
| 120.226 | 99.96 |
| 138.038 | 100.00 |
| 158.489 | 100.00 |
| 181.970 | 100.00 |
| 208.930 | 100.00 |
| 239.883 | 100.00 |
| 275.423 | 100.00 |
| 316.228 | 100.00 |
| 363.078 | 100.00 |
| 416.869 | 100.00 |
| 478.630 | 100.00 |
| 549.541 | 100.00 |
| 630.957 | 100.00 |
| 724.436 | 100.00 |
| 831.764 | 100.00 |
| 954.993 | 100.00 |
| 1096.478 | 100.00 |

| Size (μm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | 100.00 |

| Size (µm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (µm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.724 | 0.00 |
| 0.832 | 0.04 |
| 0.955 | 0.13 |

| Size (µm) | Vol Under% |
|---|---|
| 1.096 | 0.23 |
| 1.259 | 0.31 |
| 1.445 | 0.38 |
| 1.660 | 0.45 |
| 1.905 | 0.53 |
| 2.188 | 0.65 |
| 2.512 | 0.78 |
| 2.884 | 0.91 |
| 3.311 | 1.04 |
| 3.802 | 1.19 |
| 4.365 | 1.42 |
| 5.012 | 1.82 |
| 5.754 | 2.50 |
| 6.607 | 3.60 |
| 7.586 | 5.27 |
| 8.710 | 7.66 |
| 10.000 | 10.87 |

| Size (µm) | Vol Under% |
|---|---|
| 11.482 | 15.00 |
| 13.183 | 20.02 |
| 15.136 | 25.89 |
| 17.378 | 32.45 |
| 19.953 | 39.47 |
| 22.909 | 46.69 |
| 26.303 | 53.86 |
| 30.200 | 60.73 |
| 34.674 | 67.12 |
| 39.811 | 72.93 |
| 45.709 | 78.12 |
| 52.481 | 82.72 |
| 60.256 | 86.75 |
| 69.183 | 90.25 |
| 79.433 | 93.25 |
| 91.201 | 95.71 |
| 104.713 | 97.63 |

| Size (µm) | Vol Under% |
|---|---|
| 120.226 | 98.97 |
| 138.038 | 99.78 |
| 158.489 | 100.00 |
| 181.970 | 100.00 |
| 208.930 | 100.00 |
| 239.883 | 100.00 |
| 275.423 | 100.00 |
| 316.228 | 100.00 |
| 363.078 | 100.00 |
| 416.869 | 100.00 |
| 478.630 | 100.00 |
| 549.541 | 100.00 |
| 630.957 | 100.00 |
| 724.436 | 100.00 |
| 831.764 | 100.00 |
| 954.993 | 100.00 |
| 1096.478 | 100.00 |

| Size (µm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | 100.00 |
| | |

*FIG. 5N*

| Size (µm) | Vol Under% |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |

| Size (µm) | Vol Under% |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.724 | 0.00 |
| 0.832 | 0.00 |
| 0.955 | 0.00 |

| Size (µm) | Vol Under% |
|---|---|
| 1.096 | 0.00 |
| 1.259 | 0.00 |
| 1.445 | 0.00 |
| 1.660 | 0.00 |
| 1.905 | 0.00 |
| 2.188 | 0.00 |
| 2.512 | 0.00 |
| 2.884 | 0.00 |
| 3.311 | 0.00 |
| 3.802 | 0.00 |
| 4.365 | 0.00 |
| 5.012 | 0.06 |
| 5.754 | 0.26 |
| 6.607 | 0.76 |
| 7.586 | 1.67 |
| 8.710 | 3.17 |
| 10.000 | 5.44 |

| Size (µm) | Vol Under% |
|---|---|
| 11.482 | 8.62 |
| 13.183 | 12.81 |
| 15.136 | 18.06 |
| 17.378 | 24.28 |
| 19.953 | 31.35 |
| 22.909 | 39.04 |
| 26.303 | 47.07 |
| 30.200 | 55.13 |
| 34.674 | 62.95 |
| 39.811 | 70.26 |
| 45.709 | 76.90 |
| 52.481 | 82.73 |
| 60.256 | 87.70 |
| 69.183 | 91.79 |
| 79.433 | 95.02 |
| 91.201 | 97.43 |
| 104.713 | 99.06 |

| Size (µm) | Vol Under% |
|---|---|
| 120.226 | 99.87 |
| 138.038 | 100.00 |
| 158.489 | 100.00 |
| 181.970 | 100.00 |
| 208.930 | 100.00 |
| 239.883 | 100.00 |
| 275.423 | 100.00 |
| 316.228 | 100.00 |
| 363.078 | 100.00 |
| 416.869 | 100.00 |
| 478.630 | 100.00 |
| 549.541 | 100.00 |
| 630.957 | 100.00 |
| 724.436 | 100.00 |
| 831.764 | 100.00 |
| 954.993 | 100.00 |
| 1096.478 | 100.00 |

| Size (µm) | Vol Under% |
|---|---|
| 1258.925 | 100.00 |
| 1445.440 | 100.00 |
| 1659.587 | 100.00 |
| 1905.461 | 100.00 |
| 2187.762 | 100.00 |
| 2511.886 | 100.00 |
| 2884.032 | 100.00 |
| 3311.311 | 100.00 |
| 3801.984 | 100.00 |
| 4365.158 | 100.00 |
| 5011.872 | 100.00 |
| 5754.399 | 100.00 |
| 6606.934 | 100.00 |
| 7585.776 | 100.00 |
| 8709.636 | 100.00 |
| 10000.000 | 100.00 |

*FIG. 5P*

POLYMORPHS OF SELINEXOR

RELATED APPLICATIONS

This application is a continuation of U.S. application Ser. No. 15/503,319, filed on Feb. 10, 2017, which is the U.S. National Stage of International Application No. PCT/US2015/045395, filed on Aug. 14, 2015, published in English, which claims the benefit of U.S. Provisional Application No. 62/038,069 filed on Aug. 15, 2014. The entire teachings of the above application are incorporated herein by reference.

BACKGROUND OF THE INVENTION

International Publication No. WO 2013/019548 describes a series of compounds that are indicated to have inhibitory activity against chromosomal region maintenance 1 (CRM1, also referred to as exportin 1 or XPO1) and to be useful in the treatment of disorders associated with CRM1 activity, such as cancer. (Z)-3-(3-(3,5-bis(trifluoromethyl)phenyl)-1H-1,2,4-triazol-1-yl)-N'-(pyrazin-2-yl)acrylohydrazide (also referred to as selinexor) is one of the compounds disclosed in International Publication No. WO 2013/019548. Selinexor has the chemical structure shown in Structural Formula I:

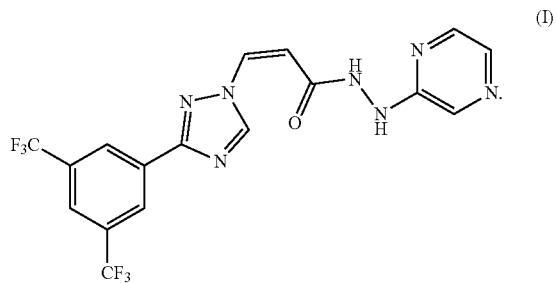 [SMILES: O=C(/C=C\n1cnc(-c2cc(C(F)(F)F)cc(C(F)(F)F)c2)n1)NNc1cnccn1]

(I)

The solid form of a compound can be important in the formulation of pharmaceutical compositions. For example, crystalline and amorphous forms of a compound can have different physical properties (e.g., stability, dissolution rate, density, etc.) relating to their suitability for use in pharmaceutical compositions. The difference in physical properties can also affect a crystalline or amorphous form's usefulness, for example, as an intermediate in the synthesis of a form suitable for use in pharmaceutical compositions.

There is a need for crystalline forms of Selinexor that are thermodynamically stable and suitable for use in pharmaceutical compositions (e.g., are readily dissolvable, exhibit good flow properties, have desirable particle size distribution and good chemical stability). There is a further need for crystalline forms of Selinexor having physical properties that enable the manufacture of selinexor for use in pharmaceutical compositions in high yield and high purity.

SUMMARY OF THE INVENTION

The present invention relates to crystalline forms of Selinexor, and compositions comprising crystalline forms of Selinexor described herein. Selinexor has the chemical structure shown in Structural Formula I:

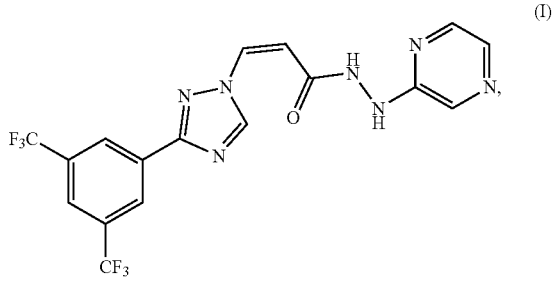 [SMILES: O=C(/C=C\n1cnc(-c2cc(C(F)(F)F)cc(C(F)(F)F)c2)n1)NNc1cnccn1]

(I)

and is also referred to herein as KGB.

In one embodiment, a single crystalline form of a compound represented by Structural Formula I is provided, wherein the single crystalline form is Form A. In this embodiment, single crystalline Form A is characterized by at least three X-ray powder diffraction peaks at 2θ angles selected from 4.4°, 19.9°, 21.3° and 22.0°. Single crystalline Form A is the thermodynamically most stable of the forms described herein.

In another embodiment, a single crystalline form of a compound represented by Structural Formula I is provided, wherein the single crystalline form is Form D. In this embodiment, single crystalline Form D is characterized by at least three X-ray powder diffraction peaks at 2θ angles selected from 3.7°, 7.3°, 10.9°, 18.3° and 21.9°. Form D is particularly advantageous when used as an intermediate in the preparation of From A because it creates a unique ability for high yield and purity of Selinexor.

In yet another embodiment, a single crystalline form of a compound represented by Structural Formula I is provided, wherein the single crystalline form is Form B. In this embodiment, single crystalline Form B is characterized by at least three X-ray powder diffraction peaks at 2θ angles selected from 9.4°, 11.1°, 16.5°, 18.3° and 18.8°.

In another embodiment, a single crystalline form of a compound represented by Structural Formula I is provided, wherein the single crystalline form is Form C. In this embodiment, single crystalline Form C is characterized by at least three X-ray powder diffraction peaks at 2θ angles selected from 3.7°, 11.2°, 12.1° and 18.6°.

Another embodiment is a composition comprising particles of a single crystalline form of a compound represented by Structural Formula I, wherein the single crystalline form is Form A. Single crystalline Form A is characterized by at least three X-ray powder diffraction peaks at 2θ angles selected from 4.4°, 19.9°, 21.3° and 22.0°. In some embodiments, the particles of the composition have a unimodal particle size distribution characterized by a d(0.9) of 100 microns or less. In some embodiments, the particles of the composition have a unimodal particle size distribution characterized by a d(0.9) of 70 microns or less.

Another embodiment is a pharmaceutical composition comprising a composition comprising particles of single crystalline Form A of a compound of Structural Formula I and a pharmaceutically acceptable carrier. Single crystalline Form A is characterized by at least three X-ray powder diffraction peaks at 2θ angles selected from 4.4°, 19.9°, 21.3° and 22.0°. In some embodiments, the particles of the composition have a unimodal particle size distribution characterized by a d(0.9) of 100 microns or less. In some embodiments, the particles of the composition have a unimodal particle size distribution characterized by a d(0.9) of 70 microns or less.

The pharmaceutical composition can be used in a method for treating a disorder associated with CRM1 activity (e.g., cancer) or for promoting wound healing in a subject in need thereof. The methods comprise administering to a subject in need thereof a therapeutically effective amount of the pharmaceutical composition.

One embodiment is a method of preparing a single crystalline form of a compound represented by Structural Formula I, wherein the single crystalline form is Form A. Single crystalline Form A is characterized by at least three X-ray powder diffraction peaks at 2θ angles selected from 4.4°, 19.9°, 21.3° and 22.0°. The method comprises suspending single crystalline Form B, C or D of the compound of Structural Formula I, or a mixture comprising two or more of the single crystalline forms, in isopropanol or a mixture of isopropanol and water to form a slurry; heating the slurry to a temperature less than or equal to about 70° C. to form a second slurry or a solution; cooling the second slurry or the solution and adding water to the second slurry or the solution, thereby forming solid particles of crystalline Form A of the compound of Structural Formula I; and isolating the solid particles of crystalline Form A. Single crystalline Form D is characterized by at least three X-ray powder diffraction peaks at 2θ angles selected from 3.7°, 7.3°, 10.9°, 18.3° and 21.9°. Single crystalline Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°.

Another embodiment is a method of preparing a single crystalline form of a compound represented by Structural Formula I, wherein the single crystalline form is Form A. Single crystalline Form A is characterized by at least three X-ray powder diffraction peaks at 2θ angles selected from 4.4°, 19.9°, 21.3° and 22.0°. The method comprises suspending single crystalline Form B, C or D of the compound of Structural Formula I, or a mixture comprising two or more of the single crystalline forms, in isopropanol or a mixture of isopropanol and water to form a slurry; heating the slurry to a temperature less than or equal to about 70° C. to form a second slurry or a solution; adding water to the second slurry or the solution and cooling the second slurry or the solution, thereby forming solid particles of crystalline Form A of the compound of Structural Formula I; and isolating the solid particles of crystalline Form A. Single crystalline Form D is characterized by at least three X-ray powder diffraction peaks at 2θ angles selected from 3.7°, 7.3°, 10.9°, 18.3° and 21.9°. Single crystalline Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°.

Another embodiment is a method of preparing a single crystalline form of a compound represented by Structural Formula I, wherein the single crystalline form is Form A. Single crystalline Form A is characterized by at least three X-ray powder diffraction peaks at 2θ angles selected from 4.4°, 19.9°, 21.3° and 22.0°. The method comprises heating single crystalline Form B, C or D of the compound of Structural Formula I or a mixture comprising two or more crystalline forms of the compound of Structural Formula I and inducing formation of solid particles of crystalline Form A; or maturing single crystalline Form B, C or D of the compound of Structural Formula I, or a mixture comprising two or more crystalline forms of the compound of Structural Formula I in a solvent system and inducing formation of solid particles of crystalline Form A; or drying single crystalline Form B, C or D of the compound of Structural Formula I, or a mixture comprising two or more crystalline forms of the compound of Structural Formula I, thereby forming solid particles of crystalline Form A; or any combination of the foregoing; and isolating the solid particles of crystalline Form A.

Yet another embodiment is a method of preparing a single crystalline form of a compound represented by Structural Formula I wherein the single crystalline form is Form D. Single crystalline Form D is characterized by at least three X-ray powder diffraction peaks at 2θ angles selected from 3.7°, 7.3°, 10.9°, 18.3° and 21.9°. The method comprises dissolving the compound of Structural Formula I in a solvent system comprising acetonitrile; inducing formation of solid particles of crystalline Form D of the compound of Structural Formula I; and isolating the solid particles of crystalline Form D.

In another embodiment, a method of preparing a compound of Structural Formula I is provided. The method comprises combining a trialkylamine, 2-methyltetrahydrofuran, a compound of Structural Formula II:

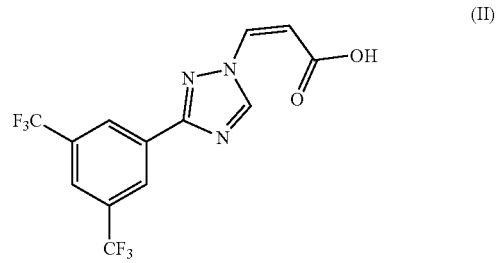 [SMILES: O=C(O)/C=C\n1cnc(-c2cc(C(F)(F)F)cc(C(F)(F)F)c2)n1]

(II)

and a compound of Structural Formula III:

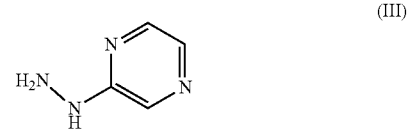

(III)

to form a reaction mixture;
cooling the reaction mixture to from about −80° C. to about 0° C.; treating the reaction mixture with propylphosphonic anhydride to provide a mixture comprising the compound of Structural Formula I; and isolating the compound of Structural Formula I from the mixture.

Another embodiment is a method of preparing a single crystalline form of a compound represented by Structural Formula I wherein the single crystalline form is Form A. Single crystalline Form A is characterized by at least three X-ray powder diffraction peaks at 2θ angles selected from 4.4°, 19.9°, 21.3° and 22.0°. The method comprises combining a trialkylamine, 2-methyltetrahydrofuran, a compound of Structural Formula II and a compound of Structural Formula III to form a reaction mixture. The reaction mixture is cooled to from about −80° C. to about 0° C. and treated with propylphosphonic anhydride to provide a mixture comprising the compound of Structural Formula I. The compound of Structural Formula I is isolated from the reaction mixture and the isolated compound of Structural Formula I is dissolved in a solvent system comprising acetonitrile. To obtain single crystalline Form D of the compound of Structural Formula I, formation of solid particles of single crystalline Form D of the compound of Structural Formula I is induced and the solid particles of crystalline Form D are isolated. In some instances, in addition to solid particles of crystalline Form D, solid particles of crystalline Form B or C of Structural Formula I or a mixture comprising two or more crystalline Forms B, C or D of the compound of Structural Formula I is isolated. Single crystalline Form D or in some instances single crystalline Form B or C of Structural Formula I or a mixture comprising two or more crystalline Forms B, C or D of the compound of Structural Formula I is heated and formation of solid particles of crystalline Form A is induced; or single crystalline Form D or in some instances single crystalline Form B or C of Structural Formula I or a mixture comprising two or more crystalline Forms B, C or D of the compound of Structural Formula I is matured in a solvent and formation of solid particles of crystalline Form A is induced; or single crystalline Form D or in some instances single crystalline Form B or C of Structural Formula I or a mixture comprising two or more crystalline Forms B, C or D of the compound of Structural Formula I is dried, thereby forming solid particles of crystalline Form A; or any combination of the foregoing. The solid particles of crystalline Form A are isolated. Single crystalline Form D is characterized by at least three X-ray powder diffraction peaks at 2θ angles selected from 3.7°, 7.3°, 10.9°, 18.3° and 21.9°. Single crystalline Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°.

Another embodiment provides a method for preparing a single crystalline form of a compound represented by Structural Formula I wherein the single crystalline form is Form A. Single crystalline Form A is characterized by at least three X-ray powder diffraction peaks at 2θ angles selected from 4.4°, 19.9°, 21.3° and 22.0°. The method comprises combining a trialkylamine, 2-methyltetrahydrofuran, a compound of Structural Formula II and a compound of Structural Formula III to form a reaction mixture. The reaction mixture is cooled to from about −80° C. to about 0° C. and treated with propylphosphonic anhydride to provide a mixture comprising the compound of Structural Formula I. The compound of Structural Formula I is isolated from the mixture and dissolved in a solvent system comprising acetonitrile. To obtain single crystalline Form D of the compound of Structural Formula I, formation of solid particles of crystalline Form D are induced and the solid particles of crystalline Form D are isolated. In some instances, in addition to solid particles of crystalline Form D, solid particles of crystalline Form B or C of Structural Formula I or a mixture comprising two or more crystalline Forms B, C or D of the compound of Structural Formula I is isolated Single crystalline Form D, or single crystalline Form B or C of the compound of Structural Formula I or a mixture comprising two or more crystalline forms of the compound of Structural Formula I, is suspended in isopropanol or a mixture of isopropanol and water to form a slurry and the slurry is heated to a temperature less than or equal to about 70° C. to form a second slurry or a solution. The second slurry or the solution is allowed to cool and water is added, thereby forming solid particles of crystalline Form A of the compound of Structural Formula I. The solid particles of crystalline Form A are isolated. Single crystalline Form D is characterized by at least three X-ray powder diffraction peaks at 2θ angles selected from 3.7°, 7.3°, 10.9°, 18.3° and 21.9°. Single crystalline Form B is characterized by at least three X-ray powder diffraction peaks at 2θ angles selected from 9.4°, 11.1°, 16.5°, 18.3° and 18.8°. Single crystalline Form B is characterized by at least three X-ray diffraction peaks at 2θ angles selected from 3.7°, 11.2°, 12.1° and 18.6°. In an alternative embodiment to the foregoing, water is added to the second slurry or solution and then cooling is performed.

Single crystalline Form D described herein can be prepared, in accordance with the methods disclosed herein, in high yield and purity. The exceptional purity of single crystalline Form D can be translated into highly pure single crystalline Form A for pharmaceutical use, while the high yield of single crystalline Form D can be translated into a method for making single crystalline Form A that is amenable to use on a manufacturing scale (e.g., achieving high yield and purity). Using the procedures for converting single crystalline Form D (or Form B or C) into single crystalline Form A described herein, single crystalline Form A can be isolated as a composition comprising particles of single crystalline Form A having a particle size distribution ready for formulation as a pharmaceutical composition (e.g., oral bioavailability despite not being readily dissolvable and/or exhibiting good flow properties). In addition, of the four forms described herein, Form A is the thermodynamically most stable form.

BRIEF DESCRIPTION OF THE FIGURES

The foregoing will be apparent from the following more particular description of example embodiments of the invention.

FIG. 5A and FIG. 5B shows the particle size distribution of Selinexor particles from Lot No. 1305365, prepared according to the procedure described in Example 1.

FIG. 5C and FIG. 5D show the particle size distribution of Selinexor particles from Lot No. 1341-AK-109-2, prepared according to the procedure described in Example 2.

FIG. 5E and FIG. 5F show the particle size distribution of Selinexor particles from Lot No. PC-14-005, prepared according to the procedure described in Example 3.

FIG. 5G and FIG. 5H show the particle size distribution of Selinexor particles from Lot No. 1339-BS-142-1, prepared according to the procedure described in Example 5.

FIG. 5I and FIG. 5J show the particle size distribution of Selinexor particles from Lot No. 1339-BS-142-2, prepared according to the procedure described in Example 5.

FIG. 5K and FIG. 5L show the particle size distribution of Selinexor particles from Lot No. PC-14-008, prepared according to the procedure described in Example 5.

FIG. 5M and FIG. 5N show the particle size distribution of Selinexor particles from Lot No. PC-14-009, prepared according to the procedure described in Example 4.

FIG. 5O and FIG. 5P show the particle size distribution of Selinexor particles from Lot No. 1405463, prepared according to the procedure described in Example 6.

DETAILED DESCRIPTION OF THE INVENTION

Figure 1A:
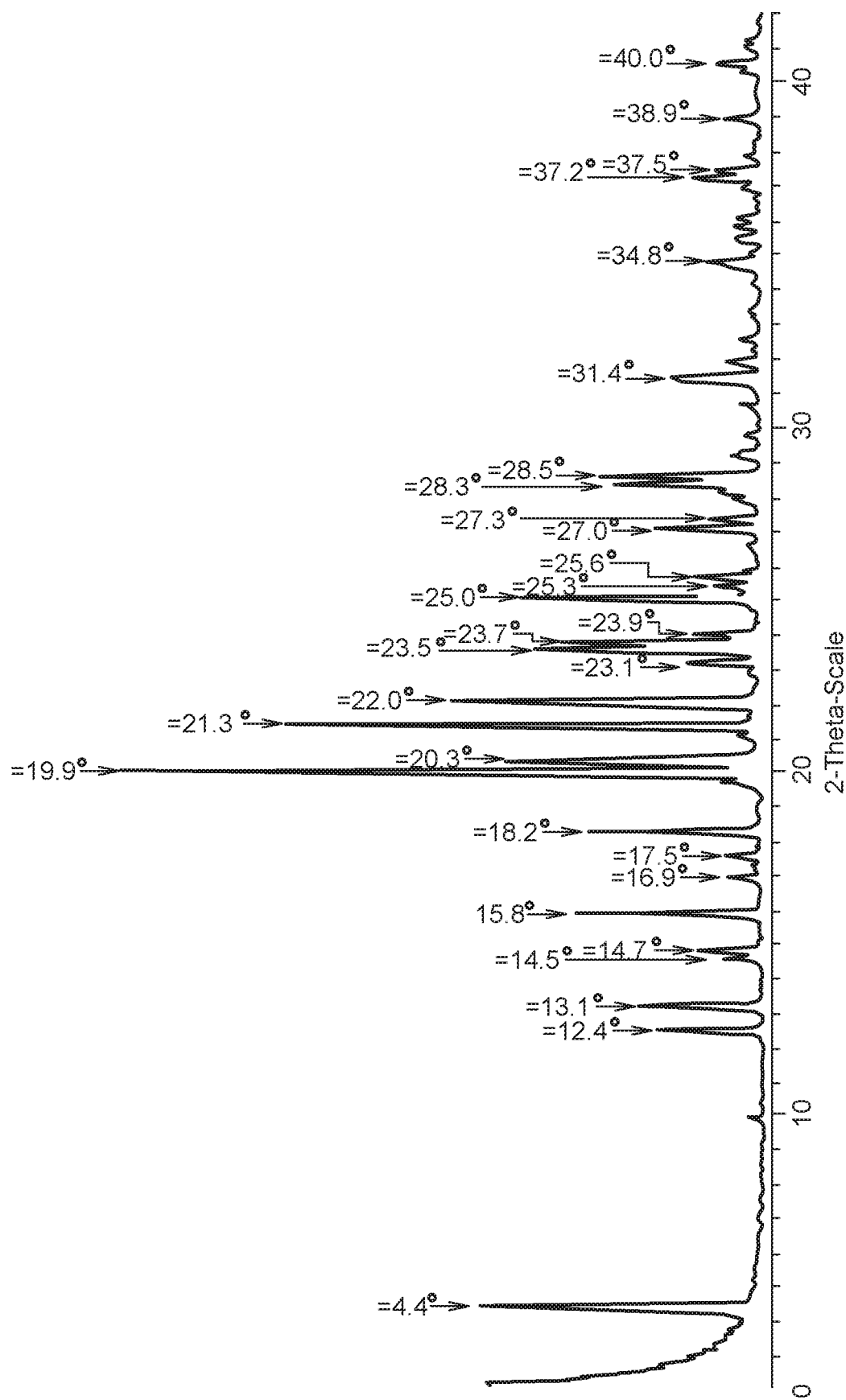
FIG. 1A is an X-ray powder diffraction (XRPD) pattern of Structural Formula I—Form A, prepared in accordance with the procedure described in Example 1.

A description of example embodiments of the invention follows.

Crystalline Forms of Selinexor

Provided herein are crystalline forms of the compound of Structural Formula I, designated crystalline Form A, crystalline Form B, crystalline Form C and crystalline Form D.

"Crystalline," as used herein, refers to a homogeneous solid formed by a repeating, three-dimensional pattern of atoms, ions or molecules (e.g., an anhydrous molecule or a salt thereof, solvate thereof, or combination of the foregoing) having fixed distances between constituent parts. The unit cell is the simplest repeating unit in this pattern.

A crystalline form provided herein can be a single crystalline form or can comprise a mixture of two or more different crystalline forms. For example, in some embodiments, crystalline Forms A, B, C and D of a compound of Structural Formula I are provided as single crystalline forms (i.e., single crystalline Form A, single crystalline Form B, single crystalline Form C, single crystalline Form D). Alternatively, a crystalline form can comprise a mixture of two or more crystalline forms of a compound of Structural Formula I (e.g., a mixture of two or more of crystalline Forms A, B, C and D, specifically, two or more of crystalline Forms B, C and D).

"Single crystalline form," as used herein, refers to a single crystal of a crystalline solid or a plurality of crystals of a crystalline solid wherein each of the plurality of crystals has the same crystal form.

The crystalline forms (e.g., the single crystalline forms) provided herein can be identified on the basis of characteristic peaks in an X-ray powder diffraction (XRPD) analysis. XRPD is a scientific technique that measures the X-rays, neutrons or electrons scattered by a powder or microcrystalline material as a function of scattering angle. XRPD can be used to identify and characterize crystalline solids, as the diffraction pattern produced by a particular solid is typically distinctive to that solid and can be used as a "fingerprint" to identify that solid. For example, an XRPD pattern or diffractogram (e.g., a pattern or diffractogram produced by a sample, such as an unknown sample) that is substantially in accordance with a reference XRPD pattern or diffractogram can be used to determine the identity between the sample material and the reference material. Both the position and the relative intensity of the peaks in an XRPD diffractogram are indicative of the particular phase and identity of a material.

FIGS. 1A, 2A, 3A and 4A show XRPD patterns of various single crystalline forms described herein. An XRPD pattern that is "substantially in accordance" with one or more figures herein showing an XRPD pattern or diffractogram is an XRPD pattern that would be considered by one skilled in the art to represent the same single crystalline form of the compound of Structural Formula I as the sample of the compound of Structural Formula I that provided the XRPD pattern of one or more figures provided herein. Thus, an XRPD pattern that is substantially in accordance may be identical to that of one of the figures or, more likely, may be somewhat different from one or more of the figures. An XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern of the sample and the corresponding XRPD pattern disclosed herein.

It is to be understood that any 2θ angle specified herein, with the exception of the 2θ angles specified in the Figures or the Exemplification, means the specified value ±0.2°. For example, when a described embodiment or a claim specifies a 2θ of 4.4°, this is to be understood to mean 4.4°±0.2°, that is, a 2θ angle of from 4.2° to 4.6°.

The crystalline forms (e.g., the single crystalline forms) provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition.

TGA is a method of thermal gravimetric analysis in which changes in physical and chemical properties of a material are measured as a function of increasing temperature (with constant heating rate) or as a function of time (with constant temperature and/or constant mass loss). TGA can provide information about physical phenomena, such as second-order phase transitions, or about chemical phenomena, such as desolvation and/or decomposition.

Figure 1B:
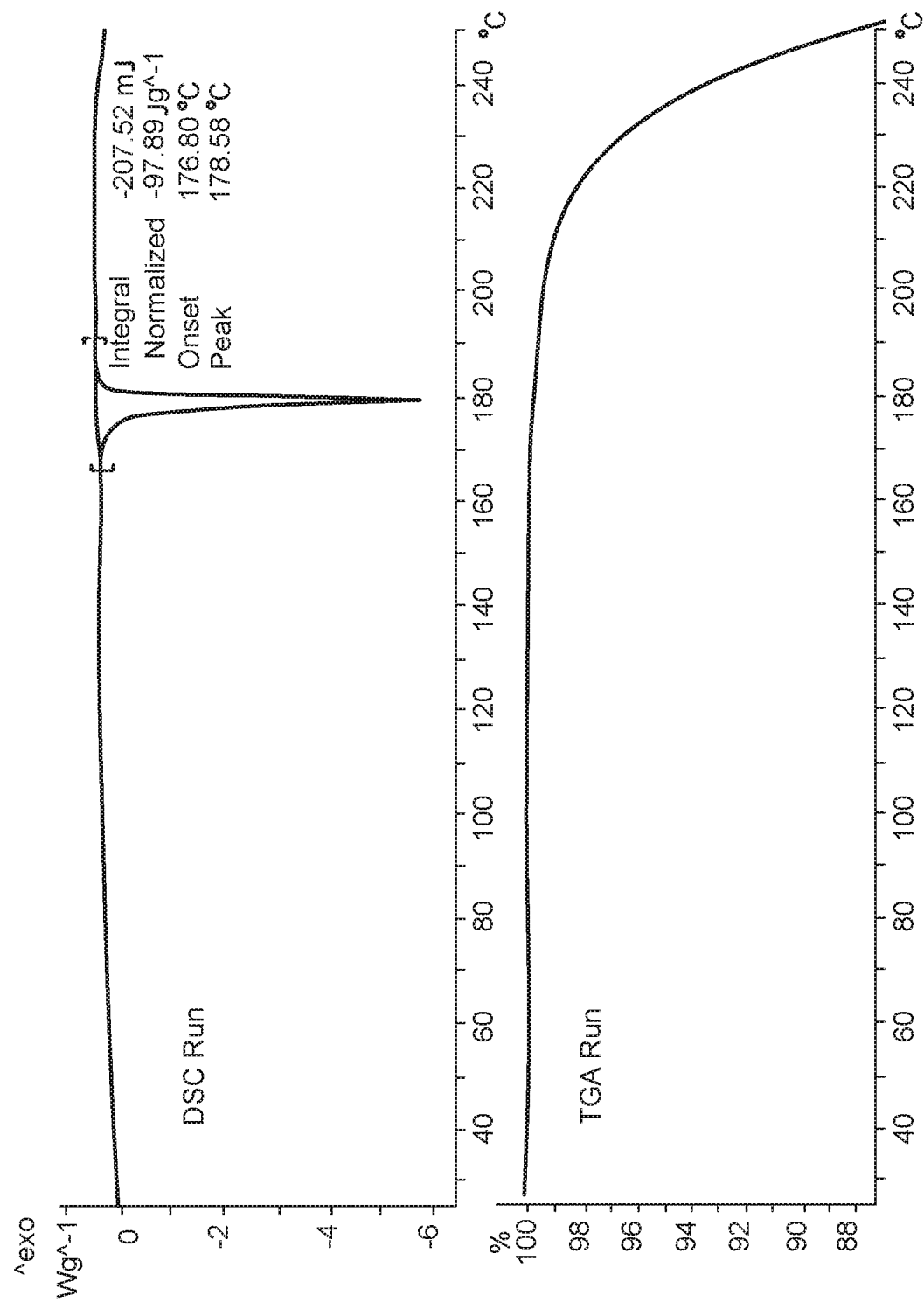
FIG. 1B is a differential scanning calorimetry (DSC) thermogram and a thermogravimetric analysis (TGA) thermogram of Structural Formula I—Form A, prepared in accordance with the procedure described in Example 1.
Figure 2A:
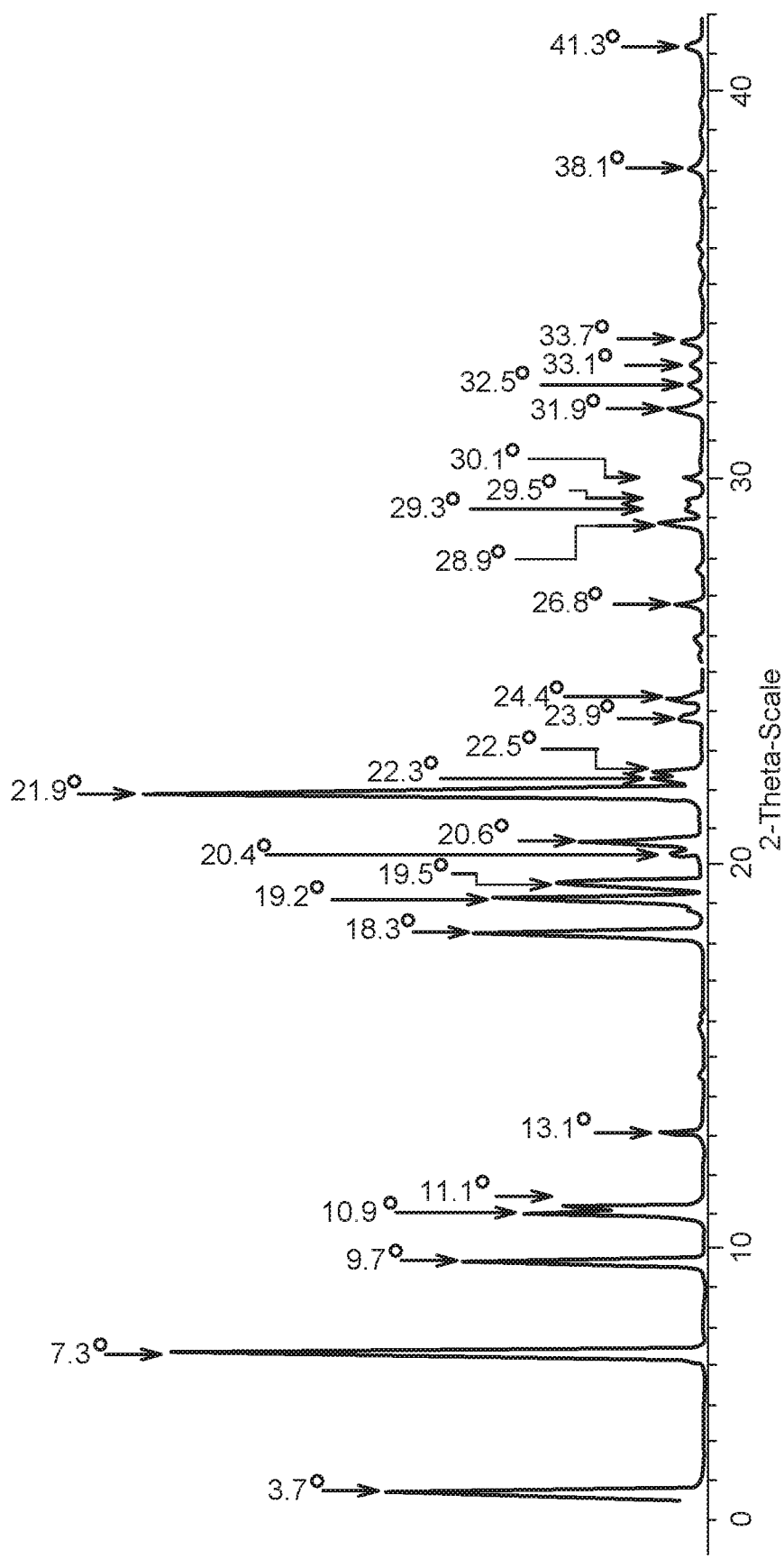
FIG. 2A is an XRPD pattern of an acetonitrile solvate of Structural Formula I—Form D, prepared in accordance with the procedure described in Example 7.
Figure 2B:
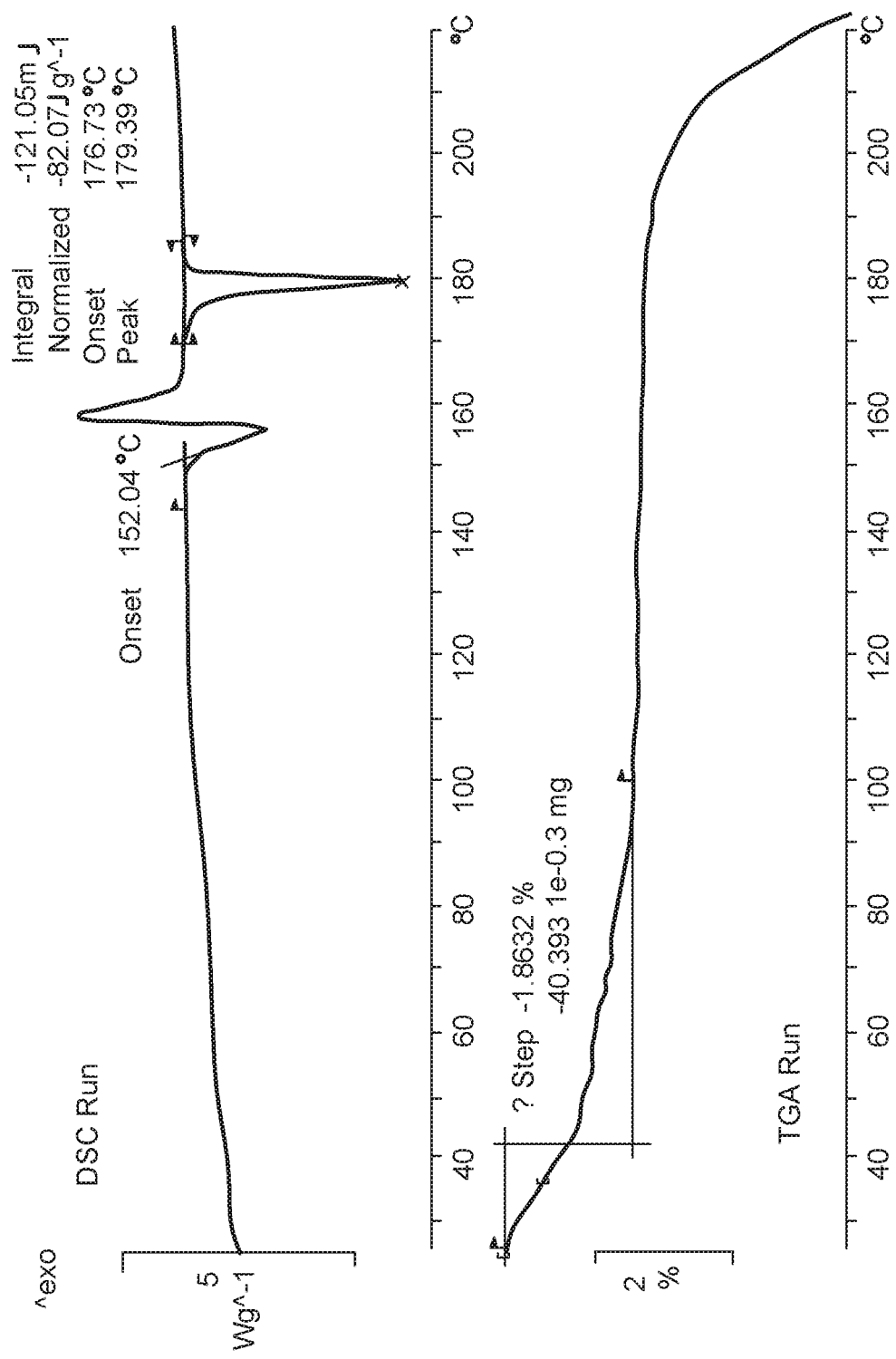
FIG. 2B is a DSC thermogram and a TGA thermogram of Structural Formula I—Form D, prepared in accordance with the procedure described in Example 7.

FIGS. 1B, 2B, 3B and 4B show DSC thermograms of various single crystalline forms described herein. FIGS. 1B and 2B show TGA thermograms of various single crystalline forms described herein. A DSC or TGA thermogram that is "substantially in accordance" with one or more figures herein showing a DSC or TGA thermogram is a DSC or TGA thermogram that would be considered by one skilled in the art to represent the same single crystalline form of the compound of Structural Formula I as the sample of the compound of Structural Formula I that provided the DSC or TGA thermogram of one or more figures provided herein.

It is to be understood that any temperature associated with DSC or TGA specified herein, with the exception of the DSC or TGA temperatures in the Figures or Exemplification, means the specified value ±5° C. or less. For example, when an embodiment or a claim specifies an endothermic peak at about 179° C., this is to be understood to mean 179° C.±5° C. or less, that is a temperature of from 174° C. to 184° C.

In preferred embodiments, a DSC or TGA temperature is the specified value ±3° C., in more preferred embodiments, ±2° C.

In a first embodiment, a single crystalline form of a compound represented by Structural Formula I is provided, wherein the single crystalline form is Form A. Form A is the thermodynamically most stable of the four forms described herein. Single crystalline Form A can be characterized by at least three X-ray powder diffraction peaks at 2θ angles selected from 4.4°, 19.9°, 21.3° and 22.0°. In a particular embodiment, single crystalline Form A is characterized by X-ray powder diffraction peaks at 2θ angles of 4.4°, 19.9°, 21.3° and 22.0°, more particularly, by X-ray powder diffraction peaks at 2θ angles of 4.4°, 19.9°, 20.3°, 21.3°, 22.0°, 23.5° and 25.0°, yet more particularly, by X-ray powder diffraction peaks at 2θ angles of 4.4°, 13.1°, 15.8°, 18.2°, 19.9°, 20.3°, 21.3°, 22.0°, 23.5°, 23.7°, 25.0°, 27.0°, 28.3° and 28.5°. In some embodiments, single crystalline Form A is characterized by an X-ray powder diffraction pattern substantially in accordance with that depicted in FIG. 1A.

Single crystalline Form A can be further characterized by a DSC thermogram comprising an endothermic peak at about 179° C. In some embodiments, single crystalline Form A is further characterized by a DSC thermogram and/or a TGA thermogram substantially in accordance with that depicted in FIG. 1B.

In a second embodiment, a single crystalline form of a compound represented by Structural Formula I is provided, wherein the single crystalline form is Form D. Single crystalline Form D can be characterized by at least three X-ray powder diffraction peaks at 2θ angles selected from 3.7°, 7.3°, 10.9°, 18.3° and 21.9°. In a particular embodiment, single crystalline Form D is characterized by X-ray powder diffraction peaks at 2θ angles of 3.7°, 7.3°, 10.9°, 18.3° and 21.9°, more particularly, by X-ray powder diffraction peaks at 2θ angles of 3.7°, 7.3°, 9.7°, 10.9°, 18.3°, 19.2° and 21.9°, yet more particularly, by X-ray powder diffraction peaks at 2θ angles of 3.7°, 7.3°, 9.7°, 10.9°, 11.1°, 18.3°, 19.2°, 19.5°, 20.6° and 21.9°. In some embodiments, single crystalline Form D is characterized by an X-ray powder diffraction pattern substantially in accordance with that depicted in FIG. 2A.

Single crystalline Form D can be further characterized by a DSC thermogram and/or a TGA thermogram substantially in accordance with that depicted in FIG. 2B. The DSC thermogram indicates multiple melting and recrystallizing events indicating interconversion of forms.

In some embodiments, single crystalline Form D is in the form of a solvate, for example, an acetonitrile solvate. In some embodiments, the solvate (e.g., acetonitrile solvate) comprises from about 0.5 to about 1.5 molar equivalents of solute (e.g., acetonitrile) per molar equivalent of the compound of Structural Formula I, more particularly, one molar equivalent of solute per molar equivalent of the compound of Structural Formula I.

"Solvate," as used herein, refers to a chemical compound formed by the interaction of a solute (e.g., a compound of Structural Formula I) and one or more solvents (e.g., acetonitrile, water). Thus, "solvate" includes solvates containing a single type of solvent molecule and solvates containing more than one type of solvent molecule (mixed solvates). Typically, the one or more solvents in solvates described herein is an organic solvent or a combination of organic solvents, although water can also form solvates, called hydrates. Exemplary solvates include acetonitrile solvates.

In a third embodiment, a single crystalline form of a compound represented by Structural Formula I is provided, wherein the single crystalline form is Form B. Single crystalline Form B can be characterized by at least three X-ray powder diffraction peaks at 2θ angles selected from 9.4°, 11.1°, 16.5°, 18.3° and 18.8°. In a particular embodiment, single crystalline Form B is characterized by X-ray powder diffraction peaks at 2θ angles of 9.4°, 11.1°, 16.5°, 18.3° and 18.8°, more particularly, by X-ray powder diffraction peaks at 2θ angles of 9.4°, 11.1°, 16.5°, 18.3°, 18.8°, 20.2° and 20.8°, yet more particularly, by X-ray powder diffraction peaks at 2θ angles of 8.1°, 9.4°, 11.1°, 13.8°, 16.5°, 18.3°, 18.8°, 20.2° and 20.8°. In some embodiments, single crystalline Form B is characterized by an X-ray powder diffraction pattern substantially in accordance with that depicted in FIG. 3A.

Figure 3A:
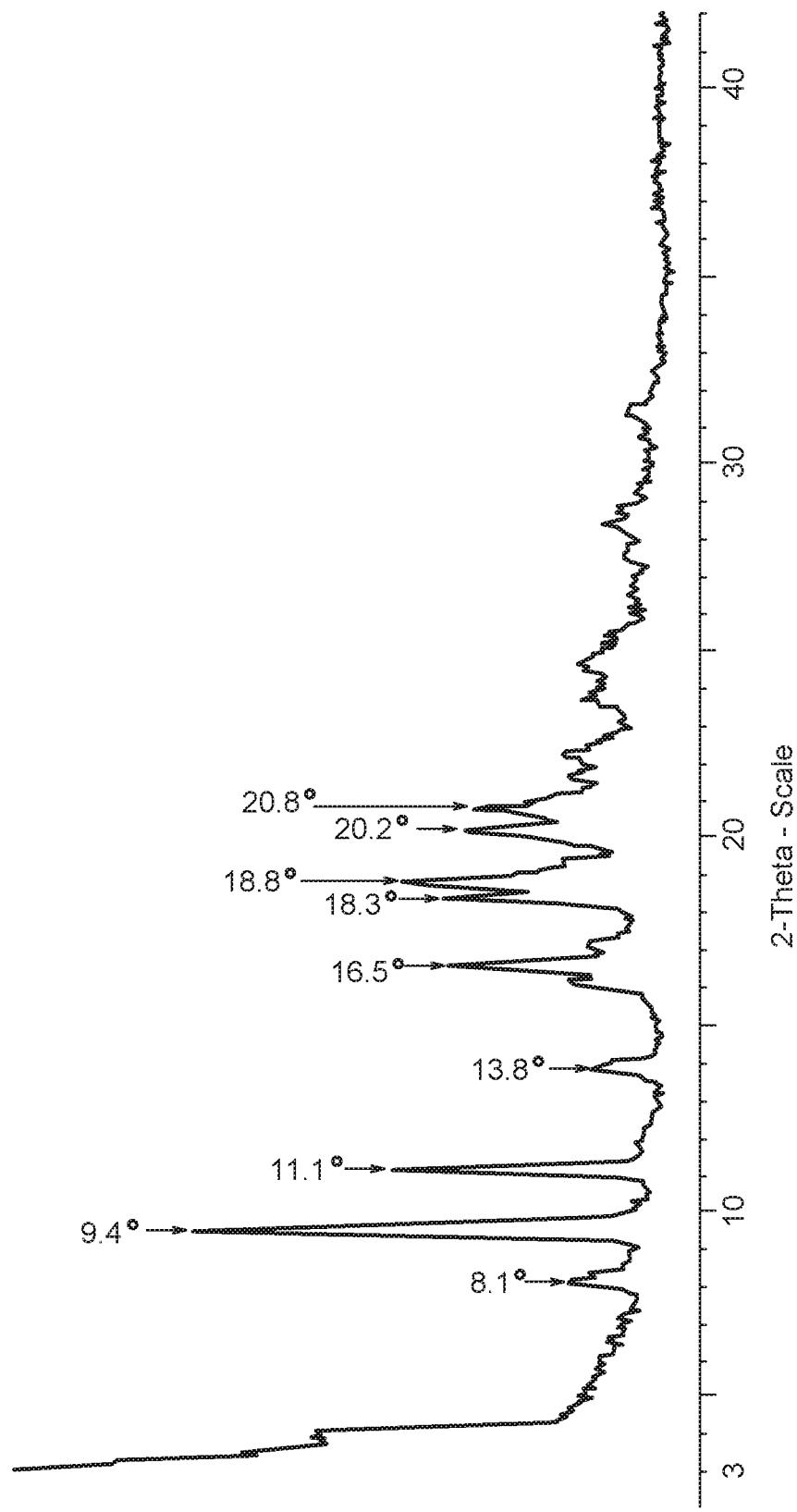
FIG. 3A is an XRPD pattern of Structural Formula I—Form B, prepared in accordance with the procedure described in Example 7.
Figure 3B:
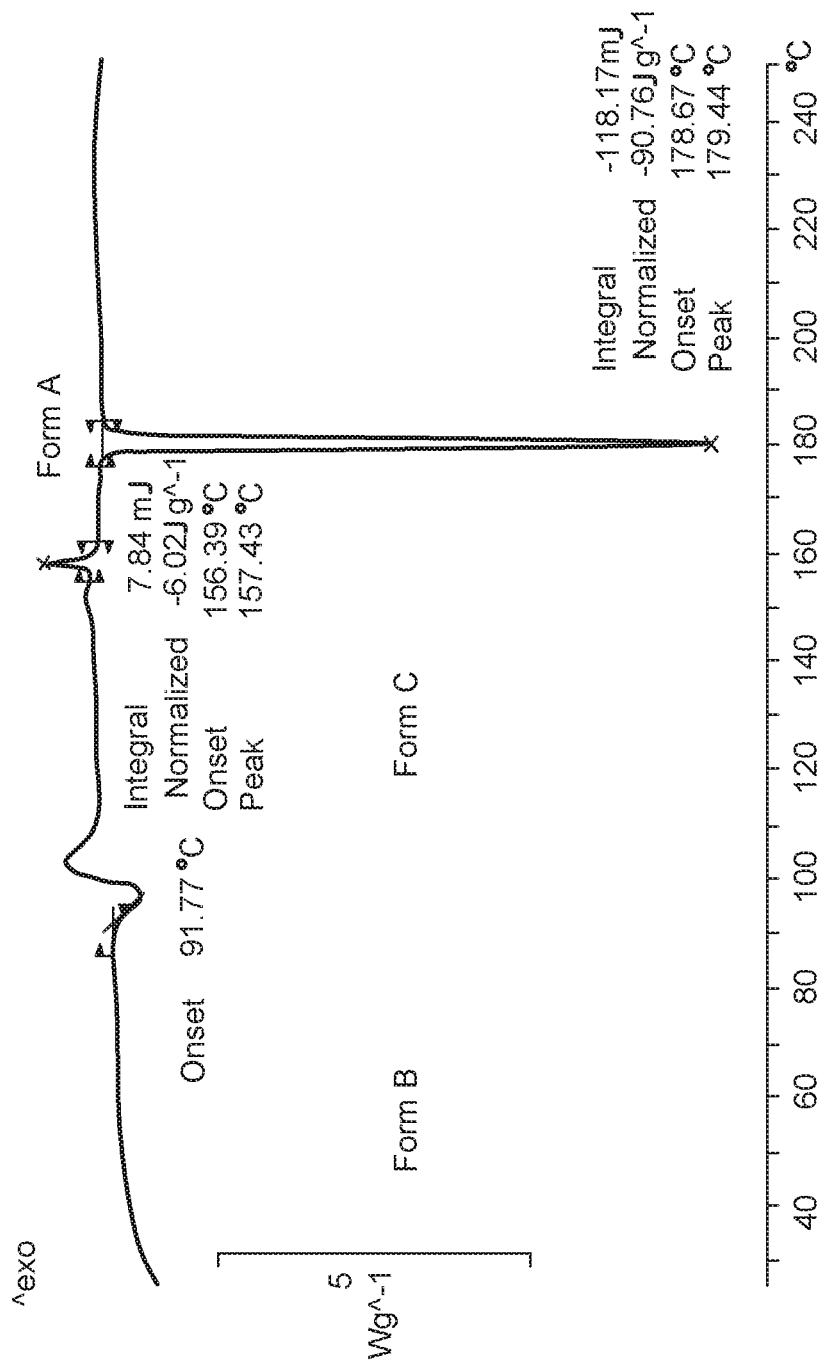
FIG. 3B is a DSC thermogram of Structural Formula I—Form B, prepared in accordance with the procedure described in Example 7.

Single crystalline Form B can be further characterized by a DSC thermogram and/or a TGA thermogram substantially in accordance with that depicted in FIG. 3B. The DSC thermogram indicates multiple melting and recrystallizing events indicating interconversion of forms.

In a fourth embodiment, a single crystalline form of a compound represented by Structural Formula I is provided, wherein the single crystalline form is Form C. Single crystalline Form C can be characterized by at least three X-ray powder diffraction peaks at 2θ angles selected from 3.7°, 11.2°, 12.1° and 18.6°. In a particular embodiment, single crystalline Form C is characterized by X-ray powder diffraction peaks at 2θ angles selected from 3.7°, 11.2°, 12.1° and 18.6°, more particularly, by X-ray powder diffraction peaks at 2θ angles selected from 3.7°, 11.2°, 17.7°, 12.1°, 18.6°, 19.7°, 21.2° and 22.2°. In some embodiments, single crystalline Form C is characterized by an X-ray powder diffraction pattern substantially in accordance with that depicted in FIG. 4A.

Figure 4A:
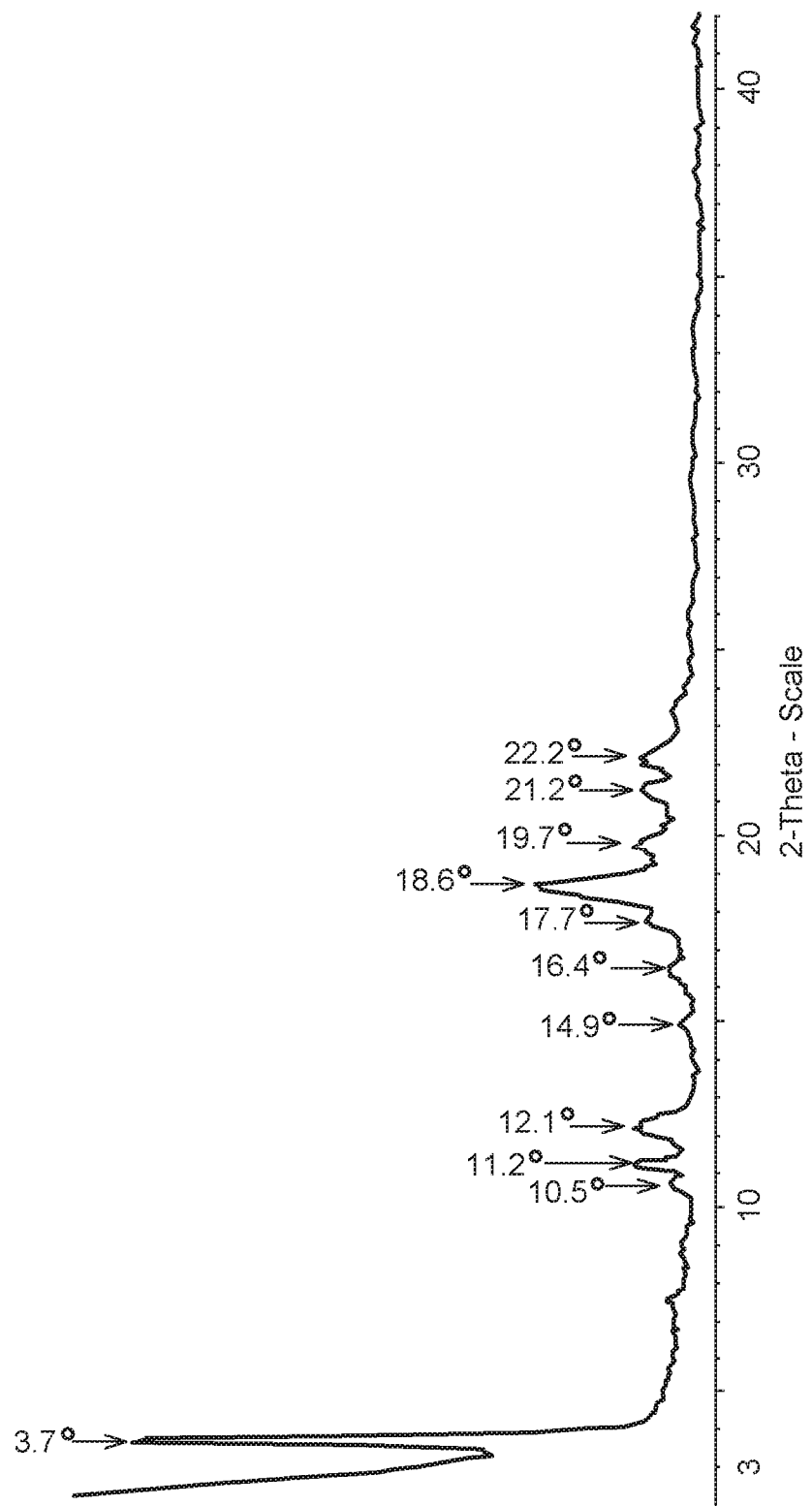
FIG. 4A is an XRPD pattern of Structural Formula I—Form C, prepared in accordance with the procedure described in Example 7.
Figure 4B:
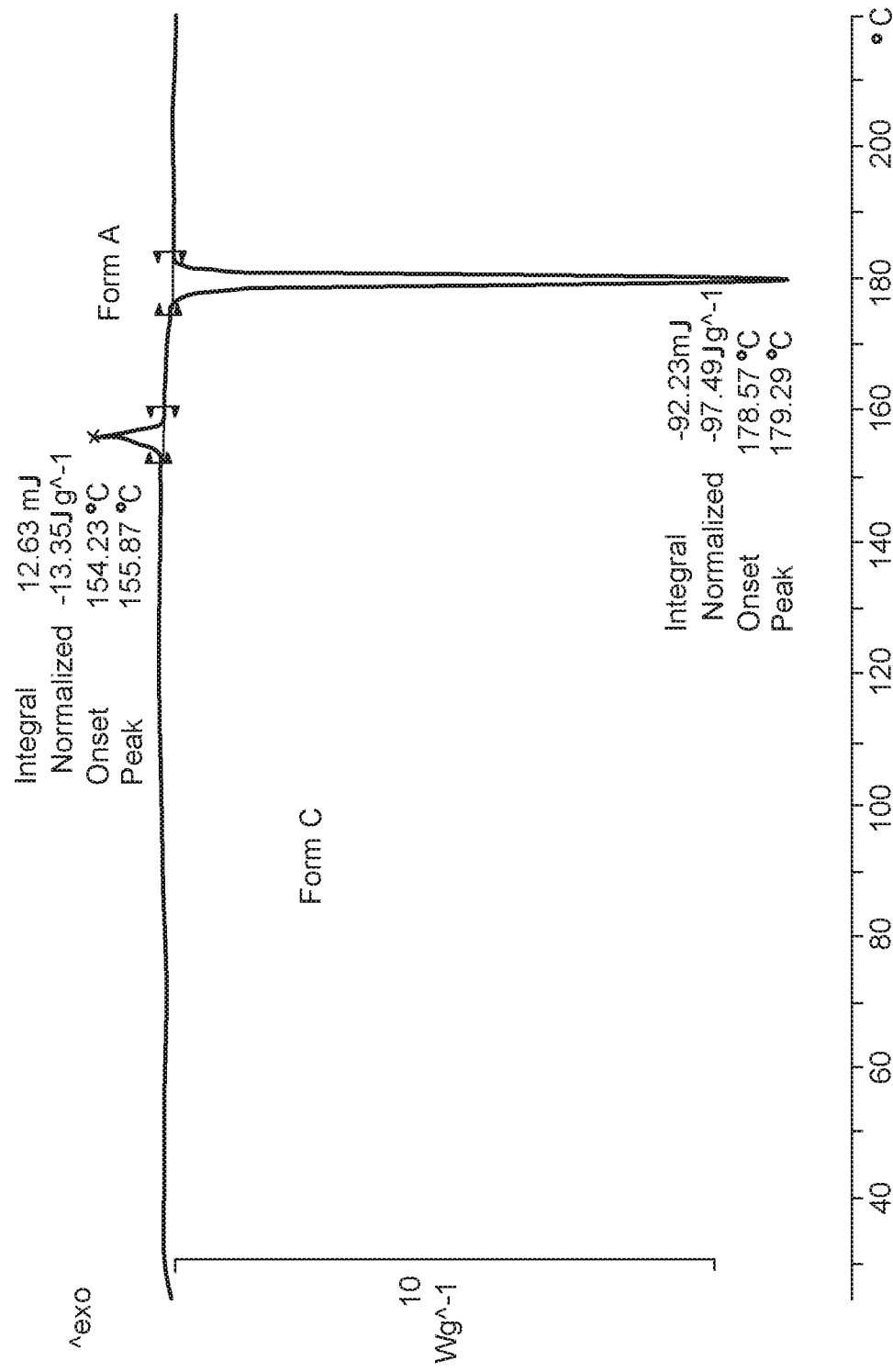
FIG. 4B is a DSC thermogram of Structural Formula I—Form C, prepared in accordance with the procedure described in Example 7.

Single crystalline Form D can be further characterized by a DSC thermogram and/or a TGA thermogram substantially in accordance with that depicted in FIG. 4B. The DSC thermogram indicates multiple melting and recrystallizing events indicating intercoversion of forms.

Compositions

Also provided herein are compositions comprising particles (e.g., solid particles) of a single crystalline form (e.g., Form A, B, C or D) of a compound of Structural Formula I, wherein characteristics and alternative characteristics of the single crystalline form in the composition, including alternative XRPD, DSC and/or TGA characteristics, are as described above with respect to the first through fourth embodiments.

A fifth embodiment is a composition comprising particles (e.g., solid particles) of a single crystalline form of a compound represented by Structural Formula I, wherein the single crystalline form is Form A. Single crystalline Form A is characterized by at least three X-ray powder diffraction peaks at 2θ angles selected from 4.4°, 19.9°, 21.3° and 22.0°. In some embodiments, the particles of the composition have a particle size distribution (e.g., a unimodal particle size distribution) characterized by a d(0.9) of 100 microns or less. In some embodiments, the particles of the composition have a particle size distribution (e.g., a unimodal particle size distribution) characterized by a d(0.9) of 70 microns or less.

"Particle size distribution," as used herein, refers to a list of values or a mathematical function that defines the relative amount, typically by mass or volume, of particles present in a sample according to size. Particle size distribution can be characterized by one or more values, such as d(0.9), d(0.5)

or d(0.1) or a ratio of any of the foregoing, or by the shape of the mathematical function, when graphed. Exemplary shapes of a particle size distribution graph include unimodal, bimodal, normal and Gaussian.

"d(0.9)," as used herein, describes the value of particle size at which 90% of the total volume of particles is comprised of particles no larger than the indicated size. d(0.9) is used interchangeably herein with d90, $d_{90}$ and D90. It is to be understood that any d(0.9) value specified herein, with the exception of the d(0.9) values in the Figures or the Exemplification, means the specified value ±15% or less of the specified value. In preferred embodiments, d(0.9) is the specified value ±10% For example, when an embodiment or a claim specifies a d(0.9) of about 70 microns, this is to be understood to mean 70 microns ±7 microns, that is from 63 microns to 77 microns. In preferred embodiments, d(0.9) is the specified value ±7.5%, more preferably, ±6.5%. Similarly, when an embodiment or a claim specifies a d(0.9) of about 100 microns, this is to be understood for example of the specified value being ±10%, to mean 100 microns ±10 microns, that is from 90 microns to 110 microns.

"d(0.5)," as used herein, describes the value of particle size at which 50% of the total volume of particles is comprised of particles no larger than the indicated size. d(0.5) is typically the median of the particle size distribution. d(0.5) is used interchangeably herein with d50, $d_{50}$ and D50. It is to be understood that any d(0.5) value specified herein, with the exception of the d(0.5) values in the Figures or the Exemplification, means the specified value ±10% or less of the specified value. For example, when an embodiment or a claim specifies a d(0.5) of about 25 microns, this is to be understood to mean 25 microns ±2.5 microns, that is from 22.5 microns to 27.5 microns. In preferred embodiments, d(0.5) is the specified value ±5%, more preferably, ±2.5%, yet more preferably, ±1.5%.

"d(0.1)," as used herein, describes the value of particle size at which 10% of the total volume of particles is comprised of particles no larger than the indicated size. d(0.1) is used interchangeably herein with d10, $d_{10}$ and D10. It is to be understood that any d(0.1) value specified herein, with the exception of the d(0.1) values in the Figures or the Exemplification, means the specified value ±30% or less of the specified value. For example, when an embodiment or a claim specifies a d(0.1) of about 10 microns, this is to be understood to mean 10 microns ±3.0 microns, that is from 7 microns to 13 microns. In preferred embodiments, d(0.1) is the specified value ±15%, more preferably, ±5%, yet more preferably, ±3%.

It is to be understood that any ratio of d(0.9):d(0.1) or d(0.9):d(0.5) specified herein, with the exception of the d(0.9):d(0.1) or d(0.9):d(0.5) ratios in the Figures or Exemplification, means the specified value ±15% or less of the specified value. For example, when an embodiment or a claim specifies a ratio of d(0.9):d(0.1) of about 10, this is to be understood to mean 10±1.5, that is from 8.5 to 11.5. In preferred embodiments, the d(0.9):d(0.1) or d(0.9):d(0.5) ratio is the specified value ±10%, more preferably, ±5%.

In a first aspect of the fifth embodiment, the particles have a particle size distribution characterized by a d(0.9) of from 10 microns to 100 microns, specifically, a d(0.9) of from 25 microns to 100 microns, more specifically, a d(0.9) of from 60 microns to 100 microns.

In a second aspect of the fifth embodiment, the particles have a particle size distribution characterized by a d(0.9) of from 10 microns to 70 microns, specifically, a d(0.9) of from 25 microns to 70 microns, more specifically, a d(0.9) of from 60 microns to 70 microns.

In a third aspect of the fifth embodiment, the particles have a particle size distribution characterized by a d(0.5) of from 10 microns to 35 microns, specifically, a d(0.5) of from 15 microns to 30 microns, more specifically, a d(0.5) of from 25 to 30 microns. Values and alternative values for d(0.9) are as described in the fifth embodiment, or first aspect thereof.

In a fourth aspect of the fifth embodiment, the particles have a particle size distribution characterized by a d(0.1) of 5 microns or greater, more specifically, 10 microns or greater. For example, in some aspects, the particles have a particle size distribution characterized by a d(0.1) of from 5 microns to 15 microns, more specifically, from 10 microns to 15 microns. Values and alternative values for d(0.9) and d(0.5) are as described in the fifth embodiment, or first or second aspect thereof.

In a fifth aspect of the fifth embodiment, the particles have a particle size distribution characterized by a d(0.9):d(0.1) ratio of 10 or less, specifically, of 7.5 or less, more specifically, of 6 or less. For example, in some aspects, the particles have a particle size distribution characterized by a d(0.9):d(0.1) ratio of from 2 to 10, specifically, of from 5 to 7.5 or, more specifically, of from 5 to 6. Values and alternative values for d(0.9), d(0.5) and d(0.1) are as described in the fifth embodiment, or first, second or third aspect of the foregoing.

In a sixth aspect of the fifth embodiment, the particles have a particle size distribution characterized by a d(0.9):d(0.5) ratio of 4.5 or less, more specifically, of 3 or less. For example, in some aspects, the particles have a particle size distribution characterized by a d(0.9):d(0.5) ratio of from 1.5 to 4.5 or, more specifically, of from 2 to 3. Values and alternative values for d(0.9), d(0.5) and d(0.1), and ratios thereof, are as described in the fifth embodiment, or first, second, third or fourth aspect of the foregoing.

In a seventh aspect of the fifth embodiment, the particles have a unimodal particle size distribution, for example, a normal particle size distribution. Values and alternative values for d(0.9), d(0.5) and d(0.1), and ratios thereof, are as described in the fifth embodiment, or first through fifth aspects of the foregoing.

"Unimodal," used herein in connection with particle size distribution, refers to a particle size distribution that, when graphed, contains a single local maxima. An exemplary unimodal particle size distribution can be found in FIG. 5K.

Figure 5A:
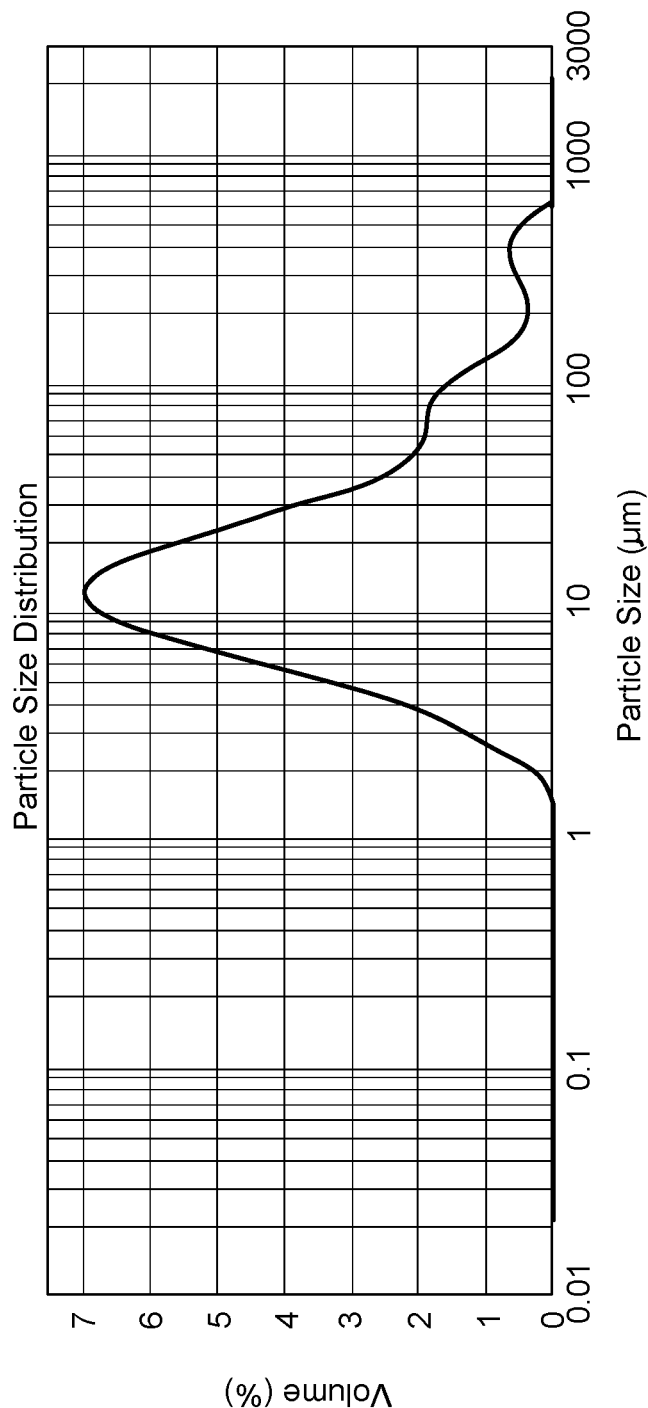

As used herein, "normal particle size distribution" refers to a particle size distribution that obeys a function that represents the distribution of particle sizes in a sample as a symmetrical or substantially symmetrical bell-shaped graph. At least FIG. 5K depicts a normal particle size distribution.

Alternative characteristics of single crystalline Form A in a composition of the fifth embodiment, including alternative XRPD, DSC and/or TGA characteristics, are as described above with respect to the first embodiment.

Pharmaceutical Compositions

Also provided herein are pharmaceutical compositions comprising a single crystalline form (e.g., Form A, B, C or D) or composition described herein and a pharmaceutically acceptable carrier. The composition comprises particles of a single crystalline form (e.g., Form A, B, C or D) of a compound of Structural Formula I. Characteristics and alternative characteristics of the single crystalline form, including alternative XRPD, DSC and/or TGA characteristics, are as described above with respect to the first through fourth embodiments.

A sixth embodiment is a pharmaceutical composition comprising a composition (e.g., a composition of the fifth embodiment, or any aspect thereof) comprising particles of single crystalline Form A of a compound of Structural Formula I and a pharmaceutically acceptable carrier. Characteristics and alternative characteristics of single crystalline Form A, including alternative XRPD, DSC and/or TGA characteristics, are as described above with respect to the first embodiment. Values and alternative values for d(0.9), d(0.5) and d(0.1), and ratios thereof, as well as characteristics of the particle size distribution (e.g., unimodal, normal) of the particles of single crystalline Form A, are as described in the fifth embodiment, of any aspect thereof.

The term "pharmaceutically acceptable carrier" means a non-toxic solvent, dispersant, excipient, adjuvant or other material which is mixed with the active ingredient in order to permit formation of a pharmaceutical composition, i.e., a dosage form capable of being administered to a subject. A "pharmaceutically acceptable carrier" should not destroy the activity of the compound with which it is formulated. Pharmaceutically acceptable carriers are well known in the art.

Pharmaceutically acceptable carriers, adjuvants or vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided pharmaceutical compositions are administrable intravenously and/or intraperitoneally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the pharmaceutical compositions are administered orally, subcutaneously, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Specific pharmaceutically acceptable carriers suitable for use in an oral formulation such as a tablet or capsule include, but are not limited to, microcrystalline cellulose (Avicel PH101), croscarmellose Sodium (Ac-Di-Sol), kollidon 30 powder (polyvinylpyrrolidone, povidone), colloidal silicon dioxide M5-P, magnesium stearate, microcrystalline cellulose (Avcel PH102), sodium lauryl sulfate (Kolliphor SLS Fine) and Colloidal Silicon Dioxide M5-P. Each of the above listed carriers can be used in an oral formulation either alone or in any combination.

Alternatively, pharmaceutical compositions of this invention may be administered in the form of suppositories for rectal administration. Pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches, ointments, creams, foams and gels may also be used. Specific carriers for use in topical formulations include, but are not limited to, 2-hydroxypropyl beta-cyclodextrin (HPBCD), methylcellulose, sodium benzoate, water and glycerin.

For ophthalmic use, provided pharmaceutical compositions may be formulated as micronized suspensions or in an ointment such as petrolatum.

Pharmaceutical compositions of this invention may also be administered by nasal aerosol or inhalation.

In some embodiments, pharmaceutical compositions of this invention are formulated for intra-peritoneal administration.

The amount of compound of Structural Formula I (e.g., single crystalline Form A of the compound of Structural Formula I) in pharmaceutical compositions of this invention is such that is effective to measurably inhibit CRM1, in a biological sample or in a subject. In certain embodiments, a pharmaceutical composition of this invention is formulated for administration to a subject in need of such pharmaceutical composition. The term "subject," as used herein, means an animal. In some embodiments, the animal is a mammal. In certain embodiments, the subject is a veterinary patient (i.e., a non-human mammal patient, such as a dog, a cat, a horse, a pig or a rodent, such as a mouse or rat). In some embodiments, the subject is a dog. In other embodiments, the subject is a human (e.g., a human patient).

The amount of compound of Structural Formula I (e.g., single crystalline Form A of the compound of Structural Formula I) that may be combined with the pharmaceutically acceptable carrier materials to produce a pharmaceutical composition in a single dosage form will vary depending upon the host treated and/or the particular mode of administration. In one embodiment, provided pharmaceutical compositions should be formulated so that a dosage of between 0.01-100 mg/kg body weight/day of the compound of Structural Formula I can be administered to a patient receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day.

It should also be understood that a specific dosage and treatment regimen for any particular subject (e.g., patient) will depend upon a variety of factors, including the activity of the specific compound employed, the age, body weight, general health, sex, diet, time of administration, rate of excretion, drug combination, and the judgment of the treating physician and the severity of the particular disease being treated.

Upon improvement of a subject's condition, a maintenance dose of a pharmaceutical composition of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Treatment and Uses for Pharmaceutical Compositions

Pharmaceutical compositions and compounds described herein are generally useful for the inhibition of CRM1 and are, therefore, useful for treating one or more disorders associated with activity of CRM1. Thus, in certain embodiments, the present invention provides a method for treating a disorder associated with CRM1 activity, comprising administering to a subject in need thereof a therapeutically effective amount of a pharmaceutical composition described herein. The compound of Structural Formula I or (single) crystalline form thereof, pharmaceutical composition thereof or combination of the foregoing can also be administered to cells in culture, e.g., in vitro or ex vivo, or to a subject, e.g., in vivo, to treat, prevent, and/or diagnose a variety of disorders, including those described hereinbelow.

The activity of a compound Structural Formula I, or (single) crystalline form thereof, pharmaceutical composition thereof, or combination of the foregoing as an inhibitor of CRM1 may be assayed in vitro, in vivo or in a cell line. Detailed conditions for assaying a compound of Structural Formula I as an inhibitor of CRM1 are set forth in International Publication No. WO 2013/019548.

The term "treat" or "treating" means to alleviate symptoms, eliminate the causation of the symptoms, either on a temporary or permanent basis, or to prevent or slow the appearance of symptoms of the named disorder or condition.

The term "CRM1-mediated" disorder or condition or "disorder associated with CRM1 activity," as used herein, means any disease or other deleterious condition in which CRM1 is known to play a role. Accordingly, another embodiment of the present invention relates to treating or lessening the severity of one or more diseases in which CRM1 is known to play a role. In some embodiments, the present invention provides methods of treating a disease associated with expression or activity of p53, p73, p21, pRB, p27, IκB, NFκB, c-Abl, FOXO proteins, COX-2, or an HDAC (histone deacetylases) in a subject comprising administering to the subject a therapeutically effective amount of a pharmaceutical composition described herein. In another embodiment, the present invention relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder wherein said method comprises administering to a patient in need thereof a compound or composition according to the present invention. In a more specific embodiment, the present invention relates to a method of treating or lessening the severity of cancer. Specific examples of the above disorders are set forth in detail below.

The term "therapeutically effective amount" means an amount of the compound of Structural Formula I or (single) crystalline form thereof (typically, in a pharmaceutical composition described herein) which is effective in treating or lessening the severity of one or more symptoms of a disorder or condition. In the case of promoting wound healing, a therapeutically effective amount is an amount of the compound of Structural Formula I or (single) crystalline form thereof (typically, in a pharmaceutical composition described herein) that promotes healing of a wound.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

Cancers treatable by the pharmaceutical compositions or compounds of this invention include, but are not limited to, hematologic malignancies (leukemias, lymphomas, myelomas including multiple myeloma, myelodysplastic and myeloproliferative syndromes) and solid tumors (carcinomas such as prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple.

Inflammatory disorders treatable by the pharmaceutical compositions or compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the pharmaceutical compositions or compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by pharmaceutical compositions or compounds of the invention include, but are not limited to, Parkinson's, Alzheimer's, and Huntington's, and Amyotrophic lateral sclerosis (ALS/Lou Gehrig's Disease).

Pharmaceutical compositions or compounds described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Pharmaceutical compositions or compounds described herein may also be used to treat disorders related to food intake such as obesity and hyperphagia.

In another embodiment, a pharmaceutical composition or compounds described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In some embodiments, the disorder or condition associated with CRM1 activity is beta-thalassemia, muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present invention provides a use of a pharmaceutical composition or compounds described herein for the manufacture of a medicament for the treatment of a disorder associated with CRM1 activity. The present invention also provides a pharmaceutical composition described herein for use in treating a disorder associated with CRM1 activity. Specific examples of disorders associated with CRM1 activity are as set forth in detail herein.

In yet further aspects, the present invention provides a use of a pharmaceutical composition or compounds described herein for the manufacture of a medicament for the treatment of a disease associated with expression or activity of p53, p73, p21, pRB, p27, IκB, NFκB, c-Abl, FOXO proteins, COX-2 or an HDAC in a subject. In some embodiments, the present invention provides a use of a pharmaceutical composition described herein in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

In some embodiments, the present invention provides a method for inhibiting CRM1 in a biological sample comprising contacting the biological sample with, or administering to the patient, a pharmaceutical composition of the invention.

Neoplastic Disorders

A pharmaceutical composition or compound described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome.

Exemplary sarcomas include fibrosarcoma, alveolar soft part sarcoma (ASPS), liposarcoma, leiomyosarcoma, chondrosarcoma, synovial sarcoma, chordoma, spindle cell sarcoma, histiocytoma, rhabdomyosarcoma, Ewing's sarcoma, neuroectodermal sarcoma, phyllodes/osteogenic sarcoma and chondroblastic osteosarcoma.

Metastases of the aforementioned cancers can also be treated or prevented in accordance with the methods described herein.

Combination Therapies

In some embodiments, the compound of Structural Formula I or (single) crystalline form thereof (e.g., in a pharmaceutical composition described herein) is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, the compound of Structural Formula I may be administered with another therapeutic agent simultaneously or sequentially in separate unit dosage forms or together in a single unit dosage form. Accordingly, the present invention provides a single unit dosage form comprising the compound of Structural Formula I (e.g., a crystalline form or single crystalline form of the compound of Structural Formula I), an additional therapeutic agent, and a pharmaceutically acceptable carrier.

In one embodiment of the invention, where a second therapeutic agent is administered to a subject, the effective amount of the compound of Structural Formula I is less than its effective amount would be where the second therapeutic agent is not administered. In another embodiment, the effective amount of the second therapeutic agent is less than its effective amount would be were the compound of Structural Formula I not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compound of Structural Formula I. Alternatively, those agents may be part of a single dosage form, mixed together with the compound of Structural Formula I in a single pharmaceutical composition.

In certain embodiments, the compound of Structural Formula I or (single) crystalline form thereof (e.g., in a pharmaceutical composition described herein) may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa. In a specific embodiment, the compound of Structural Formula I or (single) crystalline form thereof (e.g., in a pharmaceutical composition described herein) is administered in combination with dexamethasone.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiments, the compound of Structural Formula I may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, the compound of Structural Formula I is administered in combination with an anthracycline or a Topo II inhibitor. In certain embodiments, the compound of Structural Formula I is administered in combination with Doxorubicin (Dox). In certain embodiments, the compound of Structural Formula I is administered in combination with bortezomib (and more broadly including carfilzomib).

Cancer Combination Therapies

In some embodiments, the compound of Structural Formula I or (single) crystalline form thereof, (e.g., in a pharmaceutical composition described herein) is administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors, and anti-angiogenic therapies. Examples of each of these treatments are provided below. As used herein, the term "combination," "combined," and related terms refer to the simultaneous or sequential administration of therapeutic agents in accordance with this invention. For example, the compound of Structural Formula I can be administered with another therapeutic agent simultaneously or sequentially in separate unit dosage forms or together in a single unit dosage form. Accordingly, the present invention provides a single unit dosage form comprising the compound of Structural Formula I (e.g., a crystalline form or single crystalline form of the compound of Structural Formula I), an additional therapeutic agent, and a pharmaceutically acceptable carrier.

The amount of both the compound of Structural Formula I and additional therapeutic agent (in those pharmaceutical compositions which comprise an additional therapeutic agent as described above) that can be combined with the carrier materials to produce a single dosage form will vary depending upon the host treated and the particular mode of administration. Preferably, pharmaceutical compositions of this invention should be formulated so that a dosage of between 0.01-100 mg/kg body weight/day of a compound of Structural Formula I can be administered.

Chemotherapy

In some embodiments, a pharmaceutical composition described herein is co-administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carfilzomib, Carmofur, Carmustine, Celecoxib, Cetuximab, Chlorambucil, Chlormethine, CHOEP-21, CHOP, Cisplatin, Cladribine, Clofarabine, Crisantaspase, Cyclophosphamide, Cytarabine or ara-C, Dacarbazine, Dactinomycin, DA EPOCH, Daratumumab, Daunorubicin, Decitabine, Demecolcine, Dexamethasone, Docetaxel, Doxorubicin, Efaproxiral, Elesclomol, Elsamitrucin, Enocitabine, Epirubicin, Eribulin, Estramustine, Etoglucid, Etoposide, FLAG (Flu+Cyt), Floxuridine, Fludarabine, Fluorouracil (5FU), FOLFOX, Fotemustine, Gemcitabine, gemcitabine-oxaliplatin (GemOx), Gliadel implants, Hydroxycarbamide, Hydroxyurea, Ibrutinib, Idarubicin, Ifosfamide, Irinotecan, Irofulven, Ixabepilone, Ixazomib, Larotaxel, Lenalidomide, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nab-paclitaxel, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, PLD (pegylated liposomal doxorubicin), Plicamycin, Pomalidomide, Porfimer sodium, Prednimustine, Procarbazine, Raltitrexed, Ranimustine, R-CHOP, r-dhaox, r-dhap, Rituximab, Romidepsin Rubitecan, Sapacitabine, Semustine, Sitimagene ceradenovec, Sorafonib, Stratapla-tin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a pharmaceutical composition described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a pharmaceutical composition described herein, e.g., Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Angiogenesis

Pharmaceutical compositions described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularization or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Pharmaceutical compositions described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including 06-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Immunotherapy

In some embodiments, a pharmaceutical composition described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agent(s) can be used in combination with a pharmaceutical composition described herein.

Hormonal Therapy

In some embodiments, a pharmaceutical composition described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a pharmaceutical composition described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The pharmaceutical compositions described herein may be used to treat or prevent a disease or disorder associated with inflammation, particularly in humans and other mammals. A pharmaceutical composition described herein may be administered prior to the onset of, at, or after the initiation of inflammation. When used prophylactically, the pharmaceutical compositions are preferably provided in advance of any inflammatory response or symptom. Administration of the pharmaceutical compositions can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a pharmaceutical composition described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a pharmaceutical composition described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the pharmaceutical compositions described herein can be used to treat multiple sclerosis.

Viral Infections

Pharmaceutical compositions described herein may be used to treat or prevent a disease or disorder associated with a viral infection, particularly in humans and other mammals. A pharmaceutical composition described herein may be administered prior to the onset of, at, or after the initiation of viral infection. When used prophylactically, the pharmaceutical composition is preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral influenza A strains include H1N1, H3N2, H5N1, H7N3, H7N9. A compound described herein can also be used to treat or prevent influenza B.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

Ophthalmology

Pharmaceutical compositions described herein may be used to treat or prevent an ophthamology disorder. Exemplary ophthamology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the pharmaceutical compositions described herein include proliferative vitreoretinopathy and chronic retinal detachment.

Inflammatory eye diseases are also treatable using the pharmaceutical compositions described herein.

Neurodegenerative Disease

Pharmaceutical compositions described herein may be used to treat or prevent an neurodegenerative disease. Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyms.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rabl may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics includes antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Pharmaceutical compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a therapeutically effective amount of a pharmaceutical composition described herein. The method need not achieve complete healing or closure of the wound; it is sufficient for the method to promote any degree of wound closure. In this respect, the method can be employed alone or as an adjunct to other methods for healing wounded tissue.

Pharmaceutical compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a dog, a cat, a horse, a pig, or a rodent, such as a mouse.

In some embodiments, the pharmaceutical compositions described herein useful for wound healing are administered topically, for example, proximate to the wound site, or systemically.

More specifically, a therapeutically effective amount of a pharmaceutical composition described herein can be administered (optionally in combination with other agents) to the wound site by coating the wound or applying a bandage, packing material, stitches, etc., that are coated or treated with the compound or composition described herein. As such, the pharmaceutical compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the pharmaceutical composition described herein. Topical delivery systems may be used to administer topical formulations of the compounds and compositions described herein.

Alternatively, the pharmaceutical compositions described herein can be administered at or near the wound site by, for example, injection of a solution, injection of an extended release formulation, or introduction of a biodegradable implant comprising the compound or composition described herein.

The pharmaceutical compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and, thus, initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds. Other examples of chronic wounds include chronic ulcers, diabetic wounds, wounds caused by diabetic neuropathy, venous insufficiencies, and arterial insufficiencies, and pressure wounds and cold and warm burns. Yet other examples of chronic wounds include chronic ulcers, diabetic wounds, wounds caused by diabetic neuropathy, venous insufficiencies, arterial insufficiencies, and pressure wounds.

Acute wounds include, but are not limited to, post-surgical wounds, lacerations, hemorrhoids and fissures.

In a particular embodiment, the pharmaceutical compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The pharmaceutical compositions described herein can also be used for diabetic wound healing, gastrointestinal wound healing, or healing of an adhesion due, for example, to an operation.

The pharmaceutical compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The pharmaceutical compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer. Examples of internal wounds include, but are not limited to, fistulas and internal wounds associated with cosmetic surgery, internal indications, Crohn's disease, ulcerative colitis, internal surgical sutures and skeletal fixation. Other examples of internal wounds include, but are not limited to, fistulas and internal wounds associated with cosmetic surgery, internal indications, internal surgical sutures and skeletal fixation.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, seton wounds, stab wounds, surgical wounds, subcutaneous wounds, diabetic lesions, or tangential wounds. Additional examples of wounds that can be treated by the pharmaceutical compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation. In more preferred embodiments, the wound is selected from the group consisting of an incised wound, an open wound, a surgical or post surgical wound, a diabetic lesion, a pressure sore, a bedsore, and a condition or wound related to diabetes or poor circulation.

In some embodiments, the wound is selected from the group consisting of a non-radiation burn wound, an incised wound, an open wound, a surgical or post surgical wound, a diabetic lesion, a thermal burn, a chemical burn, a pressure sore, a bedsore, and a condition related to diabetes or poor circulation. In some embodiments, the wound is selected from the group consisting of an incised wound, an open wound, a surgical or post surgical wound, a diabetic lesion, a pressure sore, a bedsore, and a condition related to diabetes or poor circulation.

The present disclosure also relates to methods and pharmaceutical compositions for reducing scar formation during wound healing in a subject. The pharmaceutical compositions described herein can be administered directly to the wound or to cells proximate the wound at an amount effective to reduce scar formation in and/or around the wound. Thus, in some embodiments, a method of reducing scar formation during wound healing in a subject is provided, the method comprising administering to the subject a therapeutically effective amount of a pharmaceutical composition described herein.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

Other Disorders

Pharmaceutical compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Pharmaceutical compositions described herein are useful as radiosensitizers. Therefore, pharmaceutical compositions described herein can be administered in combination with radiation therapy. Radiation therapy is the medical use of high-energy radiation (e.g., X-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy X-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intercavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. *Cancer Res.*, 2001; 61:2008-2014 and Goldenber, D. M. *J. Nucl. Med.*, 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749-63, the contents of which are incorporated by reference herein.

In addition to targeted delivery, bracytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, X-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both $\alpha$ and $\beta$-particle emitters have been investigated. Alpha particles are particularly good cytotoxic agents because they dissipate a large amount of energy within one or two cell diameters. The $\beta$-particle emitters have relatively long penetration range (2-12 mm in the tissue) depending on the energy level. The long-range penetration is particularly important for solid tumors that have heterogeneous blood flow and/or receptor expression. The $\beta$-particle emitters yield a more homogeneous dose distribution even when they are heterogeneously distributed within the target tissue.

In a particular embodiment, therapeutically effective amounts of the pharmaceutical compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine 5$^{th}$ ed., Edited by R. C. Bast et al., July 2000, BC Decker.

Synthetic Methods

Also provided herein are synthetic methods for preparing crystalline forms (e.g., single crystalline forms, such as single crystalline Form A and single crystalline Form D) of Selinexor.

A seventh embodiment provides a method of preparing a single crystalline form of a compound represented by Structural Formula I, wherein the single crystalline form is Form A and is characterized by at least three X-ray powder diffraction peaks at 2θ angles selected from 4.4°, 19.9°, 21.3° and 22.0°. The method comprises:

(a) suspending single crystalline Form B, C or D of the compound of Structural Formula I, or a mixture comprising two or more of single crystalline Form B, C or D of the compound of Structural Formula I, in isopropanol or a mixture of isopropanol and water to form a slurry, wherein single crystalline Form D is characterized by at least three X-ray powder diffraction peaks at 2θ angles selected from 3.7°, 7.3°, 10.9°, 18.3° and 21.9°, single crystalline Form B is characterized by at least three X-ray powder diffraction peaks at 2θ angles selected from 9.4°, 11.1°, 16.5°, 18.3° and 18.8° and single crystalline Form C is characterized by at least three X-ray diffraction peaks at 2θ angles selected from 3.7°, 11.2°, 12.1° and 18.6°;

(b) heating the slurry to a temperature less than or equal to about 70° C. to form a second slurry or a solution;

(c) cooling the second slurry or the solution and adding water to the second slurry or the solution, thereby forming solid particles of crystalline Form A of the compound of Structural Formula I; and (d) isolating the solid particles of crystalline Form A, thereby preparing a composition comprising particles of single crystalline Form A of the compound of Structural Formula I. Characteristics and alternative characteristics for single crystalline Form A and single crystalline Forms B, C and D, including alternative XRPD, DSC and/or TGA characteristics, are as described above with respect to the first and second embodiments, respectively. Values and alternative values for d(0.9), d(0.5) and d(0.1), and ratios thereof, as well as characteristics of the particle size distribution (e.g., unimodal, normal) of the particles of single crystalline Form A, are as described in the fifth embodiment, of any aspect thereof.

In some aspects of the seventh embodiment, the solid particles of crystalline Form A have a unimodal particle size distribution characterized by a d(0.9) of 70 microns or less. In some aspects of the seventh embodiment, the solid particles of crystalline Form A have a unimodal particle size distribution characterized by a d(0.9) of 100 microns or less.

In some aspects of the seventh embodiment, single crystalline Form B, C or D of the compound of Structural Formula I or a mixture comprising two or more of the single crystalline forms of the compound of Structural Formula I, is suspended in a mixture of isopropanol and water in step (a).

In some aspects of the seventh embodiment, the ratio of isopropanol to water by volume in the mixture of isopropanol and water is from about 0.1 to about 4, for example, about 1.

In some aspects of the seventh embodiment, single crystalline Form B, C or D of Structural Formula I or a mixture comprising two or more of single crystalline Forms B, C or D of the compound of Structural Formula I is suspended in an amount of isopropanol or mixture of isopropanol and water of from about 5 to about 10 parts by weight with respect to single crystalline Form B, C or D of the compound of Structural Formula I or a mixture comprising two or more of single crystalline Form B, C or D of the compound of Structural Formula I, for example, from about 6 to about 7 parts by weight with respect to single crystalline Form B, C or D or a mixture comprising two or more of single crystalline Form B, C or D of the compound of Structural Formula I.

In some aspects of the seventh embodiment, the slurry is heated to a temperature less than or equal to about 50° C. In some aspects of the seventh embodiment, the slurry is heated to a temperature of from about 35° C. to about 70° C. or of from about 35° C. to about 50° C. In some aspects of the seventh embodiment, the slurry is heated to a temperature of from about 65° C. to about 70° C.

In some aspects of the seventh embodiment, the second slurry or the solution is cooled to from about 0° C. to about 55° C. For example, the second slurry or the solution is cooled to from about 0° C. to about 5° C., to from about 15° C. to about 20° C. or to from about 45° C. to about 50° C.

In some aspects of the seventh embodiment, water is added to the second slurry or the solution in an amount of from about 5 parts by weight to about 15 parts by weight with respect to single crystalline Form B, C or D of the compound of Structural Formula I or a mixture comprising two or more of crystalline Forms B, C or D of the compound of Structural Formula I. For example, water is added to the second slurry or the solution in an amount of from about 7 parts by weight to about 10 parts by weight or of about 10 parts by weight with respect to single crystalline Form B, C or D of the compound of Structural Formula I or a mixture comprising two or more of crystalline Forms B, C or D of the compound of Structural Formula I.

Isolating the solid particles of crystalline Form A is typically effected by filtration and, optionally, rinsing of the filtered solids with a solvent (e.g., a chilled solvent), although other means of isolating the solid particles are known in the art. Other means of isolating the solid particles of crystalline Form A include, but are not limited to, distilling liquid present in the second slurry or the solution away from the solid particles or otherwise drying the solid particles of crystalline Form A, for example, by heating the second slurry or the solution, by subjecting the second slurry or the solution to reduced pressure (e.g., in vacuo) or any combination of the foregoing.

A eighth embodiment provides a method of preparing a single crystalline form of a compound represented by Structural Formula I, wherein the single crystalline form is Form A and is characterized by at least three X-ray powder diffraction peaks at 2θ angles selected from 4.4°, 19.9°, 21.3° and 22.0°. The method comprises:

(a) suspending single crystalline Form B, C or D of the compound of Structural Formula I or a mixture comprising two or more of single crystalline Form B, C or D of the compound of Structural Formula I, in isopropanol or a mixture of isopropanol and water to form a slurry, wherein single crystalline Form D is characterized by at least three X-ray powder diffraction peaks at 2θ angles selected from 3.7°, 7.3°, 10.9°, 18.3° and 21.9°, single crystalline Form B is characterized by at least three X-ray powder diffraction peaks at 2θ angles selected from 9.4°, 11.1°, 16.5°, 18.3° and 18.8° and single crystalline Form B is characterized by at least three X-ray diffraction peaks at 2θ angles selected from 3.7°, 11.2°, 12.1° and 18.6°;

(b) heating the slurry to a temperature less than or equal to about 70° C. to form a second slurry or a solution;

(c) adding water to the second slurry or the solution and cooling the second slurry or the solution and thereby forming solid particles of crystalline Form A of the compound of Structural Formula I; and (d) isolating the solid particles of crystalline Form A,
thereby preparing a composition comprising particles of single crystalline Form A of the compound of Structural Formula I. Characteristics and alternative characteristics for single crystalline Form A and single crystalline Forms B, C and D, including alternative XRPD, DSC and/or TGA characteristics, are as described above with respect to the first and second embodiments, respectively. Values and alternative values for d(0.9), d(0.5) and d(0.1), and ratios thereof, as well as characteristics of the particle size distribution (e.g., unimodal, normal) of the particles of single crystalline Form A, are as described in the fifth embodiment, of any aspect thereof.

In some aspects of the eighth embodiment, the solid particles of crystalline Form A have a unimodal particle size distribution characterized by a d(0.9) of 70 microns or less. In some aspects of the eighth embodiment, the solid particles of crystalline Form A have a unimodal particle size distribution characterized by a d(0.9) of 100 microns or less.

In some aspects of the eight embodiment, single crystalline Form B, C or D of the compound of Structural Formula I or a mixture comprising two or more of the single crystalline forms of the compound of Structural Formula I, is suspended in a mixture of isopropanol and water in step (a).

In some aspects of the eighth embodiment, the ratio of isopropanol to water by volume in the mixture of isopropanol and water is from about 0.1 to about 4, for example, about 1.

In some aspects of the eighth embodiment, single crystalline Form B, C or D of Structural Formula I or a mixture comprising two or more of single crystalline Form B, C or D of the compound of Structural Formula I is suspended in an amount of isopropanol or mixture of isopropanol and water of from about 5 to about 10 parts by weight with respect to single crystalline Form B, C or D of the compound of Structural Formula I or a mixture comprising two or more of single crystalline Form B, C or D of the compound of Structural Formula I, for example, from about 6 to about 7 parts by weight with respect to single crystalline Form B, C or D or a mixture comprising two or more of single crystalline Form B, C or D of the compound of Structural Formula I.

In some aspects of the eighth embodiment, the slurry is heated to a temperature less than or equal to about 50° C. In some aspects of the eighth embodiment, the slurry is heated to a temperature of from about 35° C. to about 70° C. or of from about 35° C. to about 50° C. In some aspects of the seventh embodiment, the slurry is heated to a temperature of from about 65° C. to about 70° C.

In some aspects of the eighth embodiment, the second slurry or the solution is cooled to from about 0° C. to about 55° C. For example, the second slurry or the solution is cooled to from about 0° C. to about 5° C., to from about 15° C. to about 20° C. or to from about 45° C. to about 50° C.

In some aspects of the eighth embodiment, water is added to the second slurry or the solution in an amount of from about 5 parts by weight to about 15 parts by weight with respect to single crystalline Form B, C or D of the compound of Structural Formula I or a mixture comprising two or more of crystalline Form B, C or D of the compound of Structural Formula I. For example, water is added to the second slurry or the solution in an amount of from about 7 parts by weight to about 10 parts by weight or of about 10 parts by weight with respect to single crystalline Form D, or single crystalline Form B, C or D of the compound of Structural Formula I or a mixture comprising two or more of crystalline Form B, C or D of the compound of Structural Formula I.

Isolating the solid particles of crystalline Form A is typically effected by filtration and, optionally, rinsing of the filtered solids with a solvent (e.g., a chilled solvent), although other means of isolating the solid particles are known in the art. Other means of isolating the solid particles of crystalline Form A include, but are not limited to, distilling liquid present in the second slurry or the solution away from the solid particles or otherwise drying the solid particles of crystalline Form A, for example, by heating the second slurry or the solution, by subjecting the second slurry or the solution to reduced pressure (e.g., in vacuo) or any combination of the foregoing.

A ninth embodiment provides a method of preparing a single crystalline form of a compound represented by Structural Formula I, wherein the single crystalline form is Form A and is characterized by at least three X-ray powder diffraction peaks at 2θ angles selected from 4.4°, 19.9°, 21.3° and 22.0°. The method comprises: heating single crystalline Form B, C or D of the compound of Structural Formula I or a mixture comprising two or more of crystalline Form B, C or D of the compound of Structural Formula I and inducing formation of solid particles of crystalline Form A; or maturing single crystalline Form B, C or D of the compound of Structural Formula I, or a mixture comprising two or more of crystalline Form B, C or D of the compound of Structural Formula I in a solvent system and inducing formation of solid particles of crystalline Form A; or drying single crystalline Form B, C or D of the compound of Structural Formula I, or a mixture comprising two or more of crystalline Form B, C or D of the compound of Structural Formula I, thereby forming solid particles of crystalline Form A; or any combination of the foregoing; and isolating the solid particles of crystalline Form A, thereby preparing single crystalline Form A of the compound of Structural Formula I. Characteristics and alternative characteristics for single crystalline Forms A, B, C and D, including alternative XRPD, DSC and/or TGA characteristics, are as described above with respect to the first, second, third and fourth embodiments, respectively. Values and alternative values for d(0.9), d(0.5) and d(0.1), and ratios thereof, as well as characteristics of the particle size distribution (e.g., unimodal, normal) of the particles of single crystalline Form A, are as described in the fifth embodiment, of any aspect thereof.

In some aspects of the ninth embodiment, the method comprises:
heating a mixture comprising two or more crystalline forms of the compound of Structural Formula I and inducing formation of solid particles of crystalline Form A; or
maturing a mixture comprising two or more crystalline forms of the compound of Structural Formula I in a solvent system and inducing formation of solid particles of crystalline Form A; or
drying a mixture comprising two or more crystalline forms of the compound of Structural Formula I, thereby forming solid particles of crystalline Form A; or
any combination of the foregoing.

In some aspects of this aspect, the mixture comprises two or more crystalline forms selected from Form A, Form B, Form C or Form D, more specifically, two or more crystalline forms selected from Form B, Form C or Form D. In some aspects of this aspect, one of the two or more crystalline forms is Form B, Form C or Form D. In some aspects of this aspect, the mixture does not comprise Form A.

In alternative aspects of the ninth embodiment, the method comprises:
heating single crystalline Form B, C or D of the compound of Structural Formula I and inducing formation of solid particles of crystalline Form A; or maturing single crystalline Form B, C or D of the compound of Structural Formula I in a solvent system and inducing formation of solid particles of crystalline Form A; or drying single crystalline Form B, C or D of the compound of Structural Formula I, thereby forming solid particles of crystalline Form A; or any combination of the foregoing. In some aspects of this aspect, the single crystalline form is Form B. In other aspects of this aspect, the single crystalline form is Form C. In yet other aspects of this aspect, the single crystalline form is Form D.

"Inducing formation," used herein, includes any conditions that induce the compound of Structural Formula I to crystallize as the specified crystalline form, for example, crystalline Form A or crystalline Form D. Inducing formation includes merely allowing solid particles of the specified crystalline form to precipitate from a solution or slurry, for example, without actively performing any step. Inducing formation also includes maturing (e.g., aging, with or without cooling, and/or cycling) a solution comprising a compound of Structural Formula I in an appropriate solvent system and/or allowing a solution comprising a compound of Structural Formula I in an appropriate solvent system to slowly evaporate, with or without cooling. Inducing formation also includes cooling the compound of Structural Formula I or a solution including the compound of Structural Formula I. Other methods of inducing formation of a crystalline solid are known in the art and include, for example, seeding, and/or using anti-solvents and vapor diffusion. In preferred embodiments, inducing formation comprises cooling the compound of Structural Formula I or a solution or slurry including the compound of Structural Formula I in an appropriate solvent system.

"Solvent system," as used herein, refers to a single solvent or a mixture of two or more (typically, two) different solvents. Exemplary solvents for a solvent system include water and organic solvents such as, but not limited to, methanol, s-butanol, m-butanol, i-butanol, cyclopentylmethylether, cyclopentylethylether, heptane, 1,4-dioxane, 1,2-dimethoxyethane, 1,2-dichloroethane, toluene, cumene, diisopropyl ether, anisole, dichloromethane, tetrahydrofuran, 2-methyltetrahydrofuran, tert-butanol, 2-propanol, ethanol, ethyl acetate, isopropyl acetate, nitromethane, acetonitrile, dimethylsulfoxide, tert-butylmethyl ether (TBME), methylisobutylketone (MIBK), propyl acetate, butyl acetate, dimethoxyethane, isooctane and propionitrile.

Preferred solvent systems for inducing formation of crystalline Form A include propionitrile, isopropanol, n-propanol, a mixture of isopropanol and water and a mixture of 2-methyltetrahydrofuran and isooctane, heptane, toluene or acetonitrile (comprising less than or about 20% acetonitrile by volume). A particularly preferred solvent system for inducing formation of solid particles of crystalline Form A is a mixture of isopropanol and water (e.g., comprising from about 20% to about 50% isopropanol by volume). The solvent system for inducing formation of solid particles of crystalline Form A at temperatures below 50° C. should not be nitromethane, acetonitrile, or a mixture of acetonitrile and a second solvent comprising greater than about 20% acetonitrile by volume.

Typically, when single crystalline Form B, C or D of the compound of Structural Formula I or a mixture comprising two or more of crystalline Form B, C or D of the compound of Structural Formula I is heated, single crystalline Form B, C or D of the compound of Structural Formula I or the mixture comprising two or more of crystalline Form B, C or D of the compound of Structural Formula I is heated in a solvent system, for example, an aqueous mixture of isopropanol and water. However, single crystalline Form B, C or D of the compound of Structural Formula I or a mixture comprising two or more of crystalline Form B, C or D of the compound of Structural Formula I can also be heated neat (in the absence of solvent). A preferred solvent system for heating single crystalline Form B, C or D of the compound of Structural Formula I or the mixture comprising two or more crystalline forms of the compound of Structural Formula I is a mixture of isopropanol in water (e.g., a mixture comprising from about 20% to about 50% isopropanol by volume).

"Maturing," as used herein, includes both aging single crystalline Form B, C or D of the compound of Structural Formula I or a mixture comprising two or more crystalline forms of the compound of Structural Formula I in a solvent system (with or without slow evaporation), for example, under substantially constant conditions (e.g., ambient temperature and pressure) for a period of time (e.g., less than 30 minutes, less than 1 hour, at least 30 minutes, at least 1 hour, at least 4 hours, at least 12 hours, at least 1 day, at least 7 days), and cycling single crystalline Form B, C or D of the compound of Structural Formula I or a mixture comprising two or more crystalline forms of the compound of Structural Formula I in a solvent system, for example, between two or more temperatures over a period of time (e.g., between room temperature and 50° C. every four hours).

Preferred solvent systems for maturing single crystalline Form B, C or D of the compound of Structural Formula I or a mixture comprising two or more crystalline forms of the compound of Structural Formula I include ethyl acetate, a mixture of isopropanol and water (e.g., a mixture comprising from about 20% to about 50% isopropanol by volume) and a mixture of ethanol and water.

"Room temperature" and "ambient temperature," as used herein, means a temperature of from about 16° C. to about 25° C.

"Ambient conditions," as used herein, refers to room temperature and atmospheric pressure conditions.

Drying single crystalline Form B, C or D of the compound of Structural Formula I or a mixture comprising two or more of crystalline Form B, C or D of the compound of Structural Formula I can be accomplished, for example, by distilling any liquid present away from the solid crystalline form(s), by exposing the solid crystalline form(s) to ambient conditions or passing a stream of gas, such as nitrogen gas, over the solid crystalline form(s) (and thereby inducing the evaporation or desolvation of any liquid or entrapped volatile substance, such as acetonitrile), by subjecting the solid crystalline form(s) to reduced pressure (e.g., in vacuo) or any combination of the foregoing. Single crystalline Form D, in particular, can be converted to single crystalline Form A by drying under conditions in which acetonitrile can desolvate from single crystalline Form D, for example, by subjecting single crystalline Form D to reduced pressure (e.g., in vacuo) or by exposing single crystalline Form D to ambient conditions or passing a stream of gas over single crystalline Form D.

It is understood that, quite often, in practice, the steps for preparing single crystalline Form A according to the methods described herein entail a combination of heating, maturing and/or drying. For example, when a mixture comprising two or more crystalline forms of the compound of Structural Formula I is aged, for example, at 50° C. for 72 hours up to 1 week, the method of preparing single crystalline Form A comprises heating and maturing. When single crystalline Form D of the compound of Structural Formula I is placed in vacuo at 35° C., the method of preparing single crystalline Form A comprises drying and heating.

Isolating the solid particles of crystalline Form A can be effected by filtration and, optionally, rinsing of the filtered solids with a solvent (e.g., a chilled solvent), although other means of isolating solid particles are known in the art. Other means of isolating the solid particles of crystalline Form A include, but are not limited to, distilling any liquid present away from the solid particles or otherwise drying the solid particles of crystalline Form A, for example, by heating a slurry or solution containing the particles (to induce evaporation of any liquid or volatile substance), by subjecting a slurry or solution to reduced pressure (e.g., in vacuo), by passing a stream of gas (e.g., nitrogen) over the sample, or any combination of the foregoing.

A tenth embodiment provides a method of preparing a single crystalline form of a compound represented by Structural Formula I wherein the single crystalline form is Form D and is characterized by at least three X-ray powder diffraction peaks at 2θ angles selected from 3.7°, 7.3°, 10.9°, 18.3° and 21.9°. The method comprises:

dissolving the compound of Structural Formula I in a solvent system comprising acetonitrile;

inducing formation of solid particles of crystalline Form D of the compound of Structural Formula I, or single crystalline Form B or C of the compound of Structural Formula I or a mixture comprising two or more of crystalline Form B, C or D of the compound of Structural Formula I; and isolating the solid particles of crystalline Form B, C or D of Structural Formula I or a mixture comprising two or more of crystalline Form B, C or D of the compound of Structural Formula I, thereby preparing single crystalline Form B, C or D of the compound of Structural Formula I or a mixture comprising two or more of crystalline Form B, C or D of the compound of Structural Formula I of the compound of Structural Formula I. Characteristics and alternative characteristics for single crystalline Form D, including alternative XRPD, DSC and/or TGA characteristics, are as described above with respect to the second embodiment.

Preferred solvent systems for the method provided by the tenth embodiment include acetonitrile and mixtures of acetonitrile and a second solvent selected from water, 2-methyltetrahydrofuran, ethyl acetate or a combination of the foregoing, containing greater than 20% by volume acetonitrile, such as greater than or about 40% acetonitrile or greater than or about 95% acetonitrile.

In some aspects of the tenth embodiment, inducing formation of solid particles of crystalline Form D comprises cooling the solution of the compound of Structural Formula I in the solvent system. Preferred solvent systems for inducing formation of solid particles of crystalline Form D include acetonitrile and mixtures of acetonitrile and a second solvent selected from water, 2-methyltetrahydrofuran, ethyl acetate or a combination of the foregoing, containing greater than 20% by volume acetonitrile, such as at least or about 40% acetonitrile or at least or about 95% acetonitrile.

Isolating the solid particles of single crystalline Form B, C or D of the compound of Structural Formula I or a mixture comprising two or more of crystalline Form B, C or D of the compound of Structural Formula I, is preferably achieved by filtration and, optionally, rinsing of the filtered solids with a solvent (e.g., a chilled solvent). For example, single crystalline Form D can be isolated by filtration and rinsing of the filtered solids with acetonitrile, for example, cold acetonitrile.

Other means of isolating the solid particles include, but are not limited to, distilling any liquid present away from the solid particles or otherwise drying the solid particles, for example, by heating a slurry or solution containing the particles (to induce evaporation of any liquid or volatile substance), by subjecting a slurry or solution to reduced pressure (e.g., in vacuo), by passing a stream of gas (e.g., nitrogen) over the crystalline form, or any combination of the foregoing. However, as described in the Exemplification, crystalline Form D can desolvate under a variety of conditions. Thus, extended heating or being subjected to reduced pressures for an extended period of time can cause crystalline Form D to convert to crystalline Form B, C and/or A or mixtures thereof. One skilled in the art will be able to determine how to isolate crystalline Form D without undue experimentation using the guidance provided herein.

In some aspects of the tenth embodiment, single crystalline Form D is in the form of a solvate, for example, an acetonitrile solvate. More particularly, the solvate (e.g., acetonitrile solvate) comprises from about 0.5 to about 1.5 molar equivalents of solute (e.g., acetonitrile) per molar equivalent of the compound of Structural Formula I, yet more particularly, one molar equivalent of solute per molar equivalent of the compound of Structural Formula I.

In some aspects of the tenth embodiment, the solvent system comprises greater than 20% by volume acetonitrile, for example, at least or about 40% by volume acetonitrile, or at least or about 95% by volume acetonitrile.

An eleventh embodiment provides a method of preparing a compound of Structural Formula I. The method comprises: combining a trialkylamine, 2-methyltetrahydrofuran, a compound of Structural Formula II:

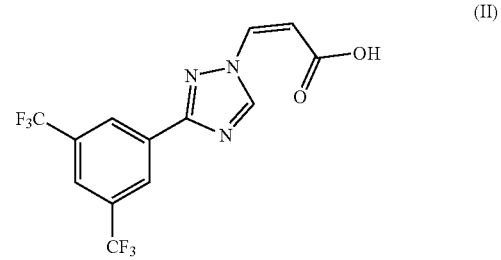

and a compound of Structural Formula III:

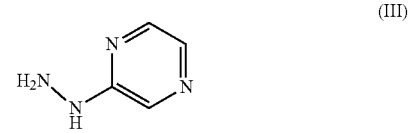

to form a reaction mixture;
cooling the reaction mixture to from about −80° C. to about 0° C.;
treating the reaction mixture with propylphosphonic anhydride to provide a mixture comprising the compound of Structural Formula I; and
isolating the compound of Structural Formula I from the mixture.

"Trialkylamine," as used herein, means $N(R)_3$, wherein each R is independently selected from $C_1$-$C_4$ alkyl. Exemplary triethylamines includes triethylamine and diisopropylethylamine. A preferred trialkylamine is diisopropylethylamine.

In some aspects of the eleventh embodiment, the method comprises cooling the reaction mixture to from about −50° C. to about −15° C., more particularly, from about −25° C. to about −20° C.

In some aspects of the eleventh embodiment, isolating the compound of Structural Formula I from the mixture comprises adding an aqueous quench solution to the mixture comprising the compound of Structural Formula I and performing an extractive work-up of the resulting quenched reaction mixture. For example, an aqueous quench solution of water or a neutral (e.g., pH 7) buffer, such as phosphate buffer, preferably water, can be added to the reaction mixture, and an extractive work-up of the resulting quenched reaction mixture performed.

Methods of performing extractive work-ups are within the skill of one of ordinary skill in the art. For example, an extractive work-up of the reaction mixture comprising the compound of Structural Formula I can include separating the aqueous and organic layers resulting from the addition of the aqueous quench solution to the reaction mixture and, optionally, washing the organic layer, for example, with a dilute (approximately 6% w/w sodium chloride) brine solution and with water. In some aspects of the eleventh embodiment comprising an extractive work-up, the extractive work-up comprises washing the quenched reaction mixture with an aqueous solution of sodium chloride.

Isolating the compound of Structural Formula I from the reaction mixture can alternatively or further include any of the techniques and methods for isolating crystalline forms of the compound of Structural Formula I described above with respect to the seventh, eighth, ninth and tenth embodiments.

It will be understood that, although described independently of one another, the methods described in embodiments ten and eleven can be performed in sequence (i.e., eleven then ten) to prepare single crystalline Form B, C or D of the compound of Structural Formula I or a mixture comprising two or more of crystalline Form B, C or D of the compound of Structural Formula I. It will also be understood that, although described independently of one another, the methods described in embodiments seven or nine, ten and eleven can be performed in sequence (i.e., eleven, then ten, then seven or nine) to prepare single crystalline Form A of the compound of Structural Formula I.

Thus, in some aspects of the tenth embodiment, including the tenth embodiment and any aspect thereof described hereinabove, the method further comprises combining a trialkylamine, 2-methyltetrahydrofuran, a compound of Structural Formula II and a compound of Structural Formula III to form a reaction mixture; cooling the reaction mixture to from about −80° C. to about 0° C.; treating the reaction mixture with propylphosphonic anhydride to provide a mixture comprising the compound of Structural Formula I; and isolating the compound of Structural Formula I from the mixture. Alternative conditions for these further steps, including further details related to the trialkylamine, the temperature of the reaction mixture and the isolation of the compound of Structural Formula I, can be found in the eleventh embodiment, or any aspect thereof.

In some aspects of the seventh, eighth and ninth embodiments, including the seventh embodiment, the eighth embodiment, the ninth embodiment and any aspect of the foregoing, the method further comprises combining a trialkylamine, 2-methyltetrahydrofuran, a compound of Structural Formula II and a compound of Structural Formula III to form a reaction mixture; cooling the reaction mixture to from about −80° C. to about 0° C.; treating the reaction mixture with propylphosphonic anhydride to provide a mixture comprising the compound of Structural Formula I; isolating the compound of Structural Formula I from the reaction mixture; dissolving the isolated compound of Structural Formula I in a solvent system comprising acetonitrile; and inducing formation of solid particles of crystalline Form D of the compound of Structural Formula I and isolating the solid particles of crystalline Form D to obtain single crystalline Form B, C or D of the compound of Structural Formula I or a mixture comprising two or more of crystalline Form B, C or D of the compound of Structural Formula I. Alternative conditions for these further steps, including further details related to the trialkylamine, the temperature of the reaction mixture, the isolation of the compound of Structural Formula I, the solvent system and inducing formation and isolating solid particles of crystalline Form D, can be found in the tenth and eleventh embodiments, or any aspect of the foregoing. Characteristics and alternative characteristics for single crystalline Form D, including alternative XRPD, DSC and/or TGA characteristics, are as described above with respect to the second embodiment.

An twelfth embodiment provides a method of preparing a single crystalline form of a compound represented by Structural Formula I wherein the single crystalline form is Form A and is characterized by at least three X-ray powder diffraction peaks at 2θ angles selected from 4.4°, 19.9°, 21.3° and 22.0°. The method comprises:

(a) combining a trialkylamine, 2-methyltetrahydrofuran, a compound of Structural Formula II:

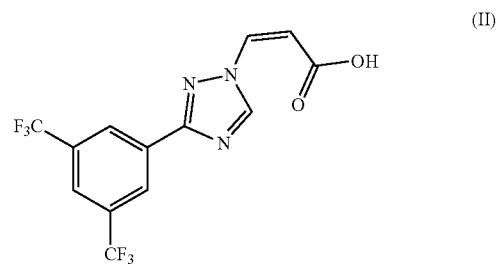 [SMILES: O=C(O)/C=C\n1cnc(-c2cc(C(F)(F)F)cc(C(F)(F)F)c2)n1]

(II)

and a compound of Structural Formula III:

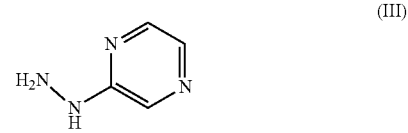

(III)

to form a reaction mixture;
(b) cooling the reaction mixture to from about −80° C. to about 0° C.;
(c) treating the reaction mixture with propylphosphonic anhydride to provide a mixture comprising the compound of Structural Formula I;
(d) isolating the compound of Structural Formula I from the mixture;
(e) dissolving the isolated compound of Structural Formula I in a solvent system comprising acetonitrile;

(f) inducing formation of solid particles of crystalline Form D of the compound of Structural Formula I and isolating the solid particles of crystalline Form D to obtain single crystalline Form D of the compound of Structural Formula I, or solid particles of single crystalline Form B or C of Structural Formula I or a mixture comprising two or more of single crystalline Form B, C or D of the compound of Structural Formula I wherein single crystalline Form D is characterized by at least three X-ray powder diffraction peaks at 2θ angles selected from 3.7°, 7.3°, 10.9°, 18.3° and 21.9°, Form B is characterized by at least three X-ray powder diffraction peaks at 2θ angles selected from 9.4°, 11.1°, 16.5°, 18.3° and 18.8°. Single crystalline Form B is characterized by at least three X-ray diffraction peaks at 2θ angles selected from 3.7°, 11.2°, 12.1° and 18.6°;

(g) heating single crystalline Form D, or single crystalline Form B or C of Structural Formula I or a mixture comprising two or more single crystalline forms of the compound of Structural Formula I, and inducing formation of solid particles of crystalline Form A; or maturing single crystalline Form D, or single crystalline Form B or C of Structural Formula I or a mixture comprising two or more of single crystalline Form B, C or D of the compound of Structural Formula I, in a solvent system and inducing formation of solid particles of crystalline Form A; or drying single crystalline Form D or single crystalline Form B or C of Structural Formula I or a mixture comprising two or more of single crystalline Form B, C or D of the compound of Structural Formula I, thereby forming solid particles of crystalline Form A; or any combination of the foregoing; and (h) isolating the particles of crystalline Form A, thereby preparing single crystalline Form A of the compound of Structural Formula I. Conditions and alternative conditions for the steps can be found in the ninth, tenth and eleventh embodiments, or any aspect of the foregoing. Characteristics and alternative characteristics for single crystalline Form A and single crystalline Forms B, C and D, including alternative XRPD, DSC and/or TGA characteristics, are as described above with respect to the other embodiments.

A thirteenth embodiment provides a method of preparing a single crystalline form of a compound represented by Structural Formula I wherein the single crystalline form is Form A and is characterized by at least three X-ray powder diffraction peaks at 2θ angles selected from 4.4°, 19.9°, 21.3° and 22.0°. The method comprises:

(a) combining a trialkylamine, 2-methyltetrahydrofuran, a compound of Structural Formula II:

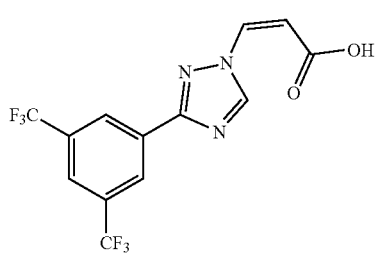

(II)

and a compound of Structural Formula III:

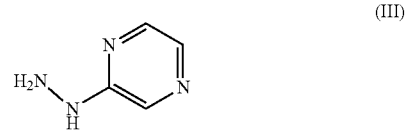

(III)

to form a reaction mixture;

(b) cooling the reaction mixture to from about −80° C. to about 0° C.;

(c) treating the reaction mixture with propylphosphonic anhydride to provide a mixture comprising the compound of Structural Formula I;

(d) exchanging solvent of the reaction mixture comprising the compound of Structural Formula I for a solvent system comprising acetonitrile;

(e) inducing formation of solid particles of crystalline Form D of the compound of Structural Formula I and isolating the solid particles of crystalline Form D to obtain single crystalline Form D of the compound of Structural Formula I, or solid particles of single crystalline Form B or C of Structural Formula I or a mixture comprising two or more of single crystalline Form B, C or D of the compound of Structural Formula I wherein single crystalline Form D is characterized by at least three X-ray powder diffraction peaks at 2θ angles selected from 3.7°, 7.3°, 10.9°, 18.3° and 21.9°, Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°;

(f) heating single crystalline Form D, or single crystalline Form B or C of Structural Formula I or a mixture comprising two or more of single crystalline Form B, C or D of the compound of Structural Formula I, and inducing formation of solid particles of crystalline Form A; or maturing single crystalline Form D, or single crystalline Form B or C of Structural Formula I or a mixture comprising two or more of single crystalline Form B, C or D of the compound of Structural Formula I, in a solvent system and inducing formation of solid particles of crystalline Form A; or drying single crystalline Form D or single crystalline Form B or C of Structural Formula I or a mixture comprising two or more single of crystalline Form B, C or D of the compound of Structural Formula I, thereby forming solid particles of crystalline Form A; or any combination of the foregoing; and (g) isolating the particles of crystalline Form A, thereby preparing single crystalline Form A of the compound of Structural Formula I. Conditions and alternative conditions for the steps can be found in the ninth, tenth and eleventh embodiments, or any aspect of the foregoing. Characteristics and alternative characteristics for single crystalline Form A and single crystalline Forms B, C and D, including alternative XRPD, DSC and/or TGA characteristics, are as described above with respect to other embodiments.

Distilligraphic exchange is a suitable solvent exchange method for any embodiments having a solvent exchange step.

A fourteenth embodiment provides a method for preparing a composition comprising particles of a single crystalline form of a compound represented by Structural Formula I wherein the single crystalline form is Form A and is characterized by at least three X-ray powder diffraction peaks at 2θ angles selected from 4.4°, 19.9°, 21.3° and 22.0°; and the particles have a particle size distribution characterized by a d(0.9) of less than about 70 microns. In some aspects of the fourteenth embodiment, the particles have a particle size distribution characterized by a d(0.9) of less than about 100 microns.

In some embodiments, the method comprises:
(a) combining a trialkylamine, 2-methyltetrahydrofuran, a compound of Structural Formula II:

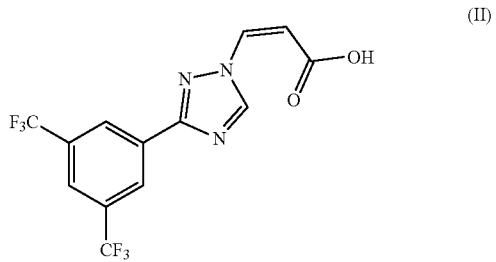 [SMILES: O=C(O)/C=C\n1cnc(-c2cc(C(F)(F)F)cc(C(F)(F)F)c2)n1]

and a compound of Structural Formula III:

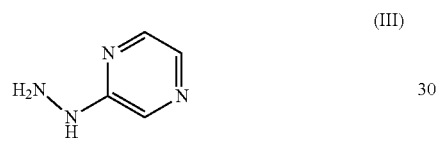

to form a reaction mixture;
(b) cooling the reaction mixture to from about −80° C. to about 0° C.;
(c) treating the reaction mixture with propylphosphonic anhydride to provide a mixture comprising the compound of Structural Formula I;
(d) isolating the compound of Structural Formula I from the mixture;
(e) dissolving the isolated compound of Structural Formula I in a solvent system comprising acetonitrile;
(f) inducing formation of solid particles of crystalline Form D of the compound of Structural Formula I and isolating the solid particles of crystalline Form D to obtain single crystalline Form D of the compound of Structural Formula I, or solid particles of single crystalline Form B or C of Structural Formula I or a mixture comprising two or more of single crystalline Form B, C or D of the compound of Structural Formula I wherein single crystalline Form D is characterized by at least three X-ray powder diffraction peaks at 2θ angles selected from 3.7°, 7.3°, 10.9°, 18.3° and 21.9°, Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°;
(g) suspending single crystalline Form B, C or D of the compound of Structural Formula I or a mixture comprising two or more of single crystalline Form B, C or D of the compound of Structural Formula I, in isopropanol or a mixture of isopropanol and water to form a slurry; (h) heating the slurry to a temperature less than or equal to about 70° C. to form a second slurry or a solution;
(i) cooling the second slurry or the solution and adding water to the second slurry or the solution, thereby forming solid particles of crystalline Form A of the compound of Structural Formula I; and
(j) isolating the solid particles of crystalline Form A, thereby preparing a composition comprising particles of single crystalline From A of the compound of Structural Formula I.

In some embodiments, the method comprises:
(a) combining a trialkylamine, 2-methyltetrahydrofuran, a compound of Structural Formula II:

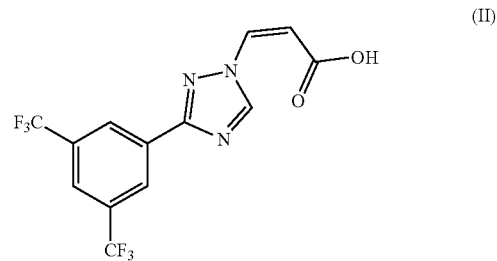

and a compound of Structural Formula III:

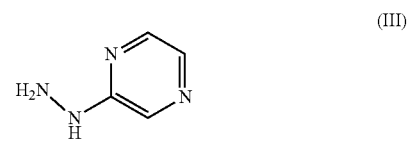

to form a reaction mixture;
(b) cooling the reaction mixture to from about −80° C. to about 0° C.;
(c) treating the reaction mixture with propylphosphonic anhydride to provide a mixture comprising the compound of Structural Formula I;
(d) exchanging solvent of the reaction mixture comprising the compound of Structural Formula I for a solvent system comprising acetonitrile;
(e) inducing formation of solid particles of crystalline Form D of the compound of Structural Formula I and isolating the solid particles of crystalline Form D to obtain single crystalline Form D of the compound of Structural Formula I, or solid particles of single crystalline Form B or C of Structural Formula I or a mixture comprising two or more of single crystalline Form B, C or D of the compound of Structural Formula I wherein single crystalline Form D is characterized by at least three X-ray powder diffraction peaks at 2θ angles selected from 3.7°, 7.3°, 10.9°, 18.3° and 21.9°, Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°;
(f) suspending single crystalline Form D, or single crystalline Form B or C of the compound of Structural Formula I or a mixture comprising two or more of single crystalline Form B, C or D of the compound of Structural Formula I, in isopropanol or a mixture of isopropanol and water to form a slurry;
(g) heating the slurry to a temperature less than or equal to about 70° C. to form a second slurry or a solution;

(h) cooling the second slurry or the solution and adding water to the second slurry or the solution, thereby forming solid particles of crystalline Form A of the compound of Structural Formula I; and (i) isolating the solid particles of crystalline Form A, thereby preparing a composition comprising particles of single crystalline From A of the compound of Structural Formula I.

In some embodiments, the method comprises:

(a) combining a trialkylamine, 2-methyltetrahydrofuran, a compound of Structural Formula II:

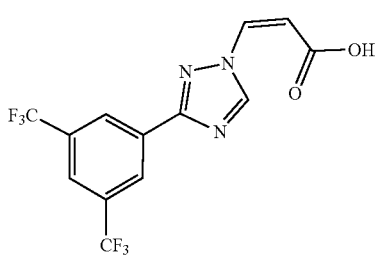

and a compound of Structural Formula III:

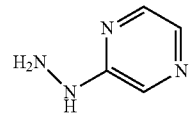

to form a reaction mixture;

(b) cooling the reaction mixture to from about −80° C. to about 0° C.;

(c) treating the reaction mixture with propylphosphonic anhydride to provide a mixture comprising the compound of Structural Formula I;

(d) isolating the compound of Structural Formula I from the mixture;

(e) dissolving the isolated compound of Structural Formula I in a solvent system comprising acetonitrile;

(f) inducing formation of solid particles of crystalline Form D of the compound of Structural Formula I and isolating the solid particles of crystalline Form D to obtain single crystalline Form D of the compound of Structural Formula I, or solid particles of single crystalline Form B or C of Structural Formula I or a mixture comprising two or more of single crystalline Form B, C or D of the compound of Structural Formula I wherein single crystalline Form D is characterized by at least three X-ray powder diffraction peaks at 2θ angles selected from 3.7°, 7.3°, 10.9°, 18.3° and 21.9°, Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°;

(g) suspending single crystalline Form D, or single crystalline Form B or C of the compound of Structural Formula I or a mixture comprising two or more of crystalline Form B, C or D of the compound of Structural Formula I, in isopropanol or a mixture of isopropanol and water to form a slurry;

(h) heating the slurry to a temperature less than or equal to about 70° C. to form a second slurry or a solution;

(i) adding water to the second slurry or the solution and cooling the second slurry or the solution, thereby forming solid particles of crystalline Form A of the compound of Structural Formula I; and (j) isolating the solid particles of crystalline Form A, thereby preparing a composition comprising particles of single crystalline Form A of the compound of Structural Formula I. Conditions and alternative conditions for the steps can be found in the seventh, eighth, tenth and eleventh embodiments, or any aspect of the foregoing. Characteristics and alternative characteristics for single crystalline Form A and single crystalline Form D, including alternative XRPD, DSC and/or TGA characteristics, are as described above with respect to the first and second embodiments, respectively.

In some embodiments In some embodiments, the method comprises:

(a) combining a trialkylamine, 2-methyltetrahydrofuran, a compound of Structural Formula II:

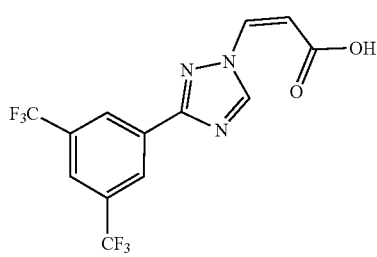

and a compound of Structural Formula III:

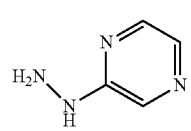

to form a reaction mixture;

(b) cooling the reaction mixture to from about −80° C. to about 0° C.;

(c) treating the reaction mixture with propylphosphonic anhydride to provide a mixture comprising the compound of Structural Formula I;

(d) exchanging solvent of the reaction mixture comprising the compound of Structural Formula I for a solvent system comprising acetonitrile;

(e) inducing formation of solid particles of crystalline Form D of the compound of Structural Formula I and isolating the solid particles of crystalline Form D to obtain single crystalline Form D of the compound of Structural Formula I, or solid particles of single crystalline Form B or C of Structural Formula I or a mixture comprising two or more of single crystalline Form B, C or D of the compound of Structural Formula I wherein single crystalline Form D is characterized by at least three X-ray powder diffraction peaks at 2θ angles selected from 3.7°, 7.3°, 10.9°, 18.3° and 21.9°, Form B is characterized by at least three X-ray powder diffraction peaks at 2θ angles selected from 9.4°, 11.1°, 16.5°, 18.3° and 18.8°. Single crystalline Form C is characterized by at least three X-ray diffraction peaks at 2θ angles selected from 3.7°, 11.2°, 12.1° and 18.6°;

(f) suspending single crystalline Form D, or single crystalline Form B or C of the compound of Structural Formula I or a mixture comprising two or more of crystalline Form B, C or D of the compound of Structural Formula I, in isopropanol or a mixture of isopropanol and water to form a slurry;

(g) heating the slurry to a temperature less than or equal to about 70° C. to form a second slurry or a solution;

(h) adding water to the second slurry or the solution and cooling the second slurry or the solution, thereby forming solid particles of crystalline Form A of the compound of Structural Formula I; and (i) isolating the solid particles of crystalline Form A, thereby preparing a composition comprising particles of single crystalline Form A of the compound of Structural Formula I.

EXEMPLIFICATION

Example 1. Preparation of Selinexor Lot No. 1305365 (Form A)

Selinexor for Lot No. 1305365 was made in accordance with the following reaction scheme:

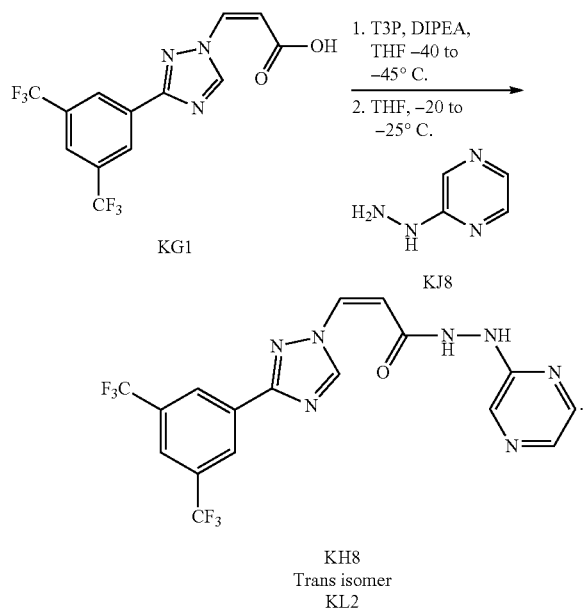

A solution of propane phosphonic acid anhydride (T3P®, 50% in ethyl acetate, 35 Kg) in THF (24.6 Kg) was cooled to about −40° C. To this solution was added a solution of KG1 (13.8 Kg) and diisopropylethylamine (12.4 Kg) in tetrahydrofuran (THF, 24.6 Kg). The resulting mixture was stirred at about −40° C. for approximately 2.5 hours.

In a separate vessel, KJ8 (4.80 Kg) was mixed with THF (122.7 Kg), and the resulting mixture cooled to about −20° C. The cold activated ester solution was then added to the KJ8 mixture with stirring, and the reaction was maintained at about −20° C. The mixture was warmed to about 5° C., water (138.1 Kg) was added and the temperature adjusted to about 20° C. After agitating for about an hour, the lower phase was allowed to separate from the mixture and discarded. The upper layer was diluted with ethyl acetate (EtOAc). The organic phase was then washed three times with potassium phosphate dibasic solution (~150 Kg), then with water (138.6 Kg).

The resulting organic solution was concentrated under reduced pressure to 95 L, EtOAc (186.6 Kg) was added and the distillation repeated to a volume of 90 L. Additional EtOAc (186.8 Kg) was added and the distillation repeated a third time to a volume of 90 L. The batch was filtered to clarify, further distilled to 70 L, then heated to about 75° C., and slowly cooled to 0 to 5° C. The resulting slurry was filtered and the filter cake washed with a mixture of EtOAc (6.3 Kg) and toluene (17.9 Kg) before being dried in a vacuum oven to provide selinexor designated Lot No. 1305365 (Form A).

Example 2. Preparation of Selinexor Lot No. 1341-AK-109-2 (Form A)

The acetonitrile solvate of selinexor was prepared in accordance with Example 6.

The acetonitrile solvate of selinexor (2.7 g) was suspended in a mixture of isopropanol (IPA, 8 mL) and water (8 mL), and the resulting mixture heated to 65 to 70° C. to effect dissolution. The solution was cooled to 45° C., and water (28 mL) was added over 15 minutes, maintaining the temperature between 40 and 45° C. The slurry was cooled to 20 to 25° C. over an hour, then further cooled to 0 to 5° C. and held at that temperature for 30 minutes before being filtered. The filter cake was washed with 20% v/v IPA in water and the product dried under suction overnight, then in vacuo (40° C.).

Example 3. Preparation of Selinexor Lot No. PC-14-005 (Form A)

The acetonitrile solvate of selinexor (Form D) was prepared in accordance with the procedure described in Example 6.

The acetonitrile solvate of selinexor (1.07 Kg) was suspended in a mixture of IPA (2.52 Kg) and water (3.2 Kg) and the mixture heated to 70 to 75° C. to dissolve. The temperature was then adjusted to 40 to 45° C. and held at that temperature for 30 minutes. Water (10.7 Kg) was added while maintaining the temperature at 40 to 45° C., then the batch was cooled to 20 to 25° C. and agitated at that temperature for 4 hours before being further cooled to 0 to 5° C. After a further hour of agitation, the slurry was filtered and the filter cake washed with a cold mixture of IPA (0.84 Kg) and water (4.28 Kg) before being dried.

Example 4. Preparation of Selinexor Lot No. PC-14-009 (Form A)

The acetonitrile solvate of selinexor (Form D) was prepared in accordance with the procedure described in Example 6.

The acetonitrile solvate of selinexor (1.5 Kg) was suspended in IPA (3.6 Kg) and water (4.5 Kg) and warmed to 37 to 42° C. with gentle agitation. The suspension was agitated at that temperature for 4 hours, and was then cooled to 15 to 20° C. over 1 hour. Water (15.1 Kg) was added, maintaining the temperature, then the agitation was continued for 1 hour and the batch was filtered. The filter cake was washed with a mixture of IPA (1.2 Kg) and water (6 Kg), then dried under a flow of nitrogen.

Example 5. Preparation of Selinexor Lot Nos. 1339-BS-142-1, 1339-BS-142-2 and PC-14-008 (Form A)

A reactor, under nitrogen, was charged with KG1 (1 Kg, 1.0 Eq), KJ8 (0.439 Kg, 1.4 Eq) and MeTHF (7 L, 7 parts with respect to KG1). Diisopropylethylamine (0.902 Kg, 2.45 Eq with respect to KG1) was added to the reaction mixture at −20° C. to −25° C. with a MeTHF rinse. To the reaction mixture, 50% T3P® in ethyl acetate (2.174 Kg, 1.2 Eq with respect to KG1) was then charged, maintaining the temperature at −20° C. to −25° C. with a MeTHF rinse. After the completion of the addition, the reaction mixture was stirred briefly and then warmed to 20° C. to 25° C. Upon completion, the reaction mixture was washed first with water (5 L, 5 parts with respect to KG1) and then with dilute brine (5 L, 5 parts with respect to KG1). The organic layer was concentrated by vacuum distillation to a volume of 5 L (5 parts with respect to KG1), diluted with acetonitrile (15 L, 15 parts with respect to KG1) at approximately 40° C. and concentrated again (5 L, 5 parts with respect to KG1). After solvent exchange to acetonitrile, the reaction mixture was then heated to approximately 60° C. to obtain a clear solution. The reaction mixture was then cooled slowly to 0-5° C., held briefly and filtered. The filter cake was washed with cold acetonitrile (2 L, 5 parts with respect to KG1) and the filter cake was then dried under a stream of nitrogen to provide the acetonitrile solvate of selinexor (Form D) as a slightly off-white solid.

Form D of selinexor (0.9 Kg) was suspended in IPA (2.1 Kg, 2.7 L, 3 parts with respect to Form D) and water (2.7 Kg, 2.7 L, 3 parts with respect to Form D) and warmed to approximately 40° C. The resulting suspension was agitated for about 4 hours, selinexor, cooled to approximately 20° C., and diluted with additional water (9 Kg, 10 parts with respect to Form D). The mixture was stirred for a further 4-6 hours, then filtered, and the cake washed with a mixture of 20% IPA and water (4.5 L, 5 parts with respect to Form D). The filter cake was then dried under vacuum to provide selinexor designated Lot No. PC-14-008 as a white crystalline powder with a >99.5% a/a UPLC purity (a/a=area to area of all peaks; UPLC-ultra performance HPLC).

Example 6. Preparation of Selinexor Lot No. 1405463 (Form A)

Selinexor Lot No. 1405463 was prepared in accordance with the following reaction scheme:

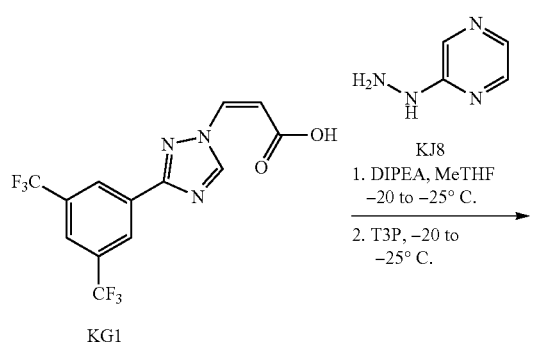

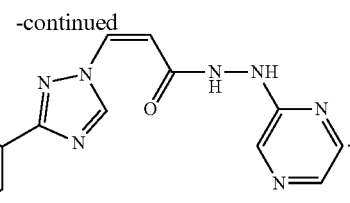

KH8
Trans isomer
KL2

A reactor was charged with KG1 (15.8 Kg), KJ8 (6.9 Kg) and MeTHF (90 Kg). Diisopropylethylamine (14.2 Kg) was added to the reaction mixture over approximately 35 minutes at about −20° C. Following the addition of the diisopropylethylamine, T3P® (50% solution in EtAOc, 34.4 Kg) was added maintaining the temperature at −20° C. The mixture stirred to complete the reaction first at −20° C., then at ambient temperature.

Upon completion of the reaction, water (79 Kg) was added over about 1 hour. The layers were separated and the organic layer was washed with a mixture of water (55 Kg) and brine (18 Kg), The mixture was filtered, and the methyl-THF/ethyl acetate in the mixture distillatively replaced with acetonitrile (volume of approximately 220 L). The mixture was warmed to dissolve the solids, then slowly cooled to 0 to 5° C. before being filtered. The filter cake was washed with acetonitrile to provide the acetonitrile solvate of selinexor (Form D).

The acetonitrile solvate of selinexor was dried, then mixed with isopropanol (23 Kg) and water (55 Kg). The slurry was warmed to about 38° C. and held at that temperature for approximately 4 hours before being cooled to 15 to 20° C. Water (182 Kg) was added. After a further 5 hours of agitation, the mixture was filtered and the filter cake washed with a mixture of isopropanol (14 Kg) and water (73 Kg), before being dried under vacuum (45° C.). The dried product was packaged to provide selinexor Lot No. 1405463 (Form A).

Example 7. Polymorphism Studies of Selinexor

A comprehensive polymorphism assessment of selinexor was performed in a range of different solvents, solvent mixtures and under a number of experimental conditions based on the solubility of selinexor. Three anhydrous polymorphs of selinexor were observed by XRPD investigation, designated Form A, Form B and Form C. Form A is a highly crystalline, high-melting form, having a melting point of 177° C., and was observed to be stable from a physicochemical point of view when exposed for 4 weeks to 25° C./97% relative humidity (RH) and to 40° C./75% RH. A solvated form of selinexor was also observed in acetonitrile, designated Form D. A competitive slurry experiment confirmed Form A as the stable anhydrous form under the conditions investigated, except in acetonitrile, in which solvate formation was observed. It was further found that in acetonitrile, below 50° C., only Form D is observed, at 50° C. both Form A and Form D are observed, and at 55° C., Form A is observed.

General Instrument and Methodology Details

X-Ray Powder Diffraction (XRPD)

Bruker AXS C2 GADDS: XRPD patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate).

The beam divergence, i.e., the effective size of the X-ray beam on the sample, was approximately 4 mm. A θ-θ continuous scan mode was employed with a sample detector distance of 20 cm which gives an effective 2θ range of 3.2°-29.7°. Typically, the sample would be exposed to the X-ray beam for 120 seconds. The software used for data collection was GADDS for XP/2000 4.1.43 and the data were analyzed and presented using Diffrac Plus EVA v13.0.0.2 or v15.0.0.0.

Ambient conditions. Samples run under ambient conditions were prepared as flat plate specimens using powder as received without grinding. Approximately 1-2 mg of the sample was lightly pressed on a glass slide to obtain a flat surface.

Non-ambient conditions. Samples run under non-ambient conditions were mounted on a silicon wafer with heat-conducting element. The sample was then heated to the appropriate temperature and data collection was initiated.

Bruker AXS D8 Advance. XRPD patterns were collected on a Bruker D8 diffractometer using Cu Kα radiation (40 kV, 40 mA), 0-20 goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analyzed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42 °2θ

Step size: 0.05 °2θ

Collection time: 0.5 s/step.

Differential Scanning Calorimetry (DSC)

Mettler DSC 823e. DSC data were collected on a Mettler DSC 823E equipped with a 34 position auto-sampler. The instrument was calibrated for energy and temperature using certified indium. Typically, 0.5-3 mg of each sample, in a pin-holed aluminum pan, was heated at 10° C./minute from 25° C. to 300° C. A nitrogen purge at 50 ml/min was maintained over the sample. The instrument control and data analysis software was STARe v9.20.

Thermogravimetric Analysis (TGA)

Mettler TGA/SDTA 851e. TGA data were collected on a Mettler TGA/SDTA 851e equipped with a 34 position auto-sampler. The instrument was temperature calibrated using certified indium. 5-30 mg of each sample was loaded onto a pre-weighed aluminum crucible and was heated at 10° C./min from ambient temperature to 350° C. A nitrogen purge at 50 ml/min was maintained over the sample. The instrument control and data analysis software was STARe v9.20.

Chemical Purity Determination by High Performance Liquid Chromatography (HPLC)

Purity analysis was performed on an Agilent HP1100 series system equipped with a diode array detector using ChemStation software vB.02.01-SR1 (or SR2) as follows:

| Sample Preparation | ~0.4 mg/mL in 1:1 ACN/MeOH |
|---|---|
| Column | Zorbax SB-Phenyl, 4.6 mm × 150 mm, 5 µm |
| Column Temperature (° C.) | 40 |
| Injection (µl) | 10 |
| Detection: Wavelength, Bandwidth (nm) | 245 nm |
| Flow Rate (ml/min) | 1.0 |
| Phase A | 20 mM Ammonium Acetate in Water (no pH specified) |
| Phase B | 70% ACN, 30% MeOH (v/v) |

Solubility Assessment

The polymorphism assessment of selinexor included a solubility assessment, performed on Form A. About 20 mg of selinexor prepared in accordance with the process described in Example 1 were weighed into vials and the solubility was visually assessed at 50° C. in thirty solvents and solvent mixtures. After each solvent addition, samples were kept under agitation for 10 minutes at 50° C. before each assessment; the samples were then left to cool to room temperature (RT) before a second assessment was done at RT. Samples/conditions that fully dissolved were designated as soluble, samples that showed signs of partial solubility (thinning, notably less solids) were designated partially soluble (PS) and conditions lacking visual signs of solubility were designated insoluble. Three further solubility assessments were performed in IPA:water, MeCN:water and MTBE:heptane mixtures. Note: solubility was assessed within 5 and 100 volumes for the different solvents used. 1 volume (in µL) is equal to the sample mg used in the assessment (e.g., for a 20 mg sample, 1 volume is equal to 20 µL).

Selinexor was soluble in about 60% of the solvent systems investigated. selinexor was not soluble in heptane, 1,2-dichloroethane, toluene, cumene, diisopropylether, water and isooctane. selinexor was also soluble in IPA:water mixtures having up to 60% water and in acetonitrile:water mixtures having up to 40% water in the mixture. Selinexor was not found to be soluble in up to 100 volumes of any of the MTBE:heptane mixtures investigated.

Polymorphism Studies

The samples produced during the solubility assessment were processed as follows:

The clear solutions obtained were placed for cooling at 5° C. and eventually at −20° C. for at least 12 hours (−20° C. step was introduced or not depending on the 5° C. result and on the nature of the solvent). Samples found as clear solutions at −20° C. were placed for slow evaporation at RT using a 25-gauge syringe needle(s) in the septum of the vial.

The solid suspensions observed in 100 volumes of the relative solvent systems at the end of the solubility assessment were placed for 8 days maturation cycling between RT and 50° C. (cycling 4 hours at RT; 4 hours at 50° C.). After the maturation, the solids were recovered and the supernatants were placed for slow evaporation.

All the solids obtained by these processes were analyzed by XRPD.

Most of the solids recovered from the processed samples were found to be consistent with Form A (76% of the hits).

The X-ray diffractogram of Form A is depicted in FIG. 1A. Representative XRPD peaks for Form A depicted in FIG. 1A are as follows:

| 2-Theta ° | Intensity % |
|---|---|
| 4.4 | 50.9 |
| 12.4 | 19.9 |
| 13.1 | 23.3 |
| 14.5 | 8.7 |
| 14.7 | 13.1 |
| 15.8 | 23.6 |
| 16.9 | 8.0 |
| 17.5 | 7.9 |
| 18.2 | 22.2 |
| 19.9 | 100.0 |
| 20.3 | 47.0 |
| 21.3 | 85.6 |
| 22.0 | 58.1 |
| 23.1 | 16.2 |
| 23.5 | 43.1 |
| 23.7 | 37.5 |
| 23.9 | 13.6 |
| 25.0 | 44.8 |
| 25.3 | 10.0 |
| 25.6 | 13.6 |
| 27.0 | 21.4 |
| 27.3 | 11.5 |
| 28.3 | 28.6 |
| 28.5 | 31.3 |
| 31.4 | 19.1 |
| 34.8 | 11.3 |
| 37.2 | 13.6 |

The starting anhydrous form (Form A) was found to be stable in most of the conditions investigated and no other anhydrous forms were observed to form under solvent-based experimentation. By TGA, 0.4% w/w of weight loss was observed between 160° C. and 200° C. DSC analysis showed an endothermic event at 177° C. due to the melting of the sample (melting was also observed by VT-XRPD). The DSC and TGA thermograms of Form A are depicted in FIG. 1B.

In MeCN, Form A was observed to convert to a solvated form, designated Form D (MeCN solvate). The X-ray powder diffractogram of Form D is depicted in FIG. 2A. Representative XRPD peaks for Form D depicted in FIG. 2A are as follows:

| 2-Theta ° | Intensity % |
|---|---|
| 3.7 | 51.7 |
| 7.3 | 85.9 |
| 9.7 | 40.8 |
| 10.9 | 32.5 |
| 11.1 | 24.6 |
| 13.1 | 8.8 |
| 18.3 | 38.0 |
| 19.2 | 35.5 |
| 19.5 | 23.7 |
| 20.4 | 6.0 |
| 20.6 | 21.2 |
| 21.9 | 100.0 |
| 22.3 | 9.8 |
| 22.5 | 9.7 |
| 23.9 | 5.3 |
| 24.4 | 7.4 |
| 26.8 | 6.8 |
| 28.9 | 8.4 |
| 29.3 | 3.7 |
| 29.5 | 3.4 |
| 30.1 | 3.8 |
| 31.9 | 7.1 |
| 32.5 | 3.1 |
| 33.1 | 3.1 |
| 33.7 | 4.4 |
| 38.1 | 3.0 |
| 41.3 | 4.1 |

Form D was also observed in acetonitrile-water mixtures of greater than 20% v/v MeCN in water. In 20% v/v MeCN in water, the solid recovered was consistent with Form A by XRPD. These results are described in Table 1.

TABLE 1

| Solvent | Solubility | Experiment | Result | XRPD |
|---|---|---|---|---|
| Acetonitrile | Dissolved in 70v | Placed at −20° C. | Solid recovered | Form D |
| 90% MeCN:10% Water | Dissolved in 30v | Placed at 5° C. | Solid recovered | Form D |
| 80% MeCN:20% Water | Dissolved in 30v | Placed at 5° C. | Solid recovered | Form D |
| 60% MeCN:40% Water | Dissolved in 50v | Placed at 5° C. | Solid recovered | Form D |
| 40% MeCN: 60% Water | Not dissolved in 100v | Placed for slow evap. | Solid recovered | Form D |
| 20% MeCN:80% Water | Not dissolved in 100v | Matured 25° C.-50° C. | Solid recovered | Form A |

TGA and DSC were performed on a sample of Form D. By TGA, a weight loss of 1.86% w/w was observed due to acetonitrile loss. However, the weight loss by TGA was influenced by preparation timing of the sample after the recovery of the material. By DSC, an endothermic/exothermic event was observed around 152° C. followed by an endothermic event at 177° C. The DSC behavior is similar to that observed for Form C (see below).

A sample of selinexor isolated from MeCN was analyzed by DSC and TGA immediately after recovering from the solvent. A solvent loss of 6.5% w/w was observed by TGA. DSC showed an endothermic event around 77° C. due to the solvent loss followed by endo/exo event of Form C and melting event of Form A around 178° C. The DSC and TGA thermograms of Form D are depicted in FIG. 2B. As mentioned above, the solvent loss observed by TGA can vary depending on the time the sample of Form D is exposed to ambient conditions during sample preparation. A solvent loss of 6.5% corresponds to 0.75 moles of solvent per mole of compound. Although not wishing to be bound by any particular theory, Form D could be a mono-solvate which can be desolvated with drying and is thus sensitive to isolation conditions, as evidenced by the TGA results.

Form D was analyzed by VT-XRPD. Form D was observed to convert to Form C after 80° C. and Form C was observed to convert to Form A. On heating, after the release of the solvent, solvate Form D converts to Form C; the endo/exo event observed by DSC around 152° C. is due to Form C. Moreover, Form D was dried for 15 hours at 80° C. and 3 mbar. The sample recovered was found as consistent with Form C. By HPLC and $^1$H-NMR analysis, the recovered sample (Form C) was found as 99.6% pure, as measured by the area under the curve (AUC), and the compound structure was confirmed. No residual MeCN was observed after heating and drying the sample.

Drying and thermal experiments (including VT-XRPD analysis) were found to convert Form D to anhydrous Forms B and C. The thermal transition of Form B to Form C and the thermal transition of Form C to Form A were observed by DSC. Form D was also observed to convert to Form A upon heating and upon maturation of Form D in a 20% volume/volume (v/v) MeCN in water mixture. However, mixtures of acetonitrile:water with acetonitrile above 20% v/v have shown a conversion of the anhydrous compound to the acetonitrile solvate (Form D).

Form B was analyzed by DSC, TGA, XRPD and variable temperature XRPD (VT-XPRD). The X-ray powder diffractogram for Form B is depicted in FIG. 3A. Representative XRPD peaks for Form B depicted in FIG. 3A are as follows:

| 2-Theta ° | Intensity % |
|---|---|
| 8.1 | 26.1 |
| 9.4 | 100.0 |
| 11.1 | 60.7 |
| 13.8 | 23.3 |
| 16.5 | 50.2 |
| 18.3 | 51.9 |
| 18.8 | 59.8 |
| 20.2 | 47.3 |
| 20.8 | 45.3 |

The DSC and TGA thermograms are depicted in FIG. 3B. This polymorph shows an endothermic melting around 91° C. immediately followed by a recrystallization exotherm. A second endo/exo event is observed around 155° C. followed by an endothermic event at 179° C. By VT-XRPD analysis, it is possible to explain the events observed by DSC: the first endo/exo event at 91° C. is the melting of Form B followed by recrystallization towards Form C; the latter melts around 155° C. and recrystallizes towards Form A, which melts at 179° C. By TGA, no relevant weight losses were observed.

Form C was analyzed by DSC, TGA and XRPD. The X-ray powder diffractogram for Form C is depicted in FIG. 4A. Representative XRPD peaks for Form C depicted in FIG. 4A are as follows:

| 2-Theta ° | Intensity % |
|---|---|
| 3.7 | 100.0 |
| 10.5 | 9.0 |
| 11.2 | 15.4 |
| 12.1 | 15.0 |
| 14.9 | 7.4 |
| 16.4 | 8.6 |
| 17.7 | 13.3 |
| 18.6 | 32.0 |
| 19.7 | 15.4 |
| 21.2 | 14.2 |
| 22.2 | 15.2 |

The DSC and TGA thermograms are depicted in FIG. 4B. By DSC, an endothermic/exothermic event was observed around 155° C., followed by an endothermic event around 179° C. No VT-XRPD analysis was performed for this form but, as per the Form B VT-XRPD experiment, the endo/exo event is due to the melting/recrystallisation of Form C towards Form A; the second endothermic event at 179° C. is the melting of Form A. No significant weight losses were observed by TGA analysis for Form C.

Competitive Slurry Experiment

In a competitive slurry experiment, approximately 1:1 mixtures of Form A and Form C were prepared. The mixtures were then stirred with a seed of Form B (about 5% by weight of the mixture of Form A and Form C). The produced systems were matured at 5° C., 25° C. and 50° C. under stirring in acetonitrile, ethyl acetate, 30% IPA:70% water and 30% ethanol:70% water. The systems were analyzed by XRPD at two different time points: 72 hours and 1 week.

Mixtures matured in ethyl acetate, IPA:water and ethanol:water were found to be consistent with Form A by XRPD. Form D was observed by maturation in acetonitrile. This experiment confirmed Form A as the stable form, compared to Form B and Form C, under the conditions investigated. The presence of acetonitrile led to solvate formation at all of the temperatures investigated.

Example 8. Particle Size Method and Sample Analyses

A particle size method for analysis of samples of selinexor was developed, and a number of samples of selinexor were analyzed using the developed method.

General Instrument and Methodology Details

Polarized Light Microscopy

Polarized light microscopy was performed using a Leica DM LP microscope equipped with a Spot Insight color camera. Crossed-polarized light was used with a first order red compensator. Various objectives were used to view the sample. Images were acquired at ambient temperature using Spot Advanced software (v.4.5.9). Micron bars were added to the images to help estimate particle sizing.

Particle Size Analysis

Particle size data was acquired using a Malvern Instruments MS2000 equipped with a Hydro2000µP dispersion unit. Data was collected and analyzed using Mastersizer 2000 v 5.60 software, using volume-based measurements. NIST-traceable glass beads were used as the reference standard.

Polarized Light Microscopy

Photomicrographs of selinexor Lot No. 1305365 (described in Example 1) dispersed in mineral oil were collected to determine the morphology of the sample to determine if the sample was agglomerated and to gain an initial estimate of the size of the particles. Based both upon observation during analysis and on the obtained images, the sample was composed primarily of blades and acicular particles 10-100 µm in length, some smaller, irregularly-shaped particles and some agglomerates 200-300 µm in length that dispersed easily in mineral oil. Later observations of the sample suspended in various dispersants showed larger agglomerates, but these were also easily dispersed. Table 2 summarizes these observations.

TABLE 2

Polarized Light Microscopy of selinexor Lot No. 1305365.

| Suspension medium | Observations[a] |
|---|---|
| Mineral oil | Blades and acicular particles 10-100 µm, some smaller, irregularly-shaped particles and some agglomerates 200-300 µm. |
| 0.1% (w/v) Lecithin in Isopar G | Blades and acicular particles 10-100 µm, some smaller, irregularly-shaped particles and some very large agglomerates. |
| 0.3% (w/v) Span 85 in heptane | Blades and acicular particles 10-100 µm, some smaller, irregularly-shaped particles and some larger agglomerates. |
| 0.1% (w/v) Tween 20 in water | Blades and acicular particles 10-100 µm, some smaller, irregularly-shaped particles and some larger agglomerates. |

[a]Observations recorded during microscopy and based upon resulting photomicrographs Particle Size Method and Sample Analyses Details of the method conditions used to analyze particle size are listed below:

Sample refractive index: 1.596
Sample absorption: 0.001
Dispersant: 0.1% (w/v) Lecithin in Isopar G
Dispersant refractive index: 1.42
Pump speed: 2100 rpm
Recirculation time: 2 minutes
Sample measurement time: 30 sec.
Background measurement time: 30 sec.
Model: general purpose
Sensitivity: normal
Particle shape: irregular.

The relative standard deviations for the d10, d50 and d90 using these method conditions were 2.35%, 1.28% and 6.17%, respectively. All deviations fall well within the USP recommendation of 30%, 10%, 15% for the d10, d50 and d90, respectively.

One particle size measurement of each lot of selinexor described in Examples 1-6 was collected using the particle size method conditions described above. Table 4 provides sample information and particle size analysis data for the indicated lot of selinexor under the particle size method analysis conditions described above. FIGS. 5A-5P are particle size distribution graphs and show the particle size distribution of the sample corresponding to the indicated lot of selinexor under the particle size method analysis conditions described above.

TABLE 4

Sample Information and Particle Size Analysis of Selinexor Using the Revised Method Conditions.

Figure 5C:
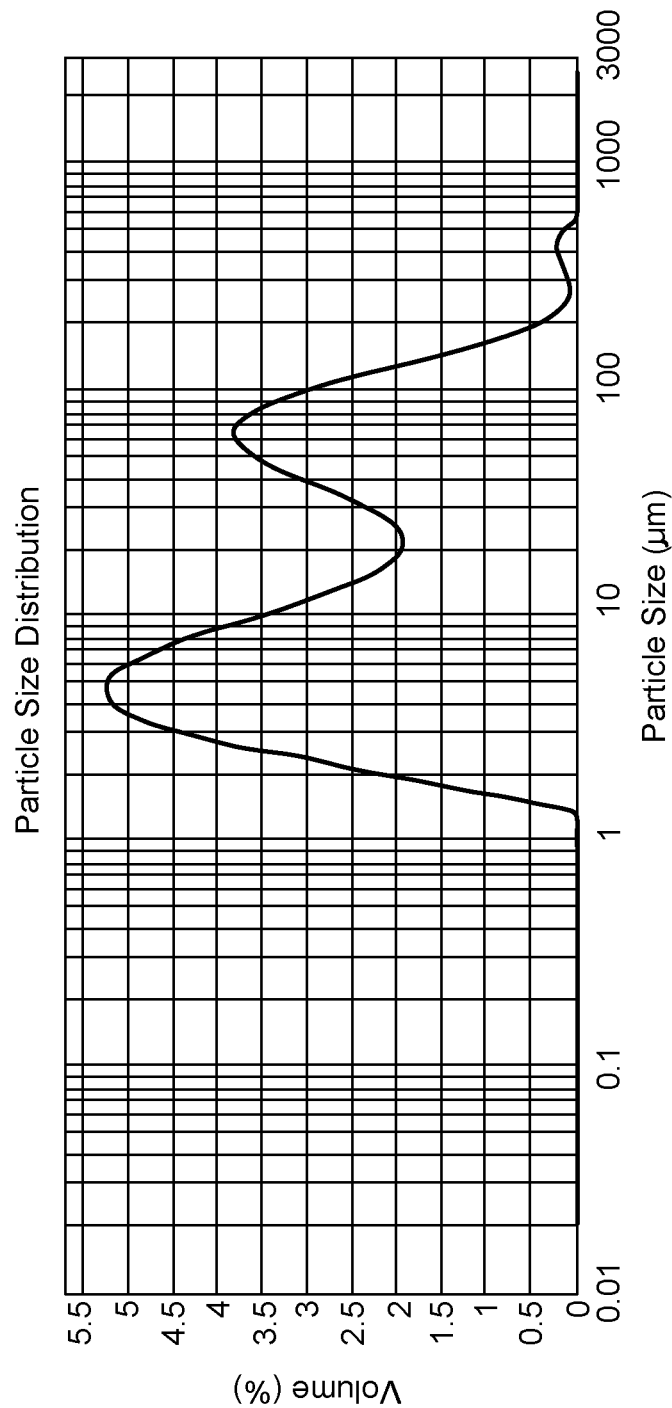
Figure 5E:
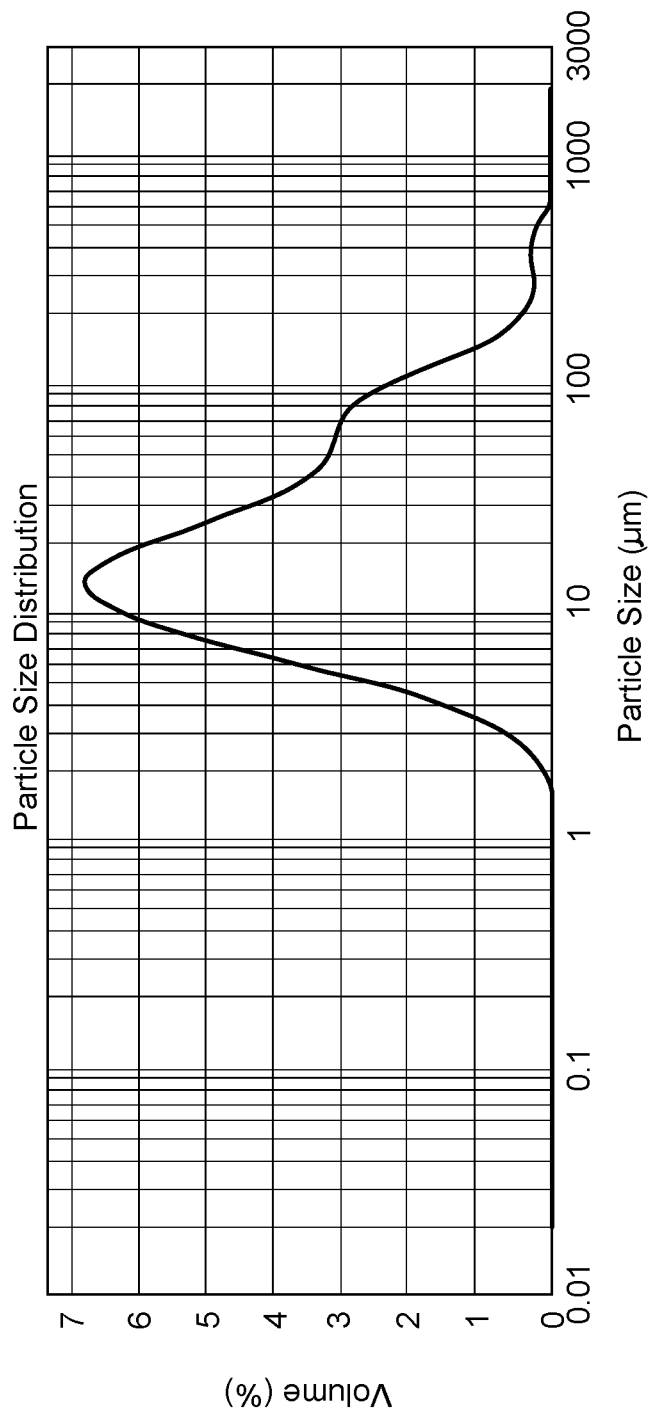
Figure 5G:
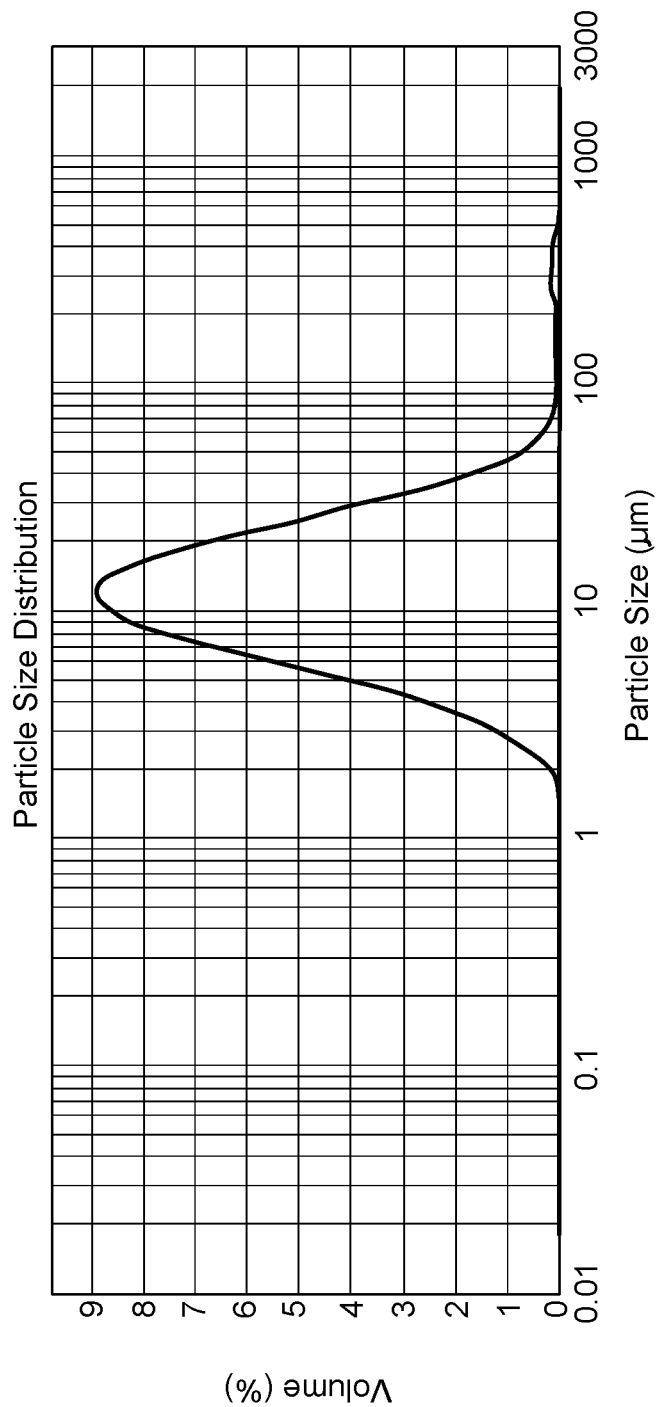
Figure 5I:
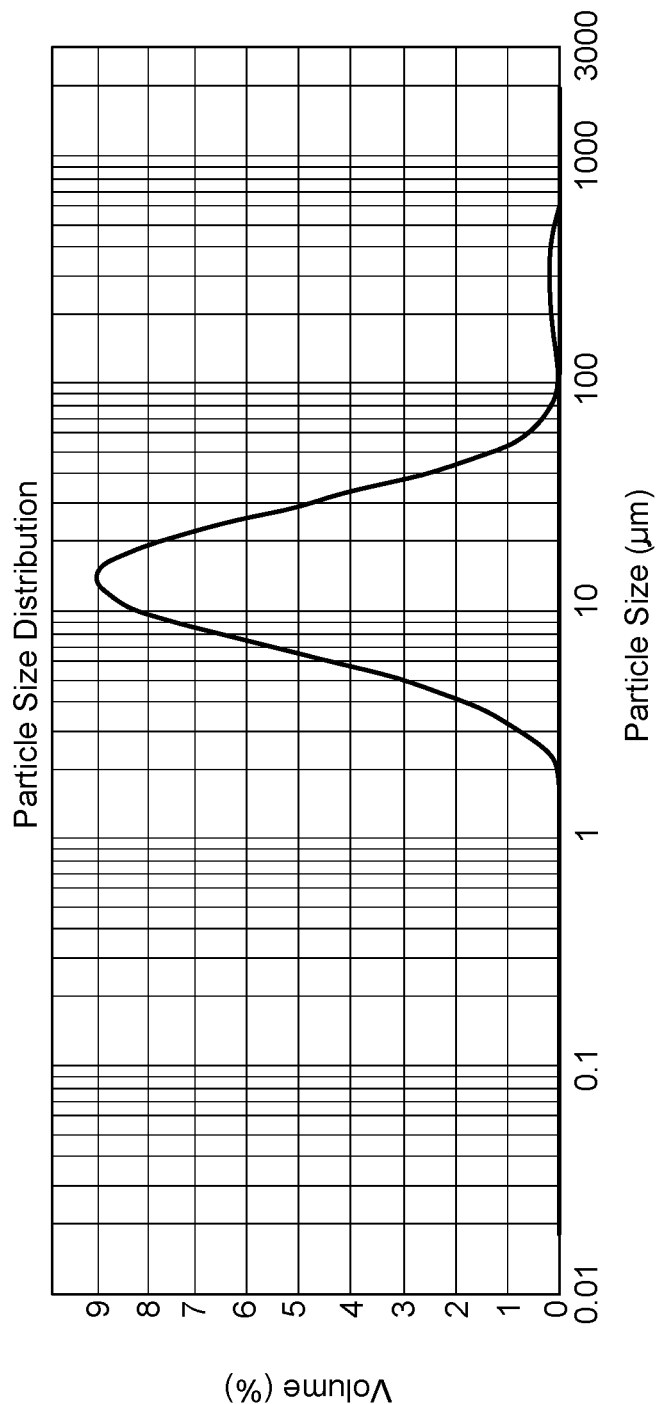
Figure 5K:
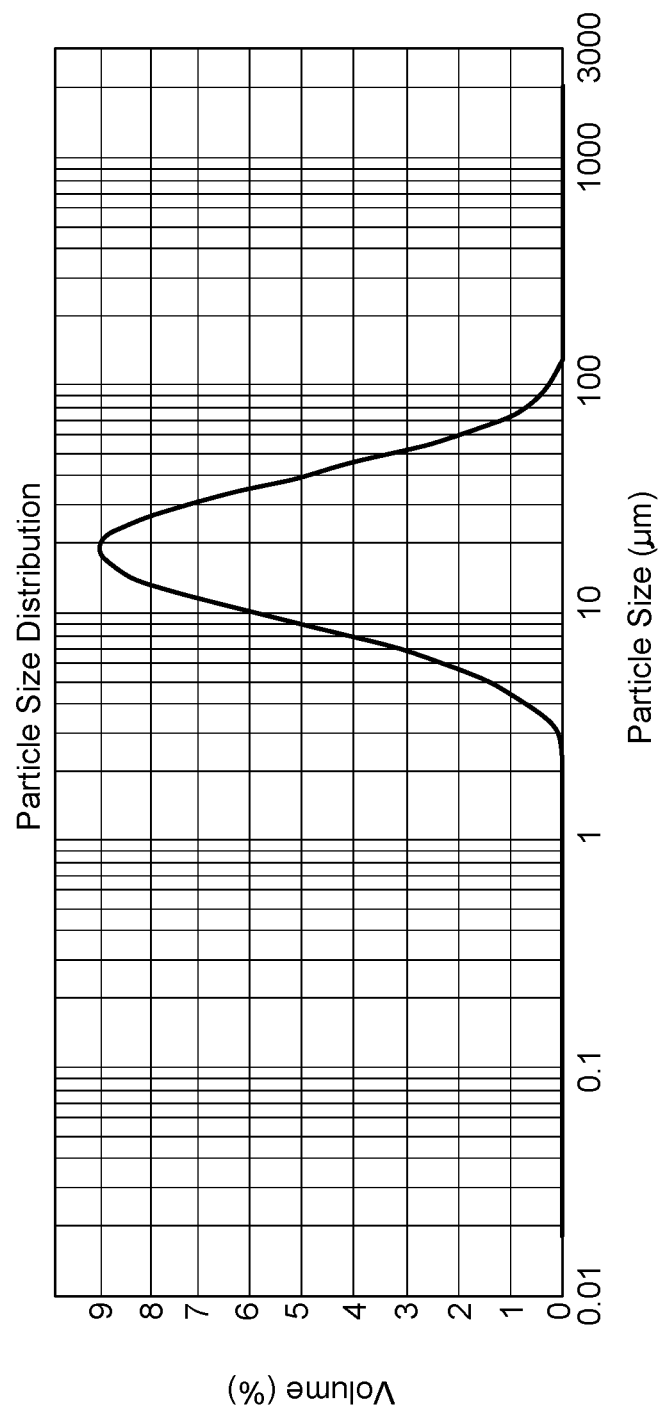
Figure 5M:
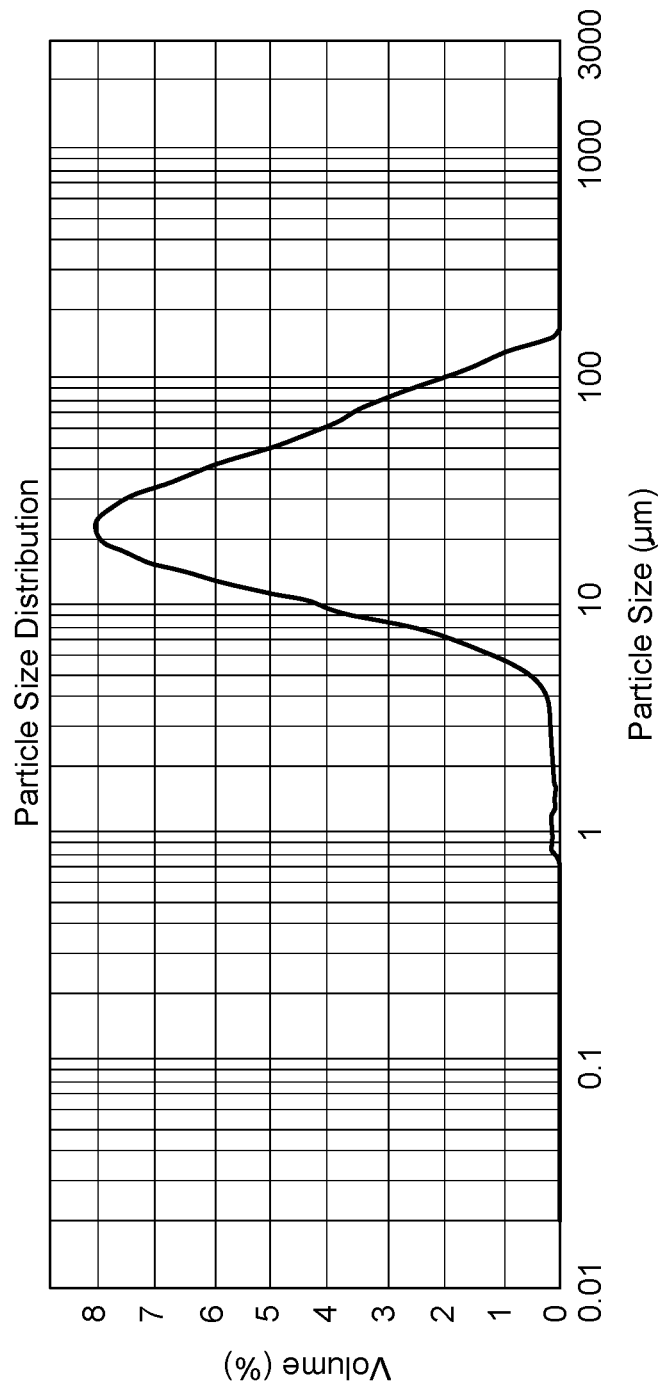
Figure 50:
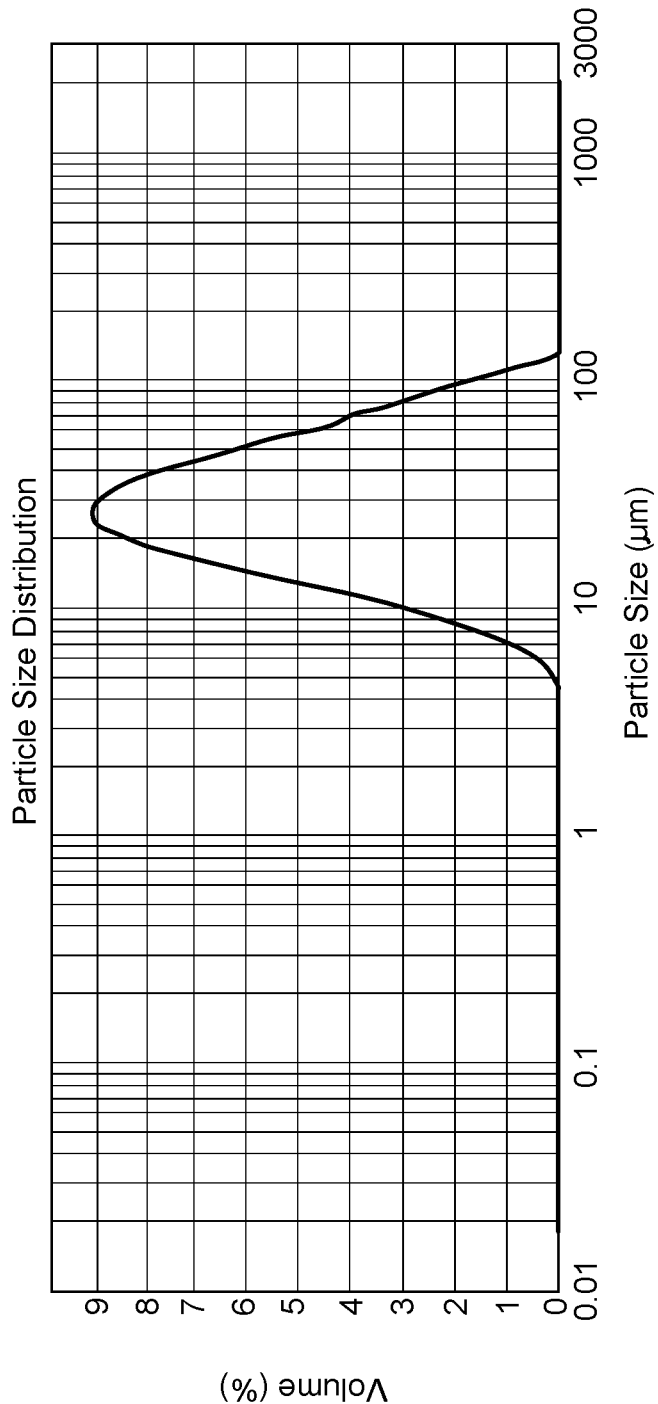
Figure 5Q:
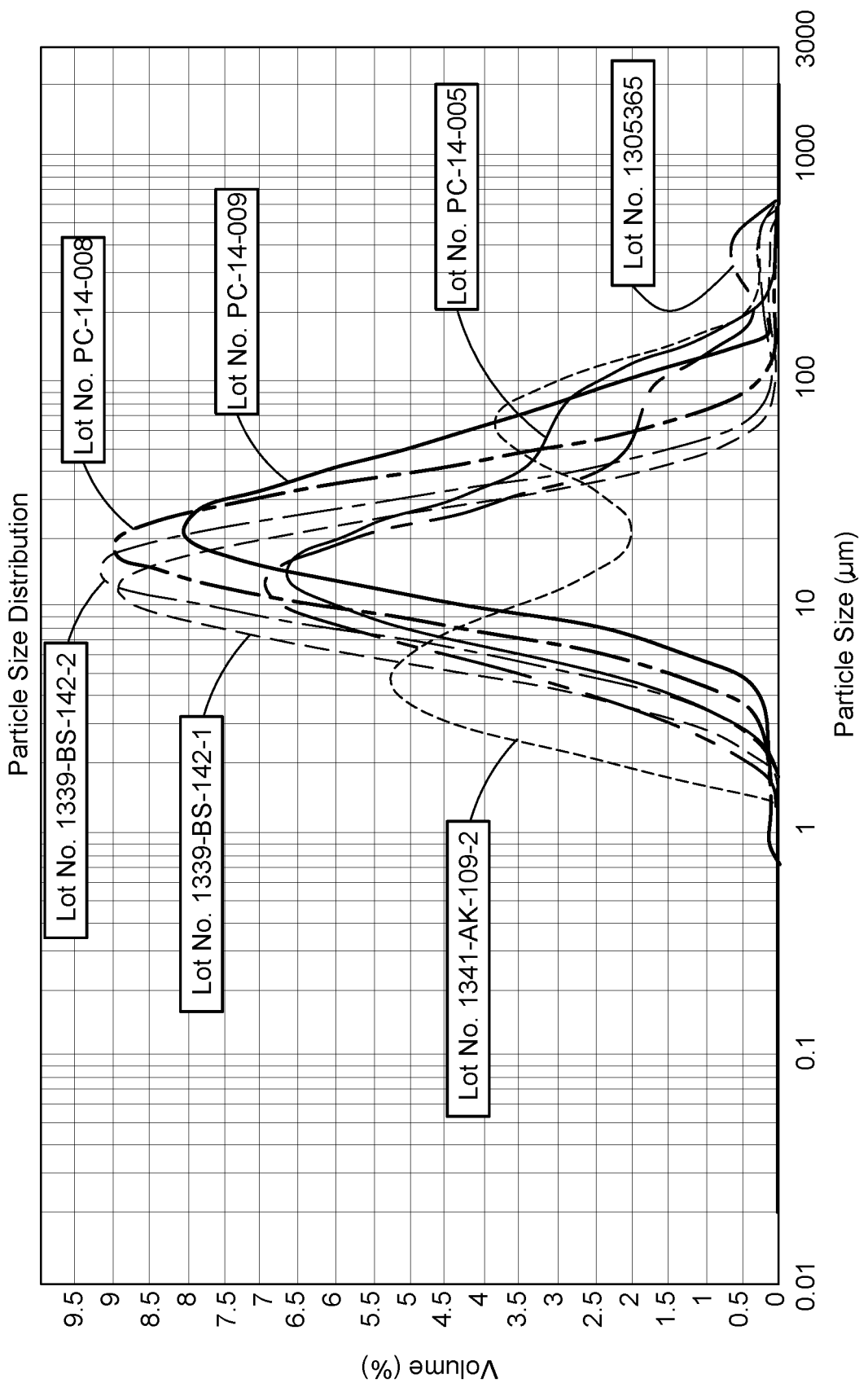
FIG. 5Q is a graph and shows an overlay of the particle size distributions depicted in the graphs of FIGS. 5A-5P.

| Lot No. | d10 (μm)[a] | d50 (μm)[b] | d90 (μm)[c] | D[4,3] Volume weighted mean | Corresponding FIG. No. |
|---|---|---|---|---|---|
| 1305365 | 4.905 | 14.268 | 75.098 | 34.740 | FIG. 5A & FIG. 5B |
| 1341-AK-109-2 | 2.815 | 10.423 | 89.782 | 32.779 | FIG. 5C & FIG. 5D |
| PC-14-005 | 6.363 | 18.345 | 86.906 | 36.720 | FIG. 5E & FIG. 5F |
| 1339-BS-142-1 | 4.978 | 11.969 | 28.331 | 16.614 | FIG. 5G & FIG. 5H |
| 1339-BS-142-2 | 6.088 | 14.468 | 33.936 | 20.889 | FIG. 5I & FIG. 5J |
| PC-14-008 | 7.658 | 18.290 | 42.616 | 22.451 | FIG. 5K & FIG. 5L |
| PC-14-009 | 9.665 | 24.406 | 68.445 | 32.557 | FIG. 5M & FIG. 5N |
| 1405463 | 12.062 | 27.653 | 64.876 | 33.740 | FIG. 5O & FIG. 5P |

[a] 10% of the total volume of particles is comprised of particles no larger than the indicated size.
[b] 50% of the total volume of particles is comprised of particles no larger than the indicated size.
[c] 90% of the total volume of particles is comprised of particles no larger than the indicated size.

Particle size distributions for measurements obtained from the samples corresponding to the lots of selinexor described in Examples 1-5 were also overlaid in a graph. FIG. 5I is the graph resulting from overlaying the particle size distributions obtained from the samples corresponding to the lots of selinexor described in Examples 1-5, and shows that the distributions for four lots (Lot Nos. 1339-BS-142-1, 1339-BS-142-2, PC-14-008 and PC-14-009) had more a a unimodal characteristic than lot (Lot No. 1341-AK-109-2) which was distinctly bimodal. The distribution for Lot No. PC-14-005, like the sample used for method development (Lot No. 1305365), showed a primary mode approximately 12-15 μm, a secondary mode consisting of a shoulder on the side of the primary mode corresponding to particles approximately 80-90 μm and a minor tertiary mode approximately 400 μm.

Example 9. Process for Preparation of Selinexor

A new process for the preparation of the compound of Formula I was developed. The new process uses a T3P®-mediated coupling of KG1 with the hydrazinyl pyrazine (KJ8) to prepare selinexor such as described in International Publication No. WO 2013/019548, but incorporates changes to the reaction design. In particular, the process described herein wherein the unstable active T3P® ester is generated in situ can result in one or more of the following advantages over the process for the preparation of the compound of Formula I described in International Publication No. WO 2013/019548:

A reduction of the isomerization of the double bond in KH8;

A reduction in the production of side products such as 3-(3,5-Bis-trifluoromethyl-phenyl)-1H-[1,2,4]triazole (KF9);

An increase in purity; and

An increase in yield.

The process described herein has been implemented into multi-kilogram processes, see for example the 1 Kg scale process (see Example 5), providing the desired final product in about 80% yield overall. Details of the improved process for preparing selinexor are described in Examples 5 and 6.

Chemistry Development

A series of experiments aimed at generating the activated ester transiently were carried out. These experiments are summarized in Table 5. Initially, the addition mode of the raw materials into T3P® was maintained, but subsequently the order of addition of the raw materials was reversed when it was observed that the kinetics of the reaction of KJ8 with T3P® were overshadowed by the rate of formation (and presumably quench) of the T3P® ester of KG1. In addition to the improvements in the characteristics of the product of the coupling between KG1 and KJ8 discussed above, the addition of T3P® to a mixture of KG1, KJ8 and DIPEA provided a greatly simplified reactor flow and the need to very carefully handle the T3P® activated ester of KG1 once formed. Adding the T3P® last also allowed for much better control over the addition rates, avoiding the need to transfer the activated ester as rapidly as possible (a task that is much more difficult and potentially dangerous at larger scale). Reduction in the number of solutions that had to be prepared and transferred also allowed us to reduce the volume of the process.

TABLE 5

| Solvent | Temp °C. | Eq. T3P | Eq. KG1 | Eq. KJ8 | Type/Eq. Base | Type/Eq. Base #2 | Addn. order | IPC time | Conv. (% KH8/(% KG1 + KH8))*100 | Cis:Trans ratio | KF9 (wrt KH8) |
|---|---|---|---|---|---|---|---|---|---|---|---|
| MeTHF/ EtOAc | −40 to −45 | 1.4 | 1.00 | 1.1 | DIPEA 2.45 | NA | KG1/DIPEA/MeTHF cool −40° C. Charge T3P Add to KJ8 (−40° C.) | −40° C. 1 h RT O/N | 95.4% 97.4% | 98.4% 98.4% | 5.3% 5.4% |
| MeTHF/ EtOAc | −40 to −45 | 1.4 | 1.00 | 1.1 | DIPEA 2.45 | NA | T3P/MeTHF cool −40° C. KG1/KJ8/DIPEA | −40° C. 1 h RT O/N | 84.8% 93.8% | >99% >99% | 2.7% 2.7% |
| MeTHF/ EtOAc | −40 to −45 | 1.4 | 1.00 | 1.1 | DIPEA 1.0 | DIPEA 1.45 | T3P/MeTHF cool −40° C. KG1/KJ8/DIPEA (1) DIPEA (1.45) | −40° C. 1 h −40° C. 3 h RT WE | 81.2% 81.4% | >99% >99% | 2.95% 3.0% |
| MeTHF/ EtOAc | −40 to −45 | 1.4 | 1.00 | 1.1 | DIPEA 1.0 | DIPEA 1.45 | T3P/MeTHF Cool −40° C. Charge DIPEA (1.4) KG1/KJ8/DIPEA (1) | −40° C. 1 h −40 3 h | 77.7% 90.3% | 98.9% 99.2% | 4.0% 3.6% |
| MeTHF/ EtOAc | −40 to −45 | 1.4 | 1.00 | 1.1 | DIPEA 1.0 | DIPEA 1.45 | T3P/KJ8 cool −40° C. DIPEA (1.45) KG1/DIPEA (1) | −40° C. 30 m RT 1 h | 45.0% 63.5% | >99% >99% | 4.1% 3.65% |
| MeTHF/ EtOAc | −40 to −45 | 1.4 | 1.00 | 1.1 | DIPEA 2.45 | NA | T3P/KJ8 Cool −40° C. DIPEA Charge KG1/MeTHF | −40° C. 30 m RT 1 h | 13.4% 28.1% | >99% 98.5% | 12.0% |
| MeTHF/ EtOAc | −40 to −45 | 1.4 | 1.00 | 1.1 | DIPEA 2.0 | NA | Charge T3P/KJ8 Cool −40° C. Charge KG1/DIPEA | −40° C. 30 m RT 1 h | 69.1% 70.9% | >99% >99% | 2.8% 2.7% |
| MeTHF/ EtOAc | −40 to −45 | 1.4 | 1.00 | 1.25 | DIPEA 2.45 | NA | T3P/MeTHF Cool −40° C. KG1/KJ8/DIPEA (1) | −40° C. 90 m RT 1 h | 88.3% 96.4% | >99% >99% | 2.34% 2.25% |
| MeTHF/ EtOAc | −40 to −45 | 1.4 | 1.00 | 1.1 | DIPEA 2.45 | NA | KG1/MeTHF/DIPEA Cool −40° C. T3P KJ8/MeTHF | −40° C. 30 m RT 30 m | 97.2% 98.5% | 99% 98.6% | 3.8% 4.3% |
| MeTHF/ EtOAc | −40 to −45 | 1.4 | 1.00 | 1.1 | DIPEA 2.45 | NA | KG1/KJ8/MeTHF DIPEA Cool −40° C. T3P | −40° C. 90 m RT 1 h | 97.1% 98.0% | 98.9% 98.7% | 2.1% 2.1% |

Notes:
KF9 = 3-(3,5-Bis-trifluoromethyl-phenyl)-1H-[1,2,4]triazole.
Column labeled Temp °C. reflect a range of acceptable conditions, while the temperature listed in the column Addn. order reflects the actual temperature.

Investigation of reaction temperature is summarized in Table 6. Of particular note was the observation that the new chemistry did not require the use of cryogenic vessels, as the reaction could be run at −20° C. or even −10° C. with only a slight increase in the level of KF9 produced. In some embodiments, the stoichiometry based on 1.00 equivalent of KG1 is 1.05 equivalents of KJ8 and 1.6 equivalents of T3P. It is understood that the equivalents of KJ8, T3P or both can vary by ±5% without impact on purity and yield. In some embodiments, the reaction is run at −20° C. In some embodiments, the reaction is run at −40° C.

TABLE 6

| Solvent | Temp | Eq. T3P | Eq. KG1 | Eq. KJ8 | Type/Eq. Base | Addn. order | IPC time | Conv. (% KH8/(% KG1 + KH8))*100 | Cis:Trans ratio | KF9 (wrt KH8) |
|---|---|---|---|---|---|---|---|---|---|---|
| MeTHF/ EtOAc | −40 to −45 | 1.4 | 1.00 New | 1.1 | 2.45 | KG1/KJ8/MeTHF DIPEA Cool −40° C.; T3P | −40° C. 90 m RT 2.5 h | 97.2% 98.2% | >99.9% >99.9% | 0.48% 0.71% |
| MeTHF/ EtOAc | −20 to −25 | 1.4 | 1.00 New | 1.1 | 2.45 | KG1/KJ8/MeTHF DIPEA Cool −20° C.; T3P | −20° C. 40 m RT 1 h | 96.6% 97.6% | >99.9% >99.9% | 0.91% 0.96% |
| MeTHF/ EtOAc | −40 to −45 | 1.6 | 1.00 New | 1.1 | DIPEA 2.45 | KG1/KJ8/MeTHF DIPEA Cool −40° C.; T3P | −40° C. 5 m RT 1 h | 91.9% 99.0% | >99.9% >99.9% | 0.70% 0.90% |
| MeTHF/ EtOAc | −40 to −45 | 1.4 | 1.00 New | 1.4 | DIPEA 2.45 | KG1/KJ8/MeTHF DIPEA Cool −40° C.; T3P | −40° C. 10 m RT 1 h | 98.2% 99.4% | >99.9% >99.9% | 0.77% 0.86% |

TABLE 6-continued

| Solvent | Temp | Eq. T3P | Eq. KG1 | Eq. KJ8 | Type/Eq. Base | Addn. order | IPC time | Conv. (% KH8/(% KG1 + KH8))*100 | Cis:Trans ratio | KF9 (wrt KH8) |
|---|---|---|---|---|---|---|---|---|---|---|
| MeTHF/ EtOAc | −40 to −45 | 1.4 | 1.00 New | 1.4 | DIPEA 2.45 | KG1/KJ8/MeTHF DIPEA Cool −40° C.; T3P | −40° C. 10 m RT 1 h | 98.5% 99% | >99.9% | 0.90% |
| MeTHF/ EtOAc | −10 to −15 | 1.4 | 1.00 New | 1.4 | DIPEA 2.45 | KG1/KJ8/MeTHF DIPEA Cool −10° C.; T3P | −10° C. 10 m RT 1 h | 100% 100% | >99.9% >99.9% | 1.30% |

Note:
Column labeled Temp ° C. reflect a range of acceptable conditions, while the temperature listed in the column Addn. order reflects the actual temperature.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A single crystalline form of a compound represented by Structural Formula I:

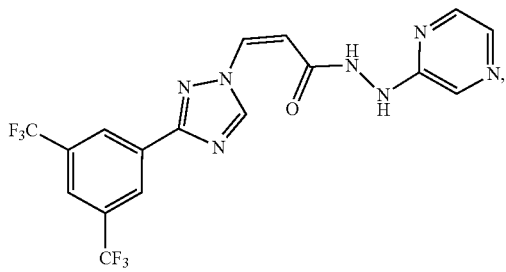

wherein the single crystalline form is an acetonitrile solvate of Form D and is characterized by at least three X-ray powder diffraction peaks at 2θ angles selected from 3.7°, 7.3°, 10.9°, 18.3° and 21.9°.

2. The single crystalline form of claim 1, characterized by X-ray powder diffraction peaks at 2θ angles of 3.7°, 7.3°, 10.9°, 18.3° and 21.9°.

3. The single crystalline form of claim 2, characterized by X-ray powder diffraction peaks at 2θ angles of 3.7°, 7.3°, 9.7°, 10.9°, 18.3°, 19.2° and 21.9°.

4. The single crystalline form of claim 3, characterized by X-ray powder diffraction peaks at 2θ angles of 3.7°, 7.3°, 9.7°, 10.9°, 11.1°, 18.3°, 19.2°, 19.5°, 20.6° and 21.9°.

5. The single crystalline form of claim 1, characterized by an X-ray powder diffraction pattern substantially in accordance with that depicted in FIG. 2A.

6. The single crystalline form of claim 1, wherein the solvate comprises from about 0.5 to about 1.5 molar equivalents of solute per molar equivalent of the compound of Structural Formula I.

7. The single crystalline form of claim 6, wherein the solvate comprises about one molar equivalent of solute per molar equivalent of the compound of Structural Formula I.

8. A method of preparing a single crystalline form of a compound represented by Structural Formula I:

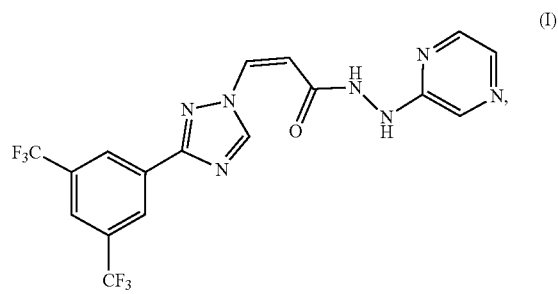 [SMILES: O=C(/C=C\n1cnc(-c2cc(C(F)(F)F)cc(C(F)(F)F)c2)n1)NNc1cnccn1]

wherein the single crystalline form is Form A and is characterized by at least three X-ray powder diffraction peaks at 2θ angles selected from 4.4°, 19.9°, 21.3° and 22.0°, the method comprising:
(a) suspending single crystalline Form D of the compound of Structural Formula I in isopropanol or a mixture of isopropanol and water to form a slurry, wherein single crystalline Form D is characterized by at least three X-ray powder diffraction peaks at 2θ angles selected from 3.7°, 7.3°, 10.9°, 18.3° and 21.9°;
(b) heating the slurry to a temperature less than or equal to about 70° C. to form a second slurry or a solution;
(c) cooling the second slurry or the solution and adding water to the second slurry or the solution, thereby forming solid particles of crystalline Form A of the compound of Structural Formula I; and
(d) isolating the solid particles of crystalline Form A,
thereby preparing a composition comprising particles of single crystalline Form A of the compound of Structural Formula I.

9. A method of preparing a single crystalline form of a compound represented by Structural Formula I:

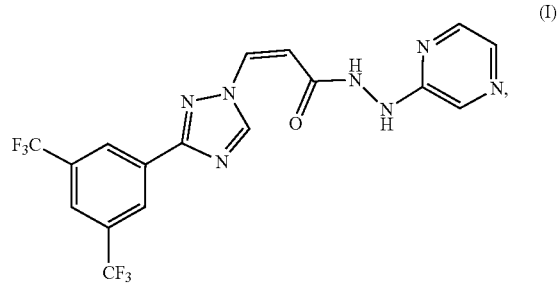 [SMILES: O=C(/C=C\n1cnc(-c2cc(C(F)(F)F)cc(C(F)(F)F)c2)n1)NNc1cnccn1]

wherein the single crystalline form is Form A and is characterized by at least three X-ray powder diffraction peaks at 2θ angles selected from 4.4°, 19.9°, 21.3° and 22.0°, the method comprising:
(a) suspending single crystalline Form D of the compound of Structural Formula I in isopropanol or a mixture of isopropanol and water to form a slurry, wherein single crystalline Form D is characterized by at least three X-ray powder diffraction peaks at 2θ angles selected from 3.7°, 7.3°, 10.9°, 18.3° and 21.9°;
(b) heating the slurry to a temperature less than or equal to about 70° C. to form a second slurry or a solution;
(c) adding water to the second slurry or the solution and cooling the second slurry or the solution, thereby forming solid particles of crystalline Form A of the compound of Structural Formula I; and
(d) isolating the solid particles of crystalline Form A,
thereby preparing a composition comprising particles of single crystalline Form A of the compound of Structural Formula I.

10. The method of claim 8, wherein the solid particles have a unimodal particle size distribution characterized by a d(0.9) of 100 microns or less.

11. The method of claim 8, wherein the ratio of isopropanol to water by volume in the mixture of isopropanol and water is from about 0.1 to about 4.

12. The method of claim 8, wherein single crystalline Form D of the compound of Structural Formula I is suspended in an amount of isopropanol or mixture of isopropanol and water of from about 5 to about 10 parts by weight with respect to single crystalline Form D of the compound of Structural Formula I.

13. The method of claim 8, wherein the slurry is heated to a temperature of from about 35° C. to about 70° C.

14. The method of claim 8, wherein the second slurry or the solution is cooled to from about 0° C. to about 55° C.

15. The method of claim 8, wherein water is added to the second slurry or the solution in an amount of from about 5 parts by weight to about 15 parts by weight with respect to single crystalline Form D of the compound of Structural Formula I.

16. A method of preparing a single crystalline form of a compound represented by Structural Formula I:

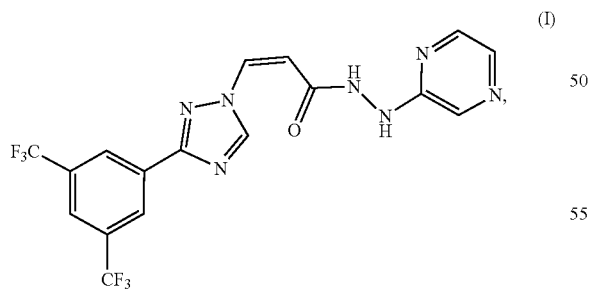

wherein the single crystalline form is Form A and is characterized by at least three X-ray powder diffraction peaks at 2θ angles selected from 4.4°, 19.9°, 21.3° and 22.0°, the method comprising:
heating single crystalline Form D of the compound of Structural Formula I and inducing formation of solid particles of crystalline Form A; or maturing single crystalline Form D of the compound of Structural Formula I in a solvent system and inducing formation of solid particles of crystalline Form A; or drying single crystalline Form D of the compound of Structural Formula I, thereby forming solid particles of crystalline Form A; or any combination of the foregoing; and
isolating the solid particles of crystalline Form A,
thereby preparing single crystalline Form A of the compound of Structural Formula I.

17. A method of preparing a single crystalline form of a compound represented by Structural Formula I:

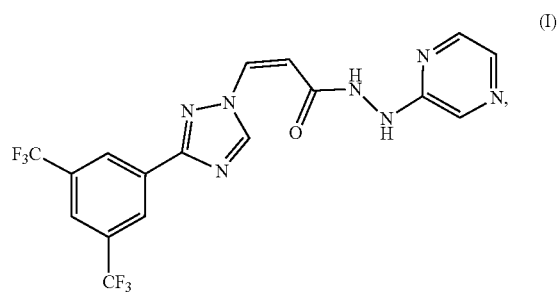 [SMILES: O=C(/C=C\n1cnc(-c2cc(C(F)(F)F)cc(C(F)(F)F)c2)n1)NNc1cnccn1]

wherein the single crystalline form is an acetonitrile solvate of Form D and is characterized by at least three X-ray powder diffraction peaks at 2θ angles selected from 3.7°, 7.3°, 10.9°, 18.3° and 21.9°, the method comprising:
dissolving the compound of Structural Formula I in a solvent system comprising greater than 20% by volume acetonitrile;
inducing formation of solid particles of crystalline Form D of the compound of Structural Formula I, wherein the temperature of the solvent system is below 50°; and
isolating the solid particles of crystalline Form D,
thereby preparing the acetonitrile solvate of single crystalline Form D of the compound of Structural Formula I.

18. The method of claim 17, wherein inducing formation of solid particles of the acetonitrile solvate of crystalline Form D comprises cooling the solution formed by dissolving the compound of Structural Formula I in a solvent system comprising acetonitrile.

19. A method of preparing a single crystalline form of a compound represented by Structural Formula I:

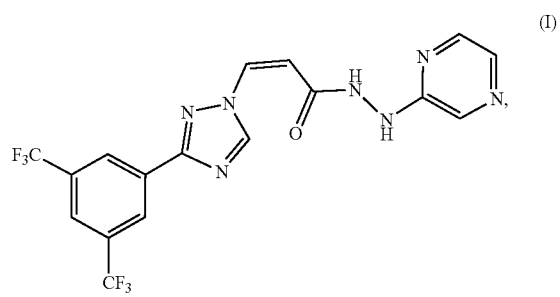 [SMILES: O=C(/C=C\n1cnc(-c2cc(C(F)(F)F)cc(C(F)(F)F)c2)n1)NNc1cnccn1]

wherein the single crystalline form is Form A and is characterized by at least three X-ray powder diffraction peaks at 2θ angles selected from 4.4°, 19.9°, 21.3° and 22.0°, the method comprising:

(a) combining a trialkylamine, 2-methyltetrahydrofuran, a compound of Structural Formula II:

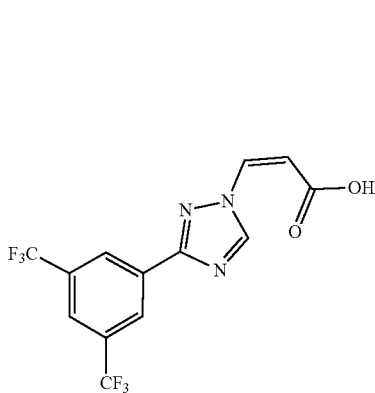

(II)

and a compound of Structural Formula III:

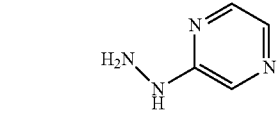

(III)

to form a reaction mixture;

(b) cooling the reaction mixture to from about −80° C. to about 0° C.;

(c) treating the reaction mixture with propylphosphonic anhydride to provide a mixture comprising the compound of Structural Formula I;

(d) isolating the compound of Structural Formula I from the mixture;

(e) dissolving the isolated compound of Structural Formula I in a solvent system comprising acetonitrile;

(f) inducing formation of solid particles of crystalline Form D of the compound of Structural Formula I and isolating the solid particles of crystalline Form D to obtain single crystalline Form D of the compound of Structural Formula I, wherein single crystalline Form D is characterized by at least three X-ray powder diffraction peaks at 2θ angles selected from 3.7°, 7.3°, 10.9°, 18.3° and 21.9°;

(g) heating single crystalline Form D, and inducing formation of solid particles of crystalline Form A; or maturing single crystalline Form D, in a solvent system and inducing formation of solid particles of crystalline Form A; or drying single crystalline Form D, thereby forming solid particles of crystalline Form A; or any combination of the foregoing; and (h) isolating the particles of crystalline Form A, thereby preparing single crystalline Form A of the compound of Structural Formula I.

20. A method of preparing a single crystalline form of a compound represented by Structural Formula I:

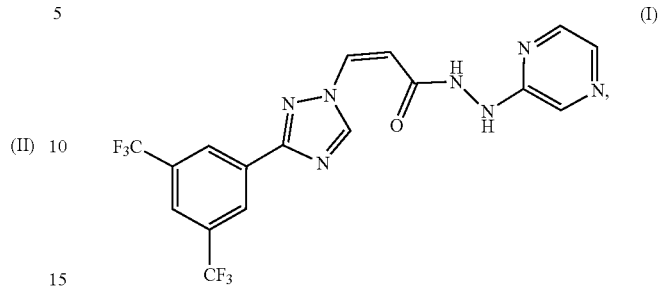

(I)

wherein the single crystalline form is Form A and is characterized by at least three X-ray powder diffraction peaks at 2θ angles selected from 4.4°, 19.9°, 21.3° and 22.0°, the method comprising:

(a) combining a trialkylamine, 2-methyltetrahydrofuran, a compound of Structural Formula II:

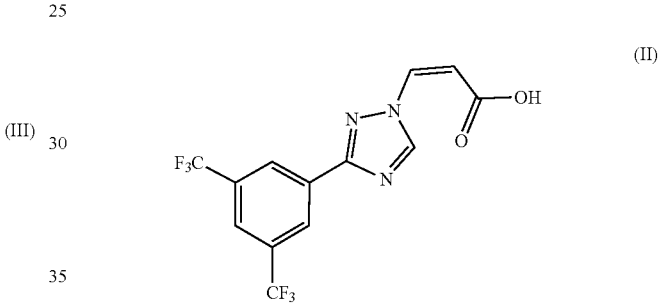

(II)

and a compound of Structural Formula III:

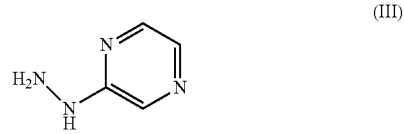

(III)

to form a reaction mixture;

(b) cooling the reaction mixture to from about −80° C. to about 0° C.;

(c) treating the reaction mixture with propylphosphonic anhydride to provide a mixture comprising the compound of Structural Formula I;

(d) isolating the compound of Structural Formula I from the mixture;

(e) dissolving the isolated compound of Structural Formula I in a solvent system comprising acetonitrile;

(f) inducing formation of solid particles of crystalline Form D of the compound of Structural Formula I and isolating the solid particles of crystalline Form D, wherein single crystalline Form D is characterized by at least three X-ray powder diffraction peaks at 2θ angles selected from 3.7°, 7.3°, 10.9°, 18.3° and 21.9°;

(g) suspending single crystalline Form D in isopropanol or a mixture of isopropanol and water to form a slurry;

(h) heating the slurry to a temperature less than or equal to about 70° C. to form a second slurry or a solution;

(i) cooling the second slurry or the solution and adding water to the second slurry or the solution, thereby forming solid particles of crystalline Form A of the compound of Structural Formula I; and
(j) isolating the solid particles of crystalline Form A, thereby preparing single crystalline Form A of the compound of Structural Formula I.

* * * * *